US008211656B2

(12) United States Patent
Hyde et al.

(10) Patent No.: US 8,211,656 B2
(45) Date of Patent: Jul. 3, 2012

(54) BIOLOGICAL TARGETING COMPOSITIONS AND METHODS OF USING THE SAME

(75) Inventors: Roderick A. Hyde, Redmond, WA (US); Muriel Y. Ishikawa, Livermore, CA (US); Edward K. Y. Jung, Bellevue, WA (US); William Gates, Redmond, WA (US); Alois A. Langer, Harrison City, PA (US); Eric C. Leuthardt, St. Louis, MO (US); Royce A. Levien, Lexington, MA (US); Clarence T. Tegreene, Bellevue, WA (US); Thomas A. Weaver, San Mateo, CA (US); Charles Whitmer, North Bend, WA (US); Lowell L. Wood, Jr., Bellevue, WA (US); Victoria Y. H. Wood, Livermore, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 857 days.

(21) Appl. No.: 12/228,880

(22) Filed: Aug. 13, 2008

(65) Prior Publication Data

US 2010/0041014 A1    Feb. 18, 2010

(51) Int. Cl.
G01N 31/00    (2006.01)
G01N 33/53    (2006.01)

(52) U.S. Cl. ........ 435/7.21; 435/7.1; 436/501; 436/518; 424/9.1; 424/520; 422/50; 530/300; 530/350

(58) Field of Classification Search .................. None
See application file for complete search history.

(56) References Cited

U.S. PATENT DOCUMENTS

| | | | |
|---|---|---|---|
| 4,327,710 A | 5/1982 | DeLoach et al. |
| 4,652,449 A | 3/1987 | Ropars et al. |
| 4,935,223 A | 6/1990 | Phillips |
| 5,470,570 A | 11/1995 | Taylor et al. |
| 5,653,999 A | 8/1997 | Gaudreault et al. |
| 5,677,176 A | 10/1997 | Nicolau et al. |
| 5,753,221 A | 5/1998 | Magnani et al. |
| 5,843,440 A | 12/1998 | Pouletty et al. |
| 5,993,809 A | 11/1999 | Weaver et al. |
| 6,132,992 A | 10/2000 | Ledbetter et al. |
| 6,139,836 A | 10/2000 | Magnani et al. |
| 6,153,427 A | 11/2000 | King et al. |
| 6,312,957 B1 | 11/2001 | Einerhand et al. |
| 6,326,198 B1 | 12/2001 | Emerson et al. |
| 6,495,351 B2 | 12/2002 | McHale |
| 6,500,419 B1 | 12/2002 | Hone et al. |
| 6,506,381 B1 | 1/2003 | Bitensky et al. |
| 6,645,464 B1 | 11/2003 | Hainfeld |
| 6,787,154 B2 | 9/2004 | Albani |
| 6,812,204 B1 | 11/2004 | McHale et al. |
| 6,942,993 B2 | 9/2005 | Qiu |
| 6,946,127 B2 | 9/2005 | Bitensky et al. |
| 7,045,677 B2 | 5/2006 | Cottingham et al. |
| 7,056,700 B2 | 6/2006 | Galen |
| 7,214,190 B1 | 5/2007 | Wilson |
| 2002/0042127 A1 | 4/2002 | Russell et al. |
| 2002/0151004 A1 | 10/2002 | Craig |
| 2003/0215454 A1 | 11/2003 | Colb et al. |
| 2004/0033232 A1 | 2/2004 | Ramberg et al. |
| 2004/0033584 A1 | 2/2004 | Lederberg |
| 2004/0071664 A1 | 4/2004 | McHale et al. |
| 2005/0118193 A1 | 6/2005 | Andino-Pavlovsky et al. |
| 2005/0171434 A1 | 8/2005 | Madden et al. |
| 2005/0276861 A1 | 12/2005 | Kipp et al. |
| 2006/0018912 A1 | 1/2006 | Finberg et al. |
| 2006/0068388 A1 | 3/2006 | Barberis et al. |
| 2006/0083716 A1 | 4/2006 | Kaufman et al. |
| 2006/0105974 A1 | 5/2006 | Lange et al. |
| 2006/0172318 A1 | 8/2006 | Medinz et al. |
| 2006/0188490 A1 | 8/2006 | Hoerr et al. |
| 2006/0270030 A1 | 11/2006 | Voigt et al. |
| 2007/0059316 A1 | 3/2007 | Pallenberg et al. |
| 2007/0077572 A1 | 4/2007 | Tawfik et al. |
| 2007/0082392 A1 | 4/2007 | Glaser |
| 2007/0218552 A1 | 9/2007 | Giarratana et al. |
| 2007/0243137 A1 | 10/2007 | Hainfeld |
| 2009/0311253 A1 | 12/2009 | Ghayur et al. |

OTHER PUBLICATIONS

Bar-Zvi et al.; "Assembled Clathrin in Erythrocytes"; The Journal of Biological Chemistry; Dec. 25, 1987; pp. 17719-17723; vol. 262, No. 36; The American Society for Biochemistry and Molecular Biology, Inc.
Battisti et al.; "Development of a System for Genetic Manipulation of *Bartonella bacilliformis*"; Applied and Environmental Microbiology; Aug. 1999; pp. 3441-3448; vol. 65, No. 8; American Society for Microbiology.
Benson et al.; "GenBank"; Nucleic Acids Research; 2007; pp. D21-D25; vol. 35; The Author(s).
Bettinger et al.; "Peptide-mediated RNA delivery: a novel approach for enhanced transfection of primary and post-mitotic cells"; Nucleic Acids Research; 2001; pp. 3882-3891; vol. 29, No. 18; Oxford University Press.
Bierhuizen et al.; "Efficient detection and selection of immature rhesus monkey and human CD34+ hematopoietic cells expressing the enhanced green fluorescent protein (EGFP)"; Leukemia; 1999; pp. 605-613; vol. 13; Stockton Press.
Bliss et al.; "Susceptibility of *Candida* Species to Photodynamic Effects of Photofrin"; Antimicrobial Agents and Chemotherapy; Jun. 2004; pp. 2000-2006; vol. 48, No. 6; American Society of Microbiology. Bracey et al.; "Ex Vivo Selective Isolation of Young Red Blood Cells Using the IBM-2991 Cell Washer"; Blood; Jun. 1983; pp. 1068-1071; vol. 61, No. 6; Grune & Stratton, Inc.
Bratosin et al.; "Improved Storage of Erythrocytes by Prior Leukodepletion: Flow Cytometric Evaluation of Stored Erythrocytes"; Cytometry (Communications in Clinical Cytometry); 2001; pp. 351-356; vol. 46; Wiley-Liss, Inc.
Bratosin et al.; "Molecular Mechanisms of Erythrophagocytosis: Flow Cytometric Quantitation of In Vitro Erythrocyte Phagocytosis by Macrophages"; Cytometry (Communications in Clinical Cytometry); 1997; pp. 269-274; vol. 30; Wiley-Liss, Inc.
Brennan, John D.; "Preparation and Entrapment of Fluorescently Labeled Proteins for the Development of Reagentless Optical Biosensors"; Journal of Fluorescence; 1999; pp. 295-312; vol. 9, No. 4; Plenum Publishing Coroporation.
Bright et al.; "Regenerable Fiber-Optic-Based Immunosensor"; Analytical Chemistry; May 15, 1990; pp. 1065-1069; vol. 62, No. 10; American Chemical Society.

(Continued)

Primary Examiner — Lisa Cook

(57) ABSTRACT

Modified red blood cells are described. In an embodiment, the modified red blood cell includes a target-binding agent. Targeted delivery of imaging agents, drugs, and peptide and protein pharmaceuticals using modified red blood cells are described. Processes for preparing the modified red blood cells, pharmaceutical and diagnostic compositions containing the same and methods of diagnosis and treatment involving the modified red blood cells are described.

24 Claims, 10 Drawing Sheets

OTHER PUBLICATIONS

Brun et al.; "A New Method for Isolation of Reticulocytes: Positive Selection of Human Reticulocytes by Immunomagnetic Separation"; Blood; 1990; pp. 2397-2403; vol. 76, No. 11; The American Society of Hematology.

Cady et al.; "Optimized linkage and quenching strategies for quantum dot molecular beacons"; Molecular and Cellular Probes; 2007; pp. 116-124; vol. 21; Elsevier Ltd.

Cao et al.; "Molecular Beacon Aptamers for Protein Monitoring in Real-Time and in Homogeneous Solutions"; Current Proteomics; 2005; pp. 31-40; vol. 2, No. 1; Bentham Science Publishers Ltd.

Chen et al.; "Aptamer from whole-bacterium SELEX as new therapeutic reagent against virulent Mycobacterium tuberculosis"; Biochemical and Biophysical Research Communications; 2007; pp. 743-748; vol. 357; Elsevier Inc.

Christian et al.; "Nucleolin expressed at the cell surface is a marker of endothelial cells in angiogenic blood vessels"; The Journal of Cell Biology; Nov. 24, 2003; pp. 871-878; vol. 163, No. 4; The Rockefeller University Press.

Coleman et al.; "Establishing a Direct Role for the *Bartonella bacilliformis* Invasion-Associated Locus B (IaIB) Protein in Human Erythrocyte Parasitism"; Infection and Immunity; Jul. 2001; pp. 4373-4381; vol. 69, No. 7; American Society for Microbiology.

Conrad et al.; "Considerations on Antibody-Phage Display Methodology"; Combinatorial Chemistry & High Throughput Screening; 2005; pp. 117-126; vol. 8, No. 2; Bentham Science Publishers Ltd.

Cooke et al.; "Protein trafficking in *Plasmodium falciparum*-infected red blood cells"; TRENDS in Parasitology; Dec. 2004; pp. 581-589; vol. 20, No. 12; Elsevier Ltd.

Cornelissen et al.; "Cellular penetration and nuclear importation properties of $^{111}$In-labeled and $^{123}$I-labeled HIV-1 tat peptide immunoconjugates in BT-474 human breast cancer cells"; Nuclear Medicine and Biology; 2007; 37-46; vol. 34; Elsevier Ltd.

Cossart et al.; "Bacterial Invasion: The Paradigms of Enteroinvasive Pathogens"; Science; Apr. 9, 2004; pp. 242-248; vol. 304.

Cristofanilli et al.; "Circulating Tumor Cells, Disease Progression, and Survival in Metastatic Breast Cancer"; The New England Journal of Medicine; Aug. 19, 2004; pp. 781-791; vol. 351, No. 8; Massachusetts Medical Society.

Dehio, Christoph; "Molecular and Cellular Basis of *Bartonella* Pathogenesis"; Annual Review Microbiology; 2004; pp. 365-390; vol. 58; Annual Reviews.

Dehio et al.; "Construction of versatile high-level expression vectors for *Bartonella henselae* and the use of green fluorescent protein as a new expression marker"; Gene; 1998; pp. 223-229; vol. 215; Elsevier Science B.V.

Deitsch et al.; "Transformation of malaria parasites by the spontaneous uptake and expression of DNA from human erthrocytes"; Nucleic Acids Research; 2001; pp. 850-853; vol. 29, No. 3.

Demidova et al.; "Effect of Cell-Photosensitizer Binding and Cell Density on Microbial Photoinactivation"; Antimicrobial Agents and Chemotherapy; Jun. 2005; pp. 2329-2335; vol. 49, No. 6; American Society for Microbiology.

Eppelmann et al.; "Engineered Biosynthesis of the Peptide Antibiotic Bacitracin in the Surrogate Host *Bacillus subtilis*\*"; The Journal of Biological Chemistry; Sep. 14, 2001; pp. 34824-34831; vol. 276, No. 37; The American Society for Biochemistry and Molecular Biology, Inc.

Fan et al.; "Structures in *Bacillus subtilis* Are Recognized by CD14 in a Lipopolysaccharide Binding Protein-Dependent Reaction"; Infection and Immunity; Jun. 1999; pp. 2964-2968; vol. 67, No. 6; American Society for Microbiology.

Flynn et al.; "Methotrexate-loaded, photosensitized erthrocytes: a photo-activatable carrier/delivery system for use in cancer therapy"; Cancer Letters; 1994; pp. 225-229; vol. 82; Elsevier Science Ireland Ltd.

Francisco et al.; "Production and fluorescence-activated cell sorting of *Escherichia coli* expressing a functional antibody fragment on the external surface"; The Proceedings of the National Academy of Sciences USA, Biochemistry; Nov. 1993; pp. 10444-10448; vol. 90.

Friedberg et al.; "Brief Reports, In vitro effects of photodynamic therapy on *Aspergillus fumigatus*"; Journal of Antimicrobial Chemotherapy; 2001; pp. 105-107; vol. 48; The British Society of Antimicrobial Chemotherapy.

Garcia et al.; "Developmental Biology of Sporozoite-Host Interations in *Plasmodium falciparum* Malaria: Implications for Vaccine Design"; Clinical Microbiology Reviews; Oct. 2006; pp. 686-707; vol. 19, No. 4; American Society of Microbiology.

Georgiou et al.; "Preparative expression of secreted proteins in bacteria: status report and future prospects"; Current Opinion in Biotechnology; 2005; pp. 538-545; vol. 16; Elsevier Ltd.

Giarratana et al.; "Ex vivo generation of fully mature human red blood cells from hematopoietic stem cells"; Nature Biotechnology; Jan. 2005; pp. 69-74; vol. 23, No. 1; Nature Publishing Group.

Goodman et al.; "The Isolation of Reticulocyte-Free Human Red Blood Cells"; Proteomic-Quality RBCS; 2007; pp. 1470-1476; Society for Experimental Biology and Medicine.

Gottlieb et al.; "Inactivation of Trypanosoma cruzi Trypomastigote Forms in Blood Components by Photodynamic Treatment With Phthalocyanines"; Photochemisty and Photobiology; 1995; pp. 869-874; vol. 62, No. 5; American Society for Photobiology.

Haisma et al.; "Targeting of adenoviral vectors through a bispecific single-chain antibody"; Cancer Gene Therapy; 2000; pp. 901-904; vol. 7, No. 6; Nature America, Inc.

Hamidi et al.; "Review, Applications of carrier erythrocytes in delivery of biopharmaceuticals"; Journal of Controlled Release; 2007; pp. 145-160; vol. 118; Elsevier B.V.

Harris et al.; "A novel streptococcal surface protease promotes virulence, resistance to opsonophagocytosis, and cleavage of human fibrinogen"; The Journal of Clinical Investigation; Jan. 2003; pp. 61-70; vol. 111, No. 1.

Harris et al.; "Molecular Identification of a Malaria Merozoite Surface Sheddase"; PLoS Pathogens; Nov. 2005; pp. 0241-0251; vol. 1, Issue 3; Harris et al.

Ho et al.; "Isolation of anti-CD22 Fv with high affinity by Fv display on human cells"; PNAS, Medical Sciences; Jun. 20, 2006; pp. 9637-9643; vol. 103, No. 25.

Hossle et al.; "Gene Therapy of Hematopoietic Stem Cells: Strategies for Improvement"; Articles, News in Physiological Sciences; Jun. 2002; pp. 87-92; vol. 17; Int. Union Physiol. Sci./Am. Physiol. Soc./Am. Physiol. Soc.

Jaiswal et al.; "Long-term multiple color imaging of live cells using quantum dot bioconjugates"; Nature Biotechnology; Jan. 2003; pp. 47-51; vol. 21; Nature Publishing Group.

Jakobsen et al.; "Phage Display-Derived Human Monoclonal Antibodies Isolated by Binding to the Surface of Live Primary Breast Cancer Cells Recognize GRP78"; Cancer Research; Oct. 1, 2007; pp. 9507-9517;vol. 67, No. 19; American Association of Cancer Research.

Jhaveri et al.; "In vitro selection of signaling aptamers"; Nature Biotechnology; Dec. 2000; pp. 1293-1297; vol. 18; Nature America Inc.

Kadekoppala et al.; "Stable Expression of a New Chimeric Fluorescent Reporter in the Human Malaria Parasite *Plasmodium falciparum*"; Infection and Immunity; Apr. 2000; pp. 2328-2332; vol. 68, No. 4; American Society of Microbiology.

Keller et al.; "Transgene expression, but not gene delivery, is improved by adhesion-assisted lipofection of hematopoietic cells"; Gene Therapy; 1999; pp. 931-938; vol. 6; Stockton Press.

Koo et al.; "Development of a Streptavidin-Conjugated Single-Chain Antibody That Binds *Bacillus cereus* Spores"; Applied and Environmental Microbiology; Jul. 1998; pp. 2497-2502; vol. 64, No. 7; American Society for Microbiology.

Krag et al.; "Selection of Tumor-binding Ligands in Cancer Patients with Phage Display Libraries"; Cancer Research; Aug. 1, 2006; pp. 7724-7733; vol. 66, No. 15; American Association for Cancer Research.

Kumar et al.; "Falcipain-1, a *Plasmodium falciparum* Cysteine Protease with Vaccine Potential"; Infection and Immunity; Apr. 2007; pp. 2026-2034; vol. 75, No. 4; American Society for Microbiology.

Kupper et al.; "Generation of human antibody fragments against *Streptococcus* mutans using a phage display chain shuffling approach"; BMC Biotechnology; 2005; pp. 1-12; vol. 5, No. 4; Kupper et al.

Lacount et al.; "Expression and Function of the *Trypanosoma brucei* Major Surface Protease (GP63) Genes"; The Journal of Biological Chemisty; Jul. 4, 2003; pp. 24658-24664; vol. 278, No. 27; The American Society for Biochemistry and Molecular Biology, Inc.

Larsson et al.; "Syncytin and Cancer Cell Fusions"; The Scientific World Journal; 2007; pp. 1193-1197; vol. 7; TheScientificWorld: www.thescientificworld.com.

Lee et al.; "Detection of singlet oxygen production for PDT treatments both in vitro and in vivo using a diode laser-based singlet oxygen monitor"; Physical Sciences Inc.; 2006; pp. 1-6; Society of Photo-Optical Instrumentation Engineers.

Lee et al.; "Extracellular proteases as targets for treatment of cancer metastases"; Chemical Society Reviews; 2004; pp. 401-409; vol. 33; The Royal Society of Chemistry.

Lee et al.; "Phage-Display Selection of a Human Single-Chain Fv Antibody Highly Specific for Melanoma and Breast Cancer Cells Using a Chemoenzymatically Synthesized $G_{M3}$-Carbohydrate Antigen"; Journal of the American Chemical Society; 2002; pp. 12439-12446; vol. 124; American Chemical Society.

Liu et al.; "Bacterial glycosidases for the production of universal red blood cells"; Nature Biotechnology; Apr. 2007; pp. 454-464; vol. 25, No. 4; Nature Publishing Group.

Liu et al.; "Heteroantibody duplexes target cells for lysis by cytotoxic T lymphocytes"; Proceedings of the National Academy of Sciences USA, Immunology; Dec. 1985; pp. 8648-8652; vol. 82.

Magnani et al.; "Erythrocyte-mediated delivery of drugs, peptides and modified oligonucleotides"; Gene Therapy; 2002; pp. 749-751; vol. 9; Nature Publishing Group.

Maisch et al.; "The role of singlet oxygen and oxygen concentration in photodynamic inactivation of bacteria"; PNAS, Applied, Physical Sciences, Microbiology; Apr. 24, 2007; pp. 7223-7228; vol. 104, No. 17; The National Academy of Sciences of the USA.

Majander et al.; "Extracellular secretion of polypeptides using a modified *Escherichia coli* flagellar secretion apparatus"; Nature Biotechnology, Letters; Apr. 2005; pp. 475-481; vol. 23, No. 4; Nature Publishing Group.

Malik et al.; "Rapid Communication, An In Vitro Model of Human Red Blood Cell Production From Hematopoietic Progenitor Cells"; Blood; Apr. 15, 1998; pp. 2664-2671; vol. 91, No. 8; The American Society of Hematology.

Mallikaratchy et al.; "Cell Specific Aptamer-Photosensitizer Conjugates as a Molecular Tool in Photodynamic Therapy"; Chemmedchem; 2007; pp. 1-5; vol. 2; Wiley-VCH Verlag GmbH & Co. KGaA, Weinheim.

Mändle et al.; "Infection of human $CD34^+$ progenitor cells with *Bartonella henselae* results in intraerythrocytic presence of B henselae"; Blood; Aug. 15, 2005; pp. 1215-1222; vol. 106, No. 4; The American Society of Hematology.

Mitchell et al.; "Characterization of a Two-Gene Locus from *Bartonella bacilliformis* Associated with the Ability to Invade Human Erythrocytes"; Infection and Immunity; Apr. 1995; pp. 1552-1562; vol. 63, No. 4; American Society for Microbiology.

Montet-Abou et al.; "Transfection Agent Induced Nanoparticle Cell Loading"; Molecular Imaging; Jul. 2005; pp. 165-171; vol. 4, No. 3; Neoplasia Press, Inc.

Naglik et al.; "*Candida albicans* Secreted Aspartyl Proteinases in Virulence and Pathogenesis"; Microbiology and Molecular Biology Reviews; Sep. 2003; pp. 400-428; vol. 67, No. 3; American Society for Microbiology.

Nauenburg et al.; "Induction of apoptosis in cervical carcinoma cells by peptide aptamers that bind to the HPV-16 E7 oncoprotein[1]"; The FASEB Journal; Mar. 2001; pp. 592-594; vol. 15; FASEB.

Neildez-Nguyen et al.; "Human erythroid cells produced ex vivo at large scale differentiate into red blood cells in vivo"; Nature Biotechnology; May 2002; pp. 467-472; vol. 20; Nature Publishing Group.

Nicolini et al.; "Expression of a human β-globin transgene in erythroid cells derived from retrovirally transduced transplantable human fetal liver and cord blood cells"; Blood; Aug. 15, 2002; pp. 1257-1264; vol. 100, No. 4; The American Society of Hematology.

Nitin et al.; "Peptide-linked molecular beacons for efficient delivery and rapid mRNA detection in living cells"; Nucleic Acids Research; 2004; pp. 1-8; vol. 32, No. 6; Oxford University Press.

Noble et al.; "Reticulocytes. I. Isolation and In Vitro Maturation of Synchronized Populations"; Blood; Jul. 1989; pp. 475-481; vol. 74, No. 1; Grune & Stratton, Inc.

Oldak et al.; "Optimisation of transfection conditions of $CD34^+$ hematopoietic cells derived from human umbilical cord blood"; Acta Biochimica Polonica; 2002; pp. 625-632; vol. 49, No. 3.

Osten et al.; "Viral Vectors: A Wide Range of Choices and High Levels of Service"; HEP; 2007; pp. 177-202; vol. 178; Springer-Verlag Berlin Heidenberg 2007.

Papapetrou et al.; "Genetic modification of hematopoietic stem cells with nonviral systems: past progress and future prospects"; Gene Therapy; 2005; pp. S118-S130; vol. 12; Nature Publishing Group.

Pitassi et al.; "*Bartonella henselae* Infects Human Erythrocytes"; Ultrastructural Pathology; 2007; pp. 369-372; vol. 31; Informa Healthcare USA, Inc.

Proske et al.; "Aptamers-basic research, drug development, and clinical applications"; Applied Microbiology Biotechnology; 2005 pp. 367-374; vol. 69; Springer-Verlag 2005.

Reinholz et al.; "Evaluation of a Panel of Tumor Markers for Molecular Detection of Circulating Cancer Cells in Women with Suspected Breast Cancer"; Clinical Cancer Research; May 15, 2005; pp. 3722-3732; vol. 11, No. 10; American Association for Cancer Research.

Reiter et al.; "Prostate stem cell antigen: A cell surface marker overexpressed in prostate cancer"; The Proceedings of the National Academy of Sciences USA, Medical Sciences; Feb. 1998; pp. 1735-1740; vol. 95; The National Academy of Sciences.

Rolain et al.; "Culture and Antibiotic Susceptibility of *Bartonella quintana* in Human Erythrocytes"; Antimicrobial Agents and Chemotherapy; Feb. 2003; pp. 614-619; vol. 47, No. 2; American Society for Microbiology.

Samia et al.; "Invited Review, Quantum Dot-based Energy Transfer: Perspectives and Potential for Applications in Photodynamic Therapy"; Photochemistry and Photobiology; 2006; pp. 617-625; vol. 82; American Society for Photobiology.

Schülein et al.; "Invasion and Persistent Intracellular Colonization of Erythrocytes: A Unique Parasitic Strategy of the Emerging Pathogen *Bartonella*"; The Journal of Experimental Medicine; May 7, 2001; pp. 1077-1086; vol. 193, No. 9; The Rockefeller University Press.

Shangguan et al.; "Aptamers evolved from live cells as effective molecular probes for cancer study"; PNAS; Aug. 8, 2006; pp. 11838-11843; vol. 103, No. 32; The National Academy of Sciences of the USA.

Shin et al.; "Low molecular weight polyethylenimine for efficient transfection of human hematopoietic and umbilical cord blood-derived $CD34^+$ cells"; Biochimica et Biophysica Acta, BBA; 2005; pp. 377-384; vol. 1725; Elsevier B.V.

Skinner-Adams et al.; "Methodology, Comparison of *Plasmodium falciparum* transfection methods"; Malaria Journal; 2003; pp. 1-4; vol. 2, No. 19; Skinner-Adams et al.

Smith et al.; "Inactivation of *Plasmodium falciparum* by Photodynamic Excitation of Heme-Cycle Intermediates Derived from δ-Aminolevulinic Acid"; The Journal of Infectious Diseases; Jul. 1, 2004; pp. 184-191; vol. 190; The Infectious Diseases Society of America.

Song et al.; "Transduction of Tumor Necrosis Factor-Related Apoptosis-Inducing Ligand into Hematopoietic Cells Leads to Inhibition of Syngeneic Tumor Growth In vivo"; Cancer Research; Jun. 15, 2006; pp. 6304-6311; vol. 66, No. 12; American Association for Cancer Research.

Spear et al.; "Isolation, characterization, and recovery of small peptide phage display epitopes selected against viable malignant glioma cells"; Cancer Gene Therapy; 2001; pp. 506-511; vol. 8, No. 7; Nature Publishing Group.

Strauchen, MD, James A.; "Malignant Lymphomas: Cell Surface Markers and Advances in Classification"; The Western Journal of Medicine; Oct. 1981; pp. 276-284; vol. 135, No. 4.

Sun et al.; "Plasminogen Is a Critical Host Pathogenicity Factor for Group A Streptococcal Infection"; Science; Aug. 27, 2004; pp. 1283-1286; vol. 305.

Suzuki et al.; "Efficient Cytoplasmic Protein Delivery by Means of a Multifunctional Envelope-type Nano Device"; Biological Pharmaceutical Bulletin; 2007; pp. 758-762; vol. 30, No. 4; Pharmaceutical Society of Japan.

Swirski et al.; "A Near-Infrared Cell Tracker Reagent for Multiscopic In Vivo Imaging and Quantification of Leukocyte Immune Responses"; PLoS One; Oct. 2007; pp. 1-7; Issue 10; Swirski et al.

Tao et al.; "Enhanced Green Fluorescent Protein Is a Nearly Ideal Long-Term Expression Tracer for Hematopoietic Stem Cells, Whereas DsRed-Express Fluorescent Protein Is Not"; Stem Cells; 2007; pp. 670-678; vol. 25; AlphaMed Press.

Ulrich et al.; "In Vitro Selection of RNA Aptamers That Bind to Cell Adhesion Receptors of Trypanosoma cruzi and Inhibit Cell Invasion"; The Journal of Biological Chemistry; Jun. 7, 2002; pp. 20756-20762; vol. 277, No. 23; The American Society for Biochemistry and Molecular Biology, Inc.

Van Den Berg et al.; "Method of Isolating Erythrocytes Influences Their Measured Polyamine Content"; Clinical Chemistry; 1987; pp. 1081-1082; vol. 33, No. 6.

Van Tendeloo et al.; "Highly efficient gene delivery by mRNA electroporation in human hematopoietic cells: superiority to lipofection and passive pulsing of mRNA and to electroporation of plasmid cDNA for tumor antigen loading of dendritic cells"; Blood; Jul. 1, 2001; pp. 49-56; vol. 98, No. 1; The American Society of Hematology.

Vanderbyl et al.; "Transgene expression after stable transfer of a mammalian artificial chromosome into human hematopoietic cells"; Experimental Hematology; 2005; pp. 1470-1476; vol. 33; International Society for Experimental Hematology.

Verma et al.; "Gene transfer into human umbilical cord blood-derived CD34+ cells by particle-mediated gene transfer"; Gene Therapy; 1998; pp. 692-699; vol. 5; Stockton Press.

Wang et al.; "APD: the Antimicrobial Peptide Database"; Nucleic Acids Research; 2004; pp. D590-D592; vol. 32; Oxford University Press.

Wu et al.; "Efficient expression of foreign genes in human CD34+ hematopoietic precursor cells using electroporation"; Gene Therapy; 2001; pp. 384-390; vol. 8; Nature Publishing Group.

Wu et al.; "Transfection of Plasmodium falciparum within human red blood cells"; The Proceedings of the National Academy of Sciences USA, Genetics; Feb. 1995; pp. 973-977; vol. 92; Nature Publishing Group.

Xiang et al.; "Short hairpin RNA-expressing bacteria elicit RNA interference in mammals"; Nature Biotechnology; Jun. 2006; pp. 697-702; vol. 24, No. 6; Nature Publishing Group.

Zaitsev et al.; "Human complement receptor type 1-directed loading of tissue plasminogen activator on circulating erythrocytes for prophylactic fibrinolysis"; Blood; Sep. 15, 2006; pp. 1895-1902; vol. 108, No. 6; The American Society of Hematology.

Zheng et al.; "Photodynamic molecular beacon as an activatable photosensitizer based on protease-controlled singlet oxygen quenching and activation"; PNAS; May 22, 2007; pp. 8989-8994; vol. 104, No. 21; The National Academy of Sciences of the USA.

Forge, Andrew et al.; "Aminoglycoside Antibiotics"; Audiology & Neurotology; bearing a date of Jan./Feb. 2000; pp. 3-22; vol. 5, No. 1; S. Karger AG, Basel.

Kaestner, Lars et al.; "Erythrocytes—the 'house elves' of photodynamic therapy"; Photochem. Photobio. Sci.; Published on Oct. 26, 2004; vol. 3; pp. 981-989; The Royal Society of Chemistry and Owner Societies.

PCT International Search Report; Application No. PCT/US 2011/001365; Nov. 25, 2011; pp. 1-2.

Mygind et al.; "Plectasin is a peptide antibiotic with therapeutic potential from a saprophytic fungus"; Nature; Oct. 13, 2005; pp. 975-980; vol. 437; Nature Publishing Group.

BIOLOGICAL TARGETING COMPOSITIONS AND METHODS OF USING THE SAME

CROSS-REFERENCE TO RELATED APPLICATIONS

Related Applications

The present application is related to U.S. patent application Ser. No. 12/228,869, titled BIOLOGICAL TARGETING COMPOSITIONS AND METHODS OF USING THE SAME, naming Roderick A. Hyde, Muriel Y. Ishikawa, Edward K. Y. Jung, William Gates, Alois A. Langer, Eric C. Leuthardt, Royce A. Levien, Clarence T. Tegreene, Thomas A. Weaver, Charles Whitmer, Lowell L. Wood, Jr., and Victoria Y. H. Wood as inventors, filed 13, Aug. 2008, which is currently co-pending.

The present application is related to U.S. patent application Ser. No. 12/228,893, titled BIOLOGICAL TARGETING COMPOSITIONS AND METHODS OF USING THE SAME, naming Roderick A. Hyde, Muriel Y. Ishikawa, Edward K. Y. Jung, William Gates, Alois A. Langer, Eric C. Leuthardt, Royce A. Levien, Clarence T. Tegreene, Thomas A. Weaver, Charles Whitmer, Lowell L. Wood, Jr., and Victoria Y. H. Wood as inventors, filed 13, Aug. 2008, which is currently co-pending.

The present application is related to U.S. patent application Ser. No. 12/228,868, titled BIOLOGICAL TARGETING COMPOSITIONS AND METHODS OF USING THE SAME, naming Roderick A. Hyde, Muriel Y. Ishikawa, Edward K. Y. Jung, William Gates, Alois A. Langer, Eric C. Leuthardt, Royce A. Levien, Clarence T. Tegreene, Thomas A. Weaver, Charles Whitmer, Lowell L. Wood, Jr., and Victoria Y. H. Wood as inventors, filed 13, Aug. 2008, which is currently co-pending.

The present application is related to U.S. patent application Ser. No. 12/228,892, titled BIOLOGICAL TARGETING COMPOSITIONS AND METHODS OF USING THE SAME, naming Roderick A. Hyde, Muriel Y. Ishikawa, Edward K. Y. Jung, William Gates, Alois A. Langer, Eric C. Leuthardt, Royce A. Levien, Clarence T. Tegreene, Thomas A. Weaver, Charles Whitmer, Lowell L. Wood, Jr., and Victoria Y. H. Wood as inventors, filed 13, Aug. 2008, which is currently co-pending.

All subject matter of the Related Applications and of any and all parent, grandparent, great-grandparent, etc. applications of the Related Applications is incorporated herein by reference to the extent such subject matter is not inconsistent herewith.

SUMMARY

In one aspect, a modified red blood cell is described, which modified red blood cell comprises a red blood cell, one or more fusion molecules, and at least one target-binding agent comprising a target recognition moiety, wherein the target recognition moiety is designed to recognize one or more target cells, and wherein the one or more fusion molecules are designed to participate in fusion of the red blood cell with the target cell.

In an embodiment, the modified red blood cell is genetically engineered to express one or more of the at least one target-binding agent and the one or more fusion molecules. In an embodiment, the at least one target-binding agent and the one or more fusion molecules is associated with the cell surface of the red blood cell.

In an embodiment, the one or more fusion molecules includes, but is not limited to, at least one of: an antigen; ligand; receptor; polyamide; peptide; carbohydrate; oligosaccharide; polysaccharide; low density lipoprotein (LDL) or an apoprotein of LDL; steroid; steroid derivative; hormone; hormone-mimic; lectin; drug; antibiotic; aptamer; DNA; RNA; lipid; an antibody; and an antibody-related polypeptide. In an embodiment, the one or more fusion molecules is a syncytin-1 protein.

In an embodiment, the target recognition moiety includes, but is not limited to, at least one of: an antigen; ligand; receptor; polyamide; peptide; carbohydrate; oligosaccharide; polysaccharide; low density lipoprotein (LDL) or an apoprotein of LDL; steroid; steroid derivative; hormone; hormone-mimic; lectin; drug; antibiotic; aptamer; DNA; RNA; lipid; an antibody; and an antibody-related polypeptide.

In an embodiment, the modified red blood cell may include one or more activatable molecular markers associated with the red blood cell, wherein the one or more molecular markers is activated by the interaction of the red blood cell with the one or more target cells, and wherein the activated molecular markers are capable of producing a detectable response. For example, the one or more molecular markers is a photoactivatable molecule and the detectable response is the production of reactive singlet oxygen molecules. In an embodiment, the red blood cell may be genetically engineered to express the one or more molecular markers, e.g., an aptamer based molecular beacon.

In an embodiment, the at least one target-binding agent may include a photoactivatable molecule and a quencher molecule coupled to the target recognition moiety, wherein the target-binding agent emits at least one singlet oxygen radical molecule upon exposure to light of a suitable wavelength when the target-binding agent is bound to a target cell. In an embodiment, the photoactivatable molecule and the quenching molecule includes a linking component. In an embodiment, the linking component includes an oligonucleotide of about 20-60 residues or a linker to link with an amino or hydroxy fatty acid or a sulfonic acid of from 1 to 20 carbon atoms using an ester, an amide, or a sulfonamide linkage.

In an embodiment, the photoactivatable molecule includes, but is not limited to, at least one of a: porphyrin; chlorin; bacteriochlorin; isbacteriochlorin; phthalocyanine; napthalocyanine; porphycene; porphycyanine; tetra-macrocyclic compound; poly-macrocyclic compound; pyropheo-phorbide; pentaphyrin; sapphyrin; texaphyrin; metal complexe; tetrahydrochlorin; phonoxazine dye; phenothiazine; chaloorganapyrylium dye; rhodamine; fluorescene; azoporphyrin; benzochlorin; purpurin; chlorophyll; verdin; triarylmethane; angelicin; chalcogenapyrillium dye; chlorophyll; coumarin; cyanine; ceratin daunomycin; daunomycinone; 5-iminodauno-mycin; doxycycline; furosemide; gilvocarcin M; gilvocarcin V; hydroxy-chloroquine sulfate; lumidoxycycline; mefloquine hydrochloride; mequitazine; merbromin (mercurochrome); primaquine diphosphate; quinacrine dihydrochloride; quinine sulfate; tetracycline hydrochloride; flavins; alloxazine; flavin mononucleotide; 3-hydroxyflavone; limichrome; limiflavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin; metallo-porphyrin; metallophthalocyanine; methylene blue derivative; naphthalmide; naphthalocyanine; pheophorbide; pheophytin; photosensitizer dimer and conjugate; phthalocyanine; porphycene; quinone; retinoid; rhodamine; thiophene; verdin; vitamin; and xanthene dye.

In an embodiment, the quencher molecule includes, but is not limited to, at least one of: 4-(4'-dimethylamino-phenylazo)benzoic acid (DABCYL); dabcyl succinimidyl ester; 4-(4'-dimethylamino-phenylazo)sulfonic (DABSYL); dabsyl succinimidyl ester; tetramethyl-rhodamaine (TAMRA); 4-[(4-nitrophenyl)diazinyl]-phenylamine and 4-[4-nitrophenyl)diazinyl]-naphthylamine; dabcylnitro-thiazole; 6-(N-[7-nitrobenz-2-oxa-1,3-diazol-4-yl]amino) hexanoic acid; 6-carboxy-X-rhodamine (ROX); QSY-7; 2-[4-(4-nitrophenylazo)-N-ethylphenyl-amino]ethanol (Disperse Red 1); 2-[4-(2-chloro-4-nitrophenyl-azo)-N-ethylphenylamino]-ethanol (Disperse Red 13); tetrarhodamine isothiocyanate (TRITC); allophycocyanin; β-carotene; diarylrhodamine derivatives, QSY 7, QSY 9, QSY 21 dyes; QSY 35 acetic acid succinimidyl ester; QSY 35 iodoacetamide; aliphatic methylamine; napthalate; Reactive Red 4; and Malachite Green.

In an embodiment, the photoactivatable molecule may be linked to the quenching molecule and the target recognition moiety and configured so that the photoactivatable molecule is quenched until the target recognition moiety is bound to the target molecule, whereupon the quenching molecule moves away from the photoactivatable molecule, enabling detectable excitation of the photoactivatable molecule upon irradiation with the light of a suitable wavelength.

In an embodiment, the red blood cell includes, but is not limited to, at least one of: a reticulocyte; a red blood cell; and a fusion red blood cell including between a red blood cell autologous to a subject and one or more allogeneic erythrocytes, liposomes or artificial vesicles.

In an embodiment, the red blood cell may be genetically engineered to express one or more protein-based pharmaceuticals or one or more RNA-based pharmaceuticals. In an embodiment, the red blood cell may be loaded with one or more pharmaceutical or imaging molecules. In an embodiment, the pharmaceutical molecule includes, but is not limited to, at least one of: an antibiotic, an antiviral agent, an antifungal agent, an antimicrobial, a polypeptide, an antiparasitic agent, an antibody, an antibody-related polypeptide, an antineoplastic agent; a protein-based agent; and a nucleic acid-based agent. In an embodiment, the red blood cell may be loaded with biologically-active entities, such as for example, viruses and/or bacterium. Loaded viruses may be designed to infect a certain cellular target, and may be designed as vehicle for efficient gene delivery to a cellular target.

In an embodiment, the antineoplastic agent includes, but is not limited to, at least one of: an alkylating agent; cisplatin; carboplatin; oxaliplatin; mechlorethamine; cyclophosphamide; chlorambucil; anti-metabolite compound; azathioprine; mercaptopurine; alkaloid; terpenoid; vinca alkaloid; vincristine; vinblastine; vinorelbine; vindesine; podophyllotoxin; taxanes; docetaxel; paclitaxel; topoisomerase inhibitors; camptothecin; irinotecan; topotecan; amsacrine; etoposide; etoposide phosphate; teniposide; epipodophyllotoxins; antitumour antibiotics; dactinomycin; trastuzumab, cetuximab, rituximab; bevacizumab; finasteride; tamoxifen; gonadotropin-releasing hormone agonists (GnRH); and goserelin.

In an embodiment, the antibiotic includes, but is not limited to, at least one of: aminoglycoside; amikacin; gentamicin; kanamycin; neomycin; netilmicin; steptomycin; tobramycin; ansamycins; geldanamycin; herbimycin; carbacephem; loracarbef; carbacepenem; ertapenem; doripenem; imipenem/cilastatin; meropenem; cephalosporin; cefadroxil; cefazolin; cefalotin or cefalothin; cefalexin; cefaclor; cefamandole; cefoxitin; cefprozil; cefuroxime; cefixime; cefdinir; cefditoren; cefoperazone; cefotaxime; cefpodoxime; ceftazidime; ceftibuten; ceftizoxime; ceftriaxone; cefepime; ceftobiprole; glycopeptide; teicoplanin; vancomycin; macrolides; azithromycin; clarithromycin; dirithromycin; erythromicin; roxithromycin; troleandomycin; telithromycin; spectinomycin; monobactam; aztreonam; penicillins; amoxicillin; ampicillin; azlocillin; carbenicillin; cloxacillin; dicloxacillin; flucloxacillin; mezlocillin; meticillin; nafcillin; oxacillin; penicillin, piperacillin, ticarcillin; bacitracin; colistin; polymyxin B; quinolone; ciprofloxacin; enoxacin; gatifloxacin; levofloxacin; lomefloxacin; moxifloxacin; norfloxacin; ofloxacin; trovafloxacin; sulfonamide; mafenide; prontosil (archaic); sulfacetamide; sulfamethizole; sufanilimide (archaic); sulfasalazine; sulfisoxazole; trimethoprim; trimethoprim-sulfamethoxazole (co-trimoxazole) (TMP-SMX); tetracycline; demeclocycline; doxycycline; minocycline; oxytetracycline; tetracycline; arsphenamine; chloramphenicol; clindamycin; lincomycin; ethambutol; fosfomycin; fusidic acid; furazolidone; isoniazid; linezolid; metronidazole; mupirocin; nitrofuantoin; platensimycin; purazinamide; quinupristin/dalfopristin; rifampin or rifampicin; and tinidazole.

In an embodiment, the antiviral agent includes, but is not limited to, at least one of a: thiosemicarbazone; metisazone; nucleoside and/or nucleotide; acyclovir; idoxuridine; vidarabine; ribavirin; ganciclovir; famciclovir; valaciclovir; cidofovir; penciclovir; valganciclovir; brivudine; ribavirin, cyclic amines; rimantadine; tromantadine; phosphonic acid derivative; foscarnet; fosfonet; protease inhibitor; saquinavir; indinavir; ritonavir; nelfinavir; amprenavir; lopinavir; fosamprenavir; atazanavir; tipranavir; nucleoside and nucleotide reverse transcriptase inhibitor; zidovudine; didanosine; zalcitabine; stavudine; lamivudine; abacavir; tenofovir disoproxil; adefovir dipivoxil; emtricitabine; entecavir; non-nucleoside reverse transcriptase inhibitor; nevirapine; delavirdine; efavirenz; neuraminidase inhibitor; zanamivir; oseltamivir; moroxydine; inosine pranobex; pleconaril; and enfuvirtide.

In an embodiment, the anti-fungal agent includes, but is not limited to, at least one of a: allylamine; terbinafine; antimetabolite; flucytosine; azole; fluconazole; itraconazole; ketoconazole; ravuconazole; posaconazole; voriconazole; glucan synthesis inhibitor; caspofungin; micafungin; anidulafungin; polyenes; amphotericin B; amphotericin B Lipid Complex (ABLC); amphotericin B Colloidal Dispersion (ABCD); liposomal amphotericin B (L-AMB); liposomal nystatin; and griseofulvin.

In an embodiment, the anti-parasitic agent includes, but is not limited to, at least one of a: antiprotozoal agent; eflornithine; furazolidone; melarsoprol; metronidazole; ornidazole; paromomycin sulfate; pentamidine; pyrimethamine; tinidazole; antimalarial agent; quinine; chloroquine; amodiaquine; pyrimethamine; sulphadoxine; proguanil; mefloquine; halofantrine; primaquine; artemesinin and derivatives thereof; doxycycline; clindamycin; benznidazole; nifurtimox; antihelminthic; albendazole; diethylcarbamazine; mebendazole; niclosamide; ivermectin; suramin; thiabendazole; pyrantel pamoate; levamisole; piperazine family; praziquantel; triclabendazole; octadepsipeptide; and emodepside.

In an aspect, a pharmaceutical composition is described, the pharmaceutical composition comprising a modified red blood cell and a pharmaceutically acceptable excipient.

In an aspect, a method of treatment is described, the method comprising providing a modified red blood cell to a subject, the modified red blood cell comprising a red blood cell, one or more fusion molecules, and at least one target-binding agent comprising a target recognition moiety, wherein the target recognition moiety is configured to recognize one or more target cells including a neoplastic cell or a pathogen cell, and wherein the one or more fusion molecules are configured to participate in fusion of the red blood cell with the target cell.

In an embodiment, the modified red blood cell further comprises one or more activatable molecular markers associated with the red blood cell, wherein the one or more molecular markers are configured to be activated by the interaction of the red blood cell with the one or more target cells, and are configured to provide a detectable response upon excitation with electromagnetic energy.

In an embodiment, the method further comprises providing electromagnetic energy to the subject, the electromagnetic energy configured to induce a detectable response from the one or more activated molecular markers associated with the red blood cell; and detecting the response from the one or more activated molecular markers.

In an embodiment, the at least one target-binding agent further comprises a photoactivatable molecule and a quencher molecule coupled to the target recognition moiety, wherein the target-binding agent emits at least one singlet oxygen radical molecule upon exposure to light of a suitable wavelength when the target-binding agent is bound to a target cell.

In an embodiment, the method further comprises providing electromagnetic energy to a subject, the electromagnetic energy configured to activate the photoactivatable molecules, wherein activation of the photoactivatable molecule damages the target cells.

In an embodiment, activation of the one or more photoactivatable molecules directly damages the one or more target cells. In an embodiment, activation of the one or more photoactivatable molecules indirectly damages the one or more target cells.

In an embodiment, the neoplastic cell is associated with, but is not limited to, at least one of: ovarian cancer; bladder cancer; lung cancer; cervical cancer; breast cancer; prostate cancer; glioma; fibrosarcoma; retinoblastoma; melanoma; soft tissue sarcoma; ostersarcoma; leukemia; colon cancer; carcinoma of the kidney; gastrointestinal cancer; salivary gland cancer and pancreatic cancer.

In an embodiment, the pathogen cell includes, but is not limited to, at least one of: a bacteria; a fungi; a virus; and a parasite. In an embodiment, the bacteria includes, but is not limited to, at least one of: *Neisseria meningitides, Neisseria gonorrheoeae; Legionella; Vibrio cholerae; Streptococci; Staphylococcus aureus; Staphylococcus epidermidis; Pseudomonas aeruginosa; Corynobacteria diphtheriae, Clostridium* spp.; *Eschericia coli; Bacillus anthracis; Bartonella henselae; Bartonella quintana; Coxiella burnetii; Chlamydia; Mycobacterium leprae; Salmonella; Shigella; Yersinia enterocolitica; Yersinia pseudotuberculosis; Legionella pneumophila; Mycobacterium tuberculosis; Listeria monocytogenes; Mycoplasma* spp.; *Pseudomonas fluorescens; Vibrio cholerae; Haemophilus influenzae; Bacillus anthracis; Treponema pallidum; Leptospira; Borrelia; Corynebacterium diphtheriae; Francisell; Brucella melitensis; Campylobacter jejuni; Enterobacter; Proteus mirabilis; Proteus*; and *Klebsiella pneumoniae.*

In an embodiment, the fungi includes, but is not limited to, at least one of: *Candida albicans; Candida glabrata; Aspergilus* spp.; *Torulopsis glabrata; Candida tropicalis; C. krusei*; and *C. parapsilosis.*

In an embodiment, the virus includes, but is not limited to, at least one of: adenovirus; coxsackievirus; hepatitis a virus; poliovirus; epstein-barr virus; herpes simplex; type 1; herpes simplex; type 2; human cytomegalovirus; human herpesvirus; type 8; varicella-zoster virus; hepatitis B virus; hepatitis C viruses; human immunodeficiency virus (HIV); influenza virus; measles virus; mumps virus; parainfluenza virus; respiratory syncytial virus; papillomavirus; rabies virus; and Rubella virus.

In an embodiment, the parasite includes, but is not limited to, at least one of a: trypanosome; haemoprotozoa and parasites capable of causing malaria; enteric and systemic cestode; taeniid cestod; enteric coccidian; enteric flagellate protozoa; filarial nematode; gastrointestinal and systemic nematode and hookworm.

In an aspect, a method for detecting a target in a biological sample is described, the method comprising: (i) adding to the biological sample a modified red blood cell that binds to the target; and (ii) detecting the modified red blood cell wherein the modified red blood cell includes a red blood cell, one or more fusion molecules, and at least one target-binding agent comprising a target recognition moiety, wherein the target recognition moiety is designed to recognize one or more target cells, and wherein the one or more fusion molecules are designed to participate in fusion of the red blood cell with the target cell.

In an aspect, a method of making a modified red blood cell is described, the method comprising: providing a red blood cell; contacting the red blood cell with one or more fusion molecules and one or more target-binding agents comprising a target recognition moiety. Further, the modified red blood cell may be isolated from the one or more target-binding agent and the one or more fusion molecules which are not associated with the modified red blood cell, thereby making an isolated modified red blood cell.

In an embodiment, providing the red blood cell comprises differentiating erythrocytes ex vivo from a stem cell or a reticulocyte.

In an aspect, a modified red blood cell comprising a red blood cell and at least one target-binding agent comprising a target recognition moiety may be coupled to a photoactivatable molecule and a quencher molecule, wherein the target-binding agent emits at least one singlet oxygen radical molecule upon exposure to light of a suitable wavelength when the target-binding agent is bound to a target molecule.

In an embodiment, the at least one target-binding agent is configured to be associated with the cell surface of the red blood cell. In an embodiment, the at least one target-binding agent is configured to be internalized within the red blood cell.

In an embodiment, the photoactivatable molecule and the quenching molecule include a linking component. In an embodiment, the linking component is an oligonucleotide of about 20-60 residues or is a linker to link with an amino or hydroxy fatty acid or a sulfonic acid of from about 1 to 20 carbon atoms using an ester, amide, or sulfonamide linkage.

In an embodiment, the at least one target recognition moiety includes, but is not limited to, at least one of: an antigen; ligand; receptor; polyamide; peptide; carbohydrate; oligosaccharide; polysaccharide; low density lipoprotein (LDL) or an apoprotein of LDL; steroid; steroid derivative; hormone; hormone-mimic; lectin; drug; antibiotic; aptamer; DNA; RNA; lipid; an antibody; and an antibody-related polypeptide.

In an embodiment, the at least one photoactivatable molecule includes, but is not limited to, at least one of a: porphyrin; chlorin; bacteriochlorin; isbacteriochlorin; phthalocyanine; napthalocyanine; porphycene; porphycyanine; tetramacrocyclic compound; poly-macrocyclic compound; pyropheo-phorbide; pentaphyrin; sapphyrin; texaphyrin; metal complex; tetrahydrochlorin; phonoxazine dye; phenothiazine; chaloorganapyrylium dye; rhodamine; fluorescene; azoporphyrin; benzochlorin; purpurin; chlorophyll;

verdin; triarylmethane; angelicin; chalcogenapyrillium dye; chlorophyll; coumarin; cyanine; ceratin daunomycin; daunomycinone; 5-iminodauno-mycin; doxycycline; furosemide; gilvocarcin M; gilvocarcin V; hydroxy-chloroquine sulfate; lumidoxycycline; mefloquine hydrochloride; mequitazine; merbromin (mercurochrome); primaquine diphosphate; quinacrine dihydrochloride; quinine sulfate; tetracycline hydrochloride; flavins; alloxazine; flavin mononucleotide; 3-hydroxyflavone; limichrome; limiflavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin; metalloporphyrin; metallophthalocyanine; methylene blue derivative; naphthalmide; naphthalocyanine; pheophorbide; pheophytin; photosensitizer dimer and conjugate; phthalocyanine; porphycene; quinone; retinoid; rhodamine; thiophene; verdin; vitamin; and xanthene dye.

In an embodiment, the quencher molecule includes, but is not limited to, at least one of: 4-(4'-dimethylamino-phenylazo)benzoic acid (DABCYL); dabcyl succinimidyl ester; 4-(4'-dimethylamino-phenylazo)sulfonic (DABSYL); dabsyl succinimidyl ester; tetramethyl-rhodamaine (TAMRA); 4-[(4-nitrophenyl)diazinyl]-phenylamine and 4-[4-nitrophenyl)diazinyl]-naphthylamine; dabcylnitro-thiazole; 6-(N-[7-nitrobenz-2-oxa-1,3-diazol-4-yl]amino)hexanoic acid; 6-carboxy-X-rhodamine (ROX); QSY-7; 2-[4-(4-nitrophenylazo)-N-ethylphenyl-amino]ethanol (Disperse Red 1); 2-[4-(2-chloro-4-nitrophenyl-azo)-N-ethylphenylamino]-ethanol (Disperse Red 13); tetrarhodamine isothiocyanate (TRITC); allophycocyanin; β-carotene; diarylrhodamine derivatives, QSY 7, QSY 9, QSY 21 dyes; QSY 35 acetic acid succinimidyl ester; QSY 35 iodoacetamide; aliphatic methylamine; napthalate; Reactive Red 4; and Malachite Green.

In an embodiment, the red blood cell includes, but is not limited to, at least one of: a reticulocyte; a red blood cell; and a fused red blood cell including a red blood cell autologous to a subject fused to one or more allogeneic erythrocytes, liposomes or artificial vesicles.

In an embodiment, the at least one photoactivatable molecule is operably linked to the quenching molecule and the target recognition moiety so that the at least one photoactivatable molecule is quenched until the target recognition moiety is bound to the target molecule, whereupon the quenching molecule moves away from the photoactivatable molecule, enabling excitation of the photoactivatable molecule upon irradiation with the light of a suitable wavelength.

In an embodiment, the red blood cell further comprises at least one therapeutic agent. In an embodiment, the therapeutic agent includes, but is not limited to, at least one of: an antibiotic, an antiviral agent, an antifungal agent, an antiparasitic agent, an antibody, an antibody-related polypeptide, a chemotherapeutic agent; a protein-based pharmaceutical; and an RNA-based pharmaceutical. In an embodiment, the antibody is a monoclonal antibody, a polyclonal antibody, a fragment thereof, including but not limited to a ScFv fragment, or a Fab fragment, or antibody-like molecules.

In an embodiment, the red blood cell is engineered to further comprise one or more of another target recognition moiety including: an antigen; ligand; receptor; one member of a specific binding pair; polyamide; peptide; carbohydrate; oligosaccharide; polysaccharide; low density lipoprotein (LDL) or an apoprotein of LDL; steroid; steroid derivative; hormone; hormone-mimic; lectin; drug; antibiotic; aptamer; DNA; RNA; lipid; antibody; and an antibody-related polypeptide.

In an aspect, a method for administering a photodynamic therapy to a target is described, the method, comprising the steps of: (i) administering to a subject in need thereof, a modified red blood cell that preferentially associates with the target; and (ii) irradiating at least a portion of the subject with light of a wavelength and total fluence configured to produce a therapeutic effect.

In an embodiment, the target includes, but is not limited to, at least one of a vascular endothelial tissue; a neovasculature tissue; a neovasculature tissue present in an eye; an abnormal vascular wall of a tumor; a solid tumor; a tumor of a head; a tumor of a neck; a tumor of an eye; a tumor of a gastrointestinal tract; a tumor of a liver, a tumor of a breast; a tumor of a prostate; a tumors of a lung; a nonsolid tumor; malignant cells of one of a hematopoietic tissue, a lymphoid tissue, skin tissue; lesions in a vascular system, a diseased bone marrow; noncancerous hyperproliferative tissue; and diseased cells in which the disease is one of an autoimmune and an inflammatory disease.

In an embodiment, the target includes, but is not limited to, at least one of: a bacteria; a virus; a fungi; and a parasite.

In an embodiment, the parasite includes, but is not limited to, at least one of: trypanosomes; haemoprotozoa and parasites capable of causing malaria; enteric and systemic cestodes; taeniid cestodes; enteric coccidians; enteric flagellate protozoa; filarial nematodes; gastrointestinal and systemic nematodes and hookworms.

In an aspect, the use of a modified blood cell is described, wherein the use is in a treatment of a medical condition selected from the group consisting of: atherosclerosis; restenosis; cancer; cancer precurors; noncancerous hyperproliferative diseases; psoriasis; macular degeneration; glaucoma; viral infection; bacterial infection; fungal infection; and a parasitic infection.

In an aspect, a method for detecting a target in a biological sample is described, the method comprising: (i) adding to the biological sample the modified red blood cell that binds to the target; and (ii) detecting the modified red blood cell.

In an embodiment, the target includes, but is not limited to, at least one of a vascular endothelial tissue; a neovasculature tissue; a neovasculature tissue present in an eye; an abnormal vascular wall of a tumor; a solid tumor; a tumor of a head; a tumor of a neck; a tumor of an eye; a tumor of a gastrointestinal tract; a tumor of a liver, a tumor of a breast; a tumor of a prostate; a tumors of a lung; a nonsolid tumor; malignant cells of one of a hematopoietic tissue, a lymphoid tissue, skin tissue; lesions in a vascular system, a diseased bone marrow; noncancerous hyperproliferative tissue; and diseased cells in which the disease is one of an autoimmune and an inflammatory disease.

In an embodiment, the bacteria includes, but is not limited to, at least one of: *Neisseria meningitides; Neisseria gonorrheoeae; Legionella; Vibrio cholerae; Streptococci; Staphylococcus aureus; Staphylococcus epidermidis; Pseudomonas aeruginosa; Corynobacteria diphtheriae; Clostridium* spp.; *Eschericia coli; Bacillus anthracis; Bartonella henselae; Bartonella quintana; Coxiella burnetii; Chlamydia; Mycobacterium leprae; Salmonella; Shigella; Yersinia enterocolitica; Yersinia pseudotuberculosis; Legionella pneumophila; Mycobacterium tuberculosis; Listeria monocytogenes; Mycoplasma* spp.; *Pseudomonas fluorescens; Vibrio cholerae; Haemophilus influenzae; Bacillus anthracis; Treponema pallidum; Leptospira; Borrelia; Corynebacterium diphtheriae; Francisella; Brucella melitensis; Campylobacter jejuni; Enterobacter; Proteus mirabilis; Proteus;* and *Klebsiella pneumoniae.*

In an embodiment, the fungi includes, but is not limited to, at least one of: *Candida albicans; Candida glabrata; Aspergilus* spp.; *Torulopsis glabrata; Candida tropicalis; C. krusei;* and *C. parapsilosis.*

In an embodiment, the virus includes, but is not limited to, at least one of: adenovirus; coxsackievirus; hepatitis A virus; poliovirus; epstein-barr virus; herpes simplex type 1; herpes simplex type 2; human cytomegalovirus; human herpes virus type 8; varicella-zoster virus; hepatitis B virus; a hepatitis C virus; human immunodeficiency virus (HIV); influenza virus; measles virus; mumps virus; parainfluenza virus; respiratory syncytial virus; papillomavirus; rabies virus; and Rubella virus.

In an embodiment, the parasite includes, but is not limited to, at least one of trypanosomes; haemoprotozoa; parasites from the genus *Plasmodium*, including but not limited to, *Plasmodium falciparum, Plasmodium vivax, Plasmodium ovale, Plasmodium malaria*; enteric and systemic cestodes; taeniid cestodes; enteric coccidians; enteric flagellate protozoa; filarial nematodes; gastrointestinal and systemic nematodes and hookworms.

In an embodiment, the biological sample includes, but is not limited to, at least one of blood, urine, saliva, tears, synovial fluid, sweat, interstitial fluid, sperm, cerebrospinal fluid, ascites fluid, tumor tissue biopsy; tissue biopsy; and circulating tumor cells.

In an aspect, a method of generating an image of a target tissue or a modified red blood cell in a subject is described, the method comprising: (i) administering to the subject the modified red blood cell; and (ii) generating an image of at least a portion of the subject to which the modified red blood cell has preferentially associated.

In an aspect, a kit to treat a medical condition using a photodynamic therapy is described, the method comprising the modified red blood cell and instructions for providing photodynamic therapy. In an embodiment, the medical condition includes, but is not limited to, at least one of: atherosclerosis; restenosis; cancer; cancer precurors; noncancerous hyperproliferative diseases; psoriasis; macular degeneration; glaucoma; viruses; bacterial infection; fungal infection; and a parasitic infection.

In an aspect, a kit to specifically label a cell or tissue is described, the kit comprising: the modified red blood cell comprising at least one target recognition moiety directed to the specific cell or tissue; and instructions teaching a method of imaging the modified red blood cell.

In an aspect, a method of making an isolated modified red blood cell is described, the method comprising providing a red blood cell; contacting the red blood cell with a one or more target-binding agents comprising a target recognition moiety, a photoactivatable molecule, and a quencher molecule, under conditions wherein the one or more target-binding agent is associated with the red blood cell to produce a modified red blood cell; and isolating the modified red blood cell from the one or more target-binding agent which is not associated with the modified red blood cell, thereby making an isolated modified red blood cell.

In an embodiment, the step of providing the red blood cell comprises differentiating erythrocytes ex vivo from a stem cell or a reticulocyte. In an embodiment, the stem cells are hematopoietic stem cells. In an embodiment, the red blood cell is autologous to the subject. In an embodiment, the red blood cell may be allogeneic to the subject. In an embodiment, the allogeneic red blood cell includes one or more blood type specific erythrocytes or one or more universal donor erythrocytes. In an embodiment, the red blood cells are erythrocytes fused between erythrocytes autologous to the subject and one or more allogeneic erythrocytes, liposomes, or artificial vesicles. In an embodiment, the red blood cell may be engineered to produce a protein-based pharmaceutical or an RNA-based pharmaceutical.

In an embodiment, the method further comprises the step of loading the modified red blood cell with a therapeutic agent. In an embodiment, the therapeutic agent includes, but is not limited to, at least one of: an antibiotic, an antiviral agent, an antifungal agent, an anti-parasitic agent, an antibody, an antibody-related polypeptide; a chemotherapeutic agent; a protein-based pharmaceutical; and an RNA-based pharmaceutical.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
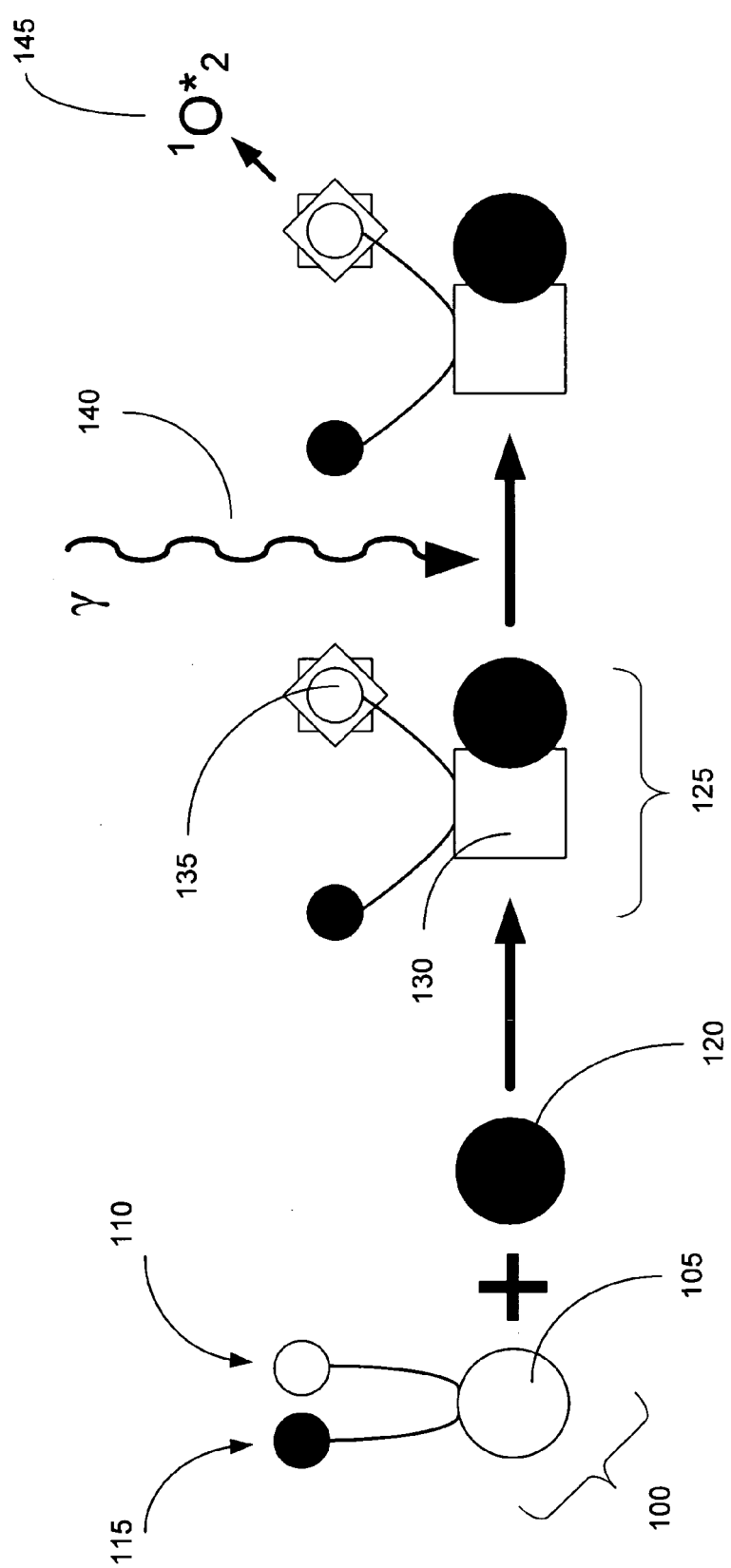
FIG. 1 is a schematic diagram illustrating the activation of a target-binding agent upon binding to a target molecule and exposure to light of a suitable wavelength and power.

Described herein are modified red blood cells. More particularly described herein are compositions comprising a red blood cell associated with a target recognition moiety and a fusion protein. In an embodiment, the modified red blood cell may comprise a photoactivatable molecule and a quencher molecule, wherein the target-binding agent emits at least one singlet oxygen radical molecule upon exposure to electromagnetic radiation (e.g., light) of a suitable wavelength when the target-binding agent is bound to a target molecule. Also described are targeted delivery of imaging agents, drugs, and peptide and protein pharmaceuticals using modified red blood cells. Processes for preparing the modified red blood cells, pharmaceutical and diagnostic compositions containing the same and methods of diagnosis and treatment involving the modified red blood cells are described. The specific compositions and methods described herein are intended as merely illustrative of their more general counterparts.

In this disclosure, many conventional techniques in molecular biology, protein biochemistry, cell biology, immunology, microbiology and recombinant DNA are described or referenced. These techniques are well-known and are explained in, e.g., *Current Protocols in Molecular Biology*, Vols. I-III, Ausubel, Ed. (1997); Sambrook et al., *Molecular Cloning. A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonuchotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively. and Strachan & Read, *Human Molecular Genetics*, Second Edition. (John Wiley and Sons, Inc., NY, 1999)).

As used in this specification and the appended claims, the singular forms "a," "an" and "the" include plural referents unless the content clearly dictates otherwise. For example, reference to "a cell" include a single cell or may include a combination of two or more cells, and the like. Generally, the nomenclature used herein and the laboratory procedures in cell culture, molecular genetics, organic chemistry, analytical chemistry and nucleic acid chemistry and hybridization described below are those well known and commonly employed in the art.

Units, prefixes, and symbols may be denoted in their accepted SI form. Unless otherwise indicated, nucleic acids are written left to right in 5' to 3' orientation; amino acid sequences are written left to right in amino to carboxy orientation. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes.

All references cited herein are incorporated herein by reference to the extent not inconsistent with the instant disclosure and for all purposes to the same extent as if each individual publication, patent, or patent application was specifically and individually incorporated by reference.

The administration of an agent or drug to a subject or subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another.

An antibody includes a polypeptide comprising a framework region from an immunoglobulin gene or fragments thereof that specifically binds and recognizes an antigen. Use of the term antibody is meant to include whole antibodies, including single-chain antibodies, antibody fragments, and antibody-related polypeptides. Antibody includes bispecific antibodies and multispecific antibodies so long as they exhibit the desired biological activity or function.

An antibody-related polypeptide includes antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included are any combinations of variable region(s) and hinge region, $CH_1$, $CH_2$, and $CH_3$ domains. Antibody-related molecules useful as binding agents include, e.g., but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., *Nature* 341: 544-546 (1989)), which consists of a $V_H$ domain; and (vi) an isolated complementarity determining region (CDR). As such antibody fragments may comprise a portion of a full length antibody, generally the antigen binding or variable region thereof. Examples of antibody fragments include, but are not limited to, Fab, Fab', F(ab')$_2$, and Fv fragments; diabodies; linear antibodies; single-chain antibody molecules; and multispecific antibodies formed from antibody fragments. Single-chain antibody molecules may comprise a polymer with a number of individual molecules, for example, dimmer, trimer or other polymers.

A biological sample includes sample material derived from or contacted by living cells. The term "biological sample" is intended to include tissues, cells and biological fluids isolated from a subject, as well as tissues, cells and fluids present within a subject. Biological samples include, e.g., but are not limited to, whole blood, plasma, semen, saliva, tears, urine, fecal material, sweat, buccal, skin, cerebrospinal fluid, and hair. Biological samples can also be obtained from biopsies of internal organs or from cancers. Biological samples can be obtained from subjects for diagnosis or research or can be obtained from undiseased individuals, as controls or for basic research.

A antineoplastic agent includes a chemical compound that can be used effectively to treat a neoplastic cell.

An effective amount or pharmaceutically effective amount or therapeutically effective amount of a composition, includes a quantity of material sufficient to reasonably achieve a desired therapeutic and/or prophylactic effect. For example, it may include an amount that results in the prevention of, treatment of, or a decrease in, the symptoms associated with a disease or condition that is being treated, e.g., the diseases or medical conditions associated with a target polypeptide. The amount of a therapeutic composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

Electromagnetic radiation of a suitable wavelength includes one or more frequencies of electromagnetic radiation having one or more characteristics that taken as a whole are not considered unduly harmful to the subject. In illustrative non-limiting examples, such electromagnetic energy may include frequencies of optical light, optionally including visible light (detected by the human eye between approximately 400 nm and 700 nm) as well as infrared (longer than 700 nm) and limited spectral regions of ultraviolet light, such as UVA light (between approximately 320 nm and 400 nm). Electromagnetic energy includes, but is not limited to, single photon electromagnetic energy, two photon electromagnetic energy, multiple wavelength electromagnetic energy, and extended-spectrum electromagnetic energy.

An epitope includes any segment on an antigen to which an antibody or other ligand or binding molecule binds. An epitope may consist of chemically active surface groupings of molecules such as amino acids or sugar side chains and usually have specific three dimensional structural characteristics, as well as specific charge characteristics.

A monoclonal antibody includes an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone, and not the method by which it is produced. A monoclonal antibody composition displays a single binding specificity and affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

A non-target tissue includes tissue of the subject which are not intended to be impaired or destroyed by the treatment method. These non-target tissues include but are not limited to healthy blood cells, and other normal tissue, not otherwise identified to be targeted.

A photoactivatable molecule or photosensitizing agent includes a chemical compound that upon exposure to photoactivating electromagnetic radiation is activated to release a singlet oxygen molecule. In an embodiment, the photoactivatable molecule itself, or some other species, is converted into a cytotoxic form, whereby target cells are killed or their proliferative potential diminished. Thus, photoactivatable molecule may exert their effects by a variety of mechanisms, directly or indirectly. For example, certain photoactivatable molecules become toxic when activated by light, for example by generating toxic species, e.g., oxidizing agents such as singlet oxygen or oxygen-derived free radicals, which are extremely destructive to cellular material and biomolecules such as lipids, proteins and nucleic acids. Porphyrins are of photosensitizing agents that act by generation of toxic oxygen species. Typically, the chemical compound is nontoxic to the animal to which it is administered or is capable of being formulated in a nontoxic composition, and the chemical compound in its photodegraded form is also nontoxic. A listing of representative photosensitive chemicals may be found in Kreimer-Bimbaum, Sem. Hematol. 26:157-73 (1989).

A quencher, quencher molecule, or quenching molecule includes a moiety capable of preventing activation of the photoactivatable molecule when the target-binding agent is not bound to the target. Alternatively, the quencher may be capable of preventing the release of singlet oxygen from the target-binding agent when the target-binding agent is not bound to the target. In a suitable embodiment, the photoactivatable molecule is a porphyrin, and the quencher includes one or more suitable functional groups that coordinate to the axial position of the metal coordinated within the photoactivatable molecule. The target recognition moiety is positioned in the agent in such a way that the interaction of the target recognition moiety with the target disrupts the association of the axial ligand to the metal, releasing the quenching agent and allowing the porphyrin or porphyrin derivative tetrapyrrole to be activated when irradiated.

A subject includes, but is not limited to, a mammal, such as a human, but can also be an animal, e.g., domestic animals (e.g., dogs, cats and the like), farm animals (e.g., cows, sheep, pigs, horses and the like) and laboratory animals (e.g., monkey, rats, mice, rabbits, guinea pigs and the like).

A target includes the object that is intended to be detected, diagnosed, impaired or destroyed by the methods provided herein, and includes target cells, target tissues, and target compositions. Target cells are cells in target tissue, and the target tissue includes, but is not limited to, vascular endothelial tissue, abnormal vascular walls of tumors, solid tumors such as (but not limited to) tumors of the head and neck, tumors of the eye, tumors of the gastrointestinal tract, tumors of the liver, tumors of the breast, tumors of the prostate, tumors of the lung, nonsolid tumors and malignant cells of the hematopoietic and lymphoid tissue, neovascular tissue, other lesions in the vascular system, bone marrow, and tissue or cells related to autoimmune disease. Also included among target cells are cells undergoing substantially more rapid division as compared to non target cells, as well as pathogens such as bacteria, fungi, viruses, and parasites.

A target recognition moiety includes a molecule that is configured to specifically bind with a target. In an embodiment, the target recognition moiety is a member of a specific binding pair, e.g., an antigen; ligand; receptor; polyamide; peptide; carbohydrate; oligosaccharide; polysaccharide; low density lipoprotein (LDL) or an apoprotein of LDL; steroid; steroid derivative; hormone; hormone-mimic; lectin; drug; antibiotic; aptamer; DNA; RNA; lipid; or an antibody or antibody-related polypeptide.

A therapeutic agent includes a compound or molecule that, when present in an effective amount, produces a desired therapeutic effect on a subject in need thereof.

Compositions

In an aspect, modified red blood cells are described that are configured to target specific cells or tissues. In an embodiment, the modified red blood cells comprise at least one target-binding agent including a target recognition moiety and one or more fusion molecules. The modified red blood cells may be used as a vehicle to deliver myriad agents to targets in vivo. In an embodiment, the modified red blood cells include a photoactivatable molecule that is activated upon binding of a target recognition moiety to a target molecule. When the photoactivatable molecule is exposed to photoactivating light, one or more singlet oxygen radical molecules is produced, which may kill or damage target cells or tissues directly or indirectly. In this section, the components of the modified red blood cells are described.

I. Preparation of Modified Red Blood Cells

A. Preparation of Red Blood Cells

1. Isolation of Red Blood Cells

Mature red blood cells for use in generating the modified red blood cells may be isolated using various methods such as, for example, a cell washer, a continuous flow cell separator, density gradient separation, fluorescence-activated cell sorting (FACS), Miltenyi immunomagnetic depletion (MACS), or a combination of these methods (See, e.g., van der Berg et al., *Clin. Chem.* 33:1081-1082 (1987); Bar-Zvi et al., *J. Biol. Chem.* 262:17719-17723 (1987); Goodman et al., *Exp. Biol. Med.* 232:1470-1476 (2007)).

Red blood cells may be isolated from whole blood by simple centrifugation (See, e.g., van der Berg et al., *Clin. Chem.* 33:1081-1082 (1987)). For example, EDTA-anticoagulated whole blood may be centrifuged at 800×g for 10 min at 4° C. The platelet-rich plasma and buffy coat are removed and the red blood cells are washed three times with isotonic saline solution (NaCl, 9 g/L).

Alternatively, red blood cells may be isolated using density gradient centrifugation with various separation mediums such as, for example, Ficoll, Hypaque, Histopaque, Percoll, Sigmacell, or combinations thereof. For example, a volume of Histopaque-1077 is layered on top of an equal volume of Histopaque-1119. EDTA-anticoagulated whole blood diluted 1:1 in an equal volume of isotonic saline solution (NaCl, 9 g/L) is layered on top of the Histopaque and the sample is centrifuged at 700×g for 30 min at room temperature. Under these conditions, granulocytes migrate to the 1077/1119 interface, lymphocytes, other mononuclear cells and platelets remain at the plasma/1077 interface, and the red blood cells are pelleted. The red blood cells are washed twice with isotonic saline solution.

Alternatively, red blood cells may be isolated by centrifugation using a Percoll step gradient (See, e.g., Bar-Zvi et al., *J. Biol. Chem.* 262:17719-17723 (1987)). As such, fresh blood is mixed with an anticoagulant solution containing 75 mM sodium citrate and 38 mM citric acid and the cells washed briefly in Hepes-buffered saline. Leukocytes and platelets are removed by adsorption with a mixture of α-cellulose and Sigmacell (1:1). The red blood cells are further isolated from reticulocytes and residual white blood cells by centrifugation through a 45/75% Percoll step gradient for 10 min at 2500 rpm in a Sorvall SS34 rotor. The red blood cells are recovered in the pellet while reticulocytes band at the 45/75% interface and the remaining white blood cells band at the 0/45% interface. The Percoll is removed from the red blood cells by several washes in Hepes-buffered saline. Other materials that may be used to generate density gradients for isolation of red blood cells include OptiPrep™, a 60% solution of iodixanol in water (from Axis-Shield, Dundee, Scotland).

Red blood cells may be separated from reticulocytes, for example, using flow cytometry (See, e.g., Goodman el al., *Exp. Biol. Med.* 232:1470-1476 (2007)). In this instance, whole blood is centrifuged (550×g, 20 min, 25° C.) to separate cells from plasma. The cell pellet is resuspended in phosphate buffered saline solution and further fractionated on Ficoll-Paque (1.077 density), for example, by centrifugation (400×g, 30 min, 25° C.) to separate the red blood cells from the white blood cells. The resulting cell pellet is resuspended in RPMI supplemented with 10% fetal bovine serum and sorted on a FACS instrument such as, for example, a Becton Dickinson FACSCalibur (BD Biosciences, Franklin Lakes, N.J., USA) based on size and granularity.

Red blood cells may be isolated by immunomagnetic depletion (See, e.g., Goodman, el al., (2007) Exp. Biol. Med. 232:1470-1476). In this instance, magnetic beads with cell-type specific antibodies are used to eliminate non-red blood cells. For example, red blood cells are isolated from the majority of other blood components using a density gradient as described above followed by immunomagnetic depletion of any residual reticulocytes. The cells are pre-treated with human antibody serum for 20 min at 25° C. and then treated antibodies against reticulocyte specific antigens such as, for example, CD71 and CD36. The antibodies may be directly attached to magnetic beads or conjugated to PE, for example, to which magnetic beads with anti-PE antibody will react. As such, the antibody-magnetic bead complex is able to selectively extract residual reticulocytes, for example, from the red blood cell population.

Red blood cells may also be isolated using apheresis. The process of apheresis involves removal of whole blood from a patient or donor, separation of blood components using centrifugation or cell sorting, withdrawal of one or more of the separated portions, and transfusion of remaining components back into the patient or donor. A number of instruments are currently in use for this purpose such as for example the Amicus and Alyx instruments from Baxter (Deerfield, Ill., USA), the Trima Accel instrument from Gambro BCT (Lakewood, Colo., USA), and the MCS+9000 instrument from Haemonetics (Braintree, Mass., USA). Additional purification methods, such as those described above, may be necessary to achieve the appropriate degree of red blood cell purity.

2. Allogenic and Autologous Modified Red Blood Cells

In an embodiment, the modified red blood cells are autologous and/or allogeneic to the subject. In an embodiment, erythrocytes allogeneic to the subject include one or more of one or more blood type specific erythrocytes or one or more universal donor erythrocytes. In an embodiment, the modified red blood cells are fusion erythrocytes between erythrocytes autologous to the subject and one or more allogeneic erythrocytes, liposomes, and/or artificial vesicles.

For autologous transfusion, red blood cells, reticulocytes or hematopoietic stem cells from an individual are isolated and modified by methods described herein and retransfused into the individual.

For allogeneic transfusions, red blood cells, reticulocytes or hematopoietic stem cells are isolated from a donor, modified by methods described herein and transfused into another individual. In the instance where allogeneic cells are used for transfusion, care needs to be taken to use a compatible ABO blood group to prevent an acute intravascular hemolytic transfusion reaction. The latter is characterized by complement activation and lysis of incompatible red blood cells. The ABO blood types are defined based on the presence or absence of the blood type antigens A and B, monosaccharide carbohydrate structures that are found at the termini of oligosaccharide chains associated with glycoproteins and glycolipids on the surface of the red blood cells (reviewed in Liu et al., *Nat. Biotech.* 25:454-464 (2007)). Group O red blood cells lack either of these antigenic monosaccharide structures.

Individuals with group A red blood cells have naturally occurring antibodies to group B red blood cells whereas individuals with group B red blood cells have antibodies to group A red blood cells. Blood group AB individuals have neither antibody and blood group O individuals have both. Individuals with either anti-A and/or anti-B antibodies cannot receive a transfusion of blood containing the corresponding antigen. Because group O red blood cells contain neither A nor B antigens, they can be safely transfused into recipients of any ABO blood group, i.e., group A, B, AB, or O recipients. As such, group O red blood cells are considered "universal" and may be used in all blood transfusions. In contrast, group A red blood cells may be given to group A and AB recipients, group B red blood cells may be given to group B and AB recipients, and group AB red blood cells may only be given to AB recipients. As such, the modified red blood cells with an activatable molecular marker are matched for compatibility with the recipient.

In some instances, it may be beneficial to convert a non-group O modified red blood cell to a universal blood type. Enzymatic removal of the immunodominant monosaccharides on the surface of group A and group B red blood cells is one approach to generating a group O-like red blood cell population (See, e.g., Liu et al., Nat. Biotech. 25:454-464 (2007)). Group B red blood cells may be converted using an α-galactosidase derived from green coffee beans, for example. Alternatively, α-N-acetylgalactosaminidase and α-galactosidase enzymatic activities derived from E. meningosepticum bacteria may be used to respectively remove the immunodominant A and B antigens (Liu et al., Nat. Biotech. 25:454-464 (2007)). As such, packed red blood cells isolated as described above, are incubated in 200 mM glycine (pH 6.8) and 3 mM NaCl in the presence of either α-N-acetylgalactosaminidase and α-galactosidase (~300 µg/ml packed red blood cells) for 60 min at 26° C. After treatment, the red blood cells are washed by 3-4 rinses in saline with centrifugation and ABO-typed according to standard blood banking techniques.

3. Derivation of Erythrocytes from Reticulocytes

In an embodiment, the red blood cells are differentiated ex vivo and/or in vivo from one or more reticulocytes. Modified reticulocytes may be used to generate mature red blood cells with monitoring and/or therapeutic properties. Reticulocytes are immature red blood cells and compose approximately 1% of the red blood cells in the human body. Reticulocytes develop and mature in the bone marrow. Once released into circulation, reticulocytes rapidly undergo terminal differentiation to mature red blood cells. Like mature red blood cells, reticulocytes do not have a cell nucleus. Unlike mature red blood cells, reticulocytes maintain the ability to perform protein synthesis. As such, the introduction of foreign messenger RNA (mRNA) into reticulocytes may facilitate synthesis and expression of exogenous proteins and/or peptides.

Reticulocytes of varying age may be isolated from peripheral blood based on the differences in cell density as the reticulocytes mature. As such, reticulocytes may be isolated from peripheral blood using differential centrifugation through various density gradients. For example, Percoll gradients may be used to isolate reticulocytes (See, e.g., Noble el al., Blood 74:475-481 (1989)). Sterile isotonic Percoll solutions of density 1.096 and 1.058 g/ml are made by diluting Percoll (Sigma-Aldrich, Saint Louis, Mo., USA) to a final concentration of 10 mM triethanolamine, 117 mM NaCl, 5 mM glucose, and 1.5 mg/ml bovine serum albumin (BSA). These solutions have an osmolarity between 295 and 310 mOsm. Five milliliters, for example, of the first Percoll solution (density 1.096) is added to a sterile 15 ml conical centrifuge tube. Two milliliters, for example, of the second Percoll solution (density 1.058) is layered over the higher density first Percoll solution. Two to four milliliters of whole blood are layered on top of the tube. The tube is centrifuged at 250×g for 30 min in a refrigerated centrifuge with swing-out tube holders. Reticulocytes and some white cells migrate to the interface between the two Percoll layers. The cells at the interface are transferred to a new tube and washed twice with phosphate buffered saline (PBS) with 5 mM glucose, 0.03 mM sodium azide and 1 mg/ml BSA. Residual white blood cells are removed by chromatography in PBS over a size exclusion column.

Alternatively, reticulocytes may be isolated by positive selection using an immunomagnetic separation approach (See, e.g., Brun et al., Blood 76:2397-2403 (1990)). This approach takes advantage of the large number of transferrin receptors that are expressed on the surface of reticulocytes relative to erythrocytes prior to maturation. As such, magnetic beads coated with an antibody to the transferrin receptor may be used to selectively isolate reticulocytes from a mixed red cell population. Antibodies to the transferrin receptor of a variety of mammalian species, including human, are available from commercial sources (e.g., Affinity BioReagents, Golden, Colo., USA; Sigma-Aldrich, Saint Louis, Mo., USA). The transferrin antibody may be directly linked to the magnetic beads. Alternatively, the transferrin antibody may be indirectly linked to the magnetic beads via a secondary antibody. For example, mouse monoclonal antibody 10D2 (Affinity BioReagents, Golden, Colo., USA) against human transferrin may be mixed with immunomagnetic beads coated with a sheep anti-mouse immunoglobulin G (Dynal/Invitrogen, Carlsbad, Calif., USA). The immunomagnetic beads are then incubated with a leukocyte-depleted red blood cell (RBC) fraction. The beads and RBCs are incubated at 22° C. with gentle mixing for 60-90 min followed by isolation of the beads with attached reticulocytes using a magnetic field. The isolated reticulocytes may be removed from the magnetic beads using, for example, DETACHaBEAD® solution (from Invitrogen, Carlsbad, Calif., USA). Alternatively, reticulocytes may be isolated from in vitro growth and maturation of CD34+ hematopoietic stem cells using the methods described below.

In general, the purity of the isolated reticulocytes may be assessed using microscopy in that reticulocytes are characterized by a reticular (mesh-like) network of ribosomal RNA that becomes visible under a microscope with certain stains such as new methylene blue or brilliant cresyl blue. Alternatively, analysis of creatine and hemoglobin $A_{1C}$ content and pyruvate kinase, aspartate aminotransferase, and porphobilinogen deaminase enzyme activity may be used to assess properties of the isolated reticulocytes relative to mature erythrocytes (See, e.g., Brun et al., Blood 76:2397-2403 (1990)). For example, the activity of porphobilinogen deaminase is nearly 9 fold higher whereas the hemoglobin $A_{1C}$ content is nearly 10 fold less in reticulocytes relative to mature erythrocytes.

Modified reticulocytes may be transfused into an animal and allowed to differentiate into mature erythrocytes in vivo. Alternatively, modified reticulocytes may be differentiated into mature erythrocytes in vitro prior to transfusion. Maturation of reticulocytes in vitro may be carried out over several days using standard cell culture methods (See, e.g., Noble et al., Blood 74:475-481 (1998)). For example, isolated reticulocytes are cultured for 3-5 days at 37° C. in Alpha-minimum essential medium (MEM) supplemented with 25 mM HEPES, 20 mg/dL glucose, 5% fetal bovine serum, 100 U/ml penicillin, and 0.1 mg/ml streptomycin, pH 7.5 at which time several assays may be done to assess maturation. For example, new methylene blue staining in combination with microscopy may be used to assess decline in the RNA-derived reticular network. Alternatively, the decline in the transferrin receptor expression as a function of maturation may be monitored using transferrin labeled, for example, with $^{125}$I, or FITC (Noble et al., *Blood* 74:475-481 (1998)). In some instances, the analysis of creatine and hemoglobin $A_{1C}$ content and pyruvate kinase, aspartate aminotransferase, and porphobilinogen deaminase enzyme activity may be used to assess maturation as described herein.

4. Differentiation of Red Blood Cells from Hematopoeitic Stem Cells

In an embodiment, the red blood cells are differentiated ex vivo and/or in vivo from one or more stem cells. In an embodiment, the one or more stem cells are one or more hematopoietic stem cells.

Red blood cells for use in generating a one or more modified red blood cells may be derived from hematopoietic stem cells. Hematopoietic stem cells give rise to all of the blood cell types found in mammalian blood including myeloid (monocytes and macrophages, neutorphils, basophils, eosinophils, erythrocytes, megakaryocytes/platelets, dendritic cells) and lymphoid lineages (T-cells, B-cells, NK-cells). Hematopoietic stem cells may be isolated from the bone marrow of adult bones including, for example, femur, hip, rib, or sternum bones. Cells may be obtained directly from the hip, for example, by removal of cells from the bone marrow using aspiration with a needle and syringe. Alternatively, hematopoietic stem cells may be isolated from normal peripheral blood following pre-treatment with cytokines such as, for example, granulocyte colony stimulating factor (G-CSF). G-CSF mobilizes the release of cells from the bone marrow compartment into the peripheral circulation. Other sources of hematopoietic stem cells include umbilical cord blood and placenta.

Isolated hematopoietic stem cells may be cultured, expanded and differentiated ex vivo. For example, hematopoietic stem cells isolated from bone marrow, cytokine-stimulated peripheral blood or umbilical cord blood may be expanded and differentiated ex vivo into mature erythrocytes (Giarratana et al., *Nature Biotech.* 23:69-74 (2005); U.S. Patent Application 2007/0218552). As such, CD34+ cells are isolated from bone marrow or peripheral or cord blood using, for example, magnetic microbead selection and Mini-MACS columns (Miltenyi Biotech). The cells are subsequently cultured in modified serum-free medium supplemented with 1% bovine serum albumin (BSA), 120 µg/ml iron-saturated human transferrin, 900 ng/ml ferrous sulfate, 90 ng/ml ferric nitrate and 10 µg/ml insulin and maintained at 37° C. in 5% carbon dioxide in air. Expansion and differentiation of the cell culture may occur in multiple steps. For example, in the initial growth step following isolation, the cells may be expanded in the medium described herein in the presence of multiple growth factors including, for example, hydrocortisone, stem cell factor, IL-3, and erythropoietin. In the second stage, the cells may be co-cultured, for example, on an adherent stromal layer in the presence of erythropoietin. In a third stage, the cells may be cultured on an adherent stromal layer in culture medium in the absence of exogenous factors. The adherent stromal layer may be murine MS-5 stromal cells, for example. Alternatively, the adherent stromal layer may be mesenchymal stromal cells derived from adult bone marrow. The adherent stromal cells may be maintained in RPMI supplemented with 10% fetal calf serum, for example.

In some instances, it may be desirable to expand and partially differentiate the CD34+ hematopoietic stem cells in vitro and to allow terminal differentiation into mature erythrocytes to occur in vivo (See, e.g., Neildez-Nguyen et al., *Nature Biotech.* 20:467-472 (2002)). As such, isolated CD34+ hematopoietic stem cells may be expanded in vitro in the absence of the adherent stromal cell layer in medium containing various factors including, for example, Flt3 ligand, stem cell factor, thrombopoietin, erythropoietin, and insulin growth factor. The resulting erythroid precursor cells, as judged by surface expression of CD36 and GPA, may be transfused into an animal where upon terminal differentiation to mature erythrocytes is allowed to occur.

Various assays may be performed to confirm the ex vivo differentiation of cultured hematopoietic stem cells into reticulocytes and erythrocytes, including, for example, microscopy, hematology, flow cytometry, deformability measurements, enzyme activities, and hemoglobin analysis and functional properties (Giarratana et al., *Nature Biotech.* 23:69-74 (2005)). The phenotype of cultured hematopoietic stem cells may be assessed using microscopy of cells stained, for example, with Cresyl Brilliant blue. Reticulocytes, for example, exhibit a reticular network of ribosomal RNA under these staining conditions whereas erythrocytes are devoid of staining. Enucleated cells may also be monitored for standard hematological variables including mean corpuscular volume (MCV; fl), mean corpuscular hemoglobin concentration (MCHC; %) and mean corpuscular hemoglobin (MCH; pg/cell) using, for example, an XE2100 automat (Sysmex, Roche Diagnostics).

For the deformability measurements, for example, presumptive reticulocytes may be separated from nucleated cells on day 15 of culture, for example, by passage through a deleukocyting filter (e.g., Leucolab LCG2, Macopharma) and subsequently assayed using ektacytometry. As such, the enucleated cells are suspended in 4% polyvinylpyrrolidone solution and then exposed to an increasing osmotic gradient from 60 to 450 mosM, for example. Changes in the laser diffraction pattern (deformability index) of the cells are recorded as a function of osmolarity, to assess the dynamic deformability of the cell membrane. The maximum deformability index achieved at a physiologically relevant osmolarity is related to the mean surface area of red blood cells.

Alternatively, assays of hemoglobin may be used to assess the phenotype of differentiated cells (Giarratana et al., *Nature Biotech.* 23:69-74 (2005)). For example, high performance liquid chromatography (HPLC) using a Bio-Rad Variant II Hb analyzer (Bio-Rad Laboratories) may be used to assess the percentage of various hemoglobin fractions. Oxygen equilibrium may be measured using a continuous method with a double-wavelength spectrophotometer (e.g., Hemox analyzer, TCS). The binding properties of hemoglobin may be assessed using flash photolysis. In this method, the rebinding of CO to intracellular hemoglobin tetramers are analyzed at 436 nm after photolysis with a 10 nanosecond pulse at 532 nm.

B. Target Recognition Moieties

The target-binding agents typically include one or more target recognition moieties for the selective binding of the composition to a target molecule. The target recognition moiety is configured to specifically bind to a target molecule of a particular cell, tissue, receptor, infecting agent or an area of the body of the subject to be treated, such as a target cell, target tissue or target composition.

Examples of target recognition moieties include, but are not limited to, an antigen; ligand; receptor; one member of a specific binding pair; polyamide; peptide; carbohydrate; oligosaccharide; polysaccharide; low density lipoprotein (LDL) or an apoprotein of LDL; steroid; steroid derivative; hormone; hormone-mimic; lectin; drug; antibiotic; aptamer; DNA; RNA; lipid; an antibody; and an antibody-related polypeptide. In particular embodiments, the target recognition moiety is an antibody or antibody-related polypeptide. For example, antibodies useful as target recognition moieties include antibodies in general and monoclonal antibodies. The target recognition moiety can include a polypeptide having an affinity for a polysaccharide target, for example, a lectin (such as a seed, bean, root, bark, seaweed, fungal, bacterial, or invertebrate lectin). Particularly useful lectins include concanavalin A, which is obtained from jack beans, and lectins obtained from the lentil, Lens culinaris. The target recognition moiety can be a molecule or a macromolecular structure (e.g., a liposome, a micelle, a lipid vesicle, or the like) that preferentially associates or binds to a particular tissue, receptor, infecting agent or other area of the body of the subject to be treated.

All such targeting methods are contemplated herein for use in the instant target-binding agents. For non-limiting examples of targeting methods, See, e.g., U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542 and 5,709,874.

1. Antibodies as Target Recognition Moieties

Antibodies most ideal for use in subjects are those that are non-immunogenic when administered to the subject. Such antibodies have the advantages of exerting minimal side-effects, having long serum and biologic half-life, having wide bio-distribution, having high target specificity and high activity in engaging the effector phase of the immune system. These antibodies, when intended for human subjects, are commonly referred to as "humanized," "human," "chimeric," or "primatized" antibodies; these are substantially (>70%) homologous to human amino acid sequences.

The target recognition moiety may be an antibody or an antigen binding antibody fragment configured to specifically bind to at least one epitope on the target molecule(s) associated with, produced by or on the surface of a target cell or tissue. The antibody or antibody fragment may be monospecific or multispecific. Both polyclonal and monoclonal antibodies may be used, as well as certain recombinant antibodies, such as chimeric and humanized antibodies and fusion proteins.

The target recognition moiety may be univalent, multivalent and/or multispecific. By "multivalent" it is meant that the target recognition moiety may bind more than one target, which may have the same or a different structure, simultaneously. By "multispecific" it is meant that the subject agents may bind to at least two targets which are of different structure. For example, a target recognition moiety having two different specificities would be considered multivalent and multispecific because it can bind two structurally different targets.

In some instances, the targeting antibody may be part of a multispecific antibody complex with one or more components that bind directly to a specific protein on the surface of the target cell (See, e.g., U.S. Pat. Nos. 5,470,570 and 5,843,440; U.S. Patent Applications 2003/0215454 A1 and 2006/0018912 A1). For example, the targeting antibody may be associated with a second antibody, such as a red blood cell binding antibody, that recognizes a protein on the surface of the red blood cell, e.g., α-N-acetylgalactosaminyltransferase, complement C4, aquaporin, complement decay-accelerating factor, band3 anion transport protein, Duffy antigen, glycophorin A, B and/or C, galactoside 2-L-fucosyltransferase 1, galactoside 2-L-fucosyltransferase 2, galactoside 3(4)-L-fucosyltransferase, CD44, Kell blood group glycoprotein, urea transporter, complement receptor protein (CR1), membrane transport protein XK, Landsteiner-Wiener blood group glycoprotein, Lutheran blood group glycoprotein, blood group RH (CE) polypeptide, blood group RH (D) polypeptide, Xg glycoprotein, acetylcholinesterase, anion exchanger, and/or insulin receptor (See, e.g., U.S. Patent Application 2006/0018912 A1). These multispecific antibodies are useful for the assembly of the modified red blood cells.

The antibodies within the multispecific antibody complex may be two or more intact antibodies and/or two or more antibody fragments such as, for example, Fab', F(ab')$_2$ and/or F$_v$ that are linked in some way to one another. The two or more antibodies may be fused by chemical conjugation, crosslinking and/or linker moieties. For example, polypeptides may be covalently bonded to one another through functional groups associated with the polypeptides such as, for example, carboxylic acid or free amine groups.

Alternatively, two or more antibodies may be linked through disulfide bonds. For example, the targeting antibody is reacted with N-succinimidyl S-acetylthioacetate (SATA) and subsequently deprotected by treatment with hydroxylamine to generate an SH-antibody with free sulfhydryl groups (See, e.g., U.S. Patent Application 2003/0215454 A1). The red blood cell binding antibody is reacted with sulfosuccinimidyl 4-(N-maelimidomethyl)cyclohexane-1-carboxylate (sSMCC). The two antibodies treated as such are purified by gel filtration and then reacted with one another to form a bispecific antibody complex.

Alternatively, the antibodies may be chemically cross-linked to form a heteropolymerized complex using, for example, SPDP [N-succinimidyl-3-(2-pyridyldithio)propionate] (See, e.g., Liu el al., *Proc. Nat'l Acad. Sci. USA* 82:8648-8652 (1985); U.S. Pat. No. 5,470,570). To generate the complex, the targeting antibody (1-2 mg/ml), for example, is incubated with a 7-fold molar excess of SPDP in phosphate buffered saline (PBS) for 45 minutes at room temperature. Excess SPDP is removed by dialysis overnight against two changes of PBS. Thiol groups are attached to the red blood cell binding antibody, for example, by incubating the antibody (1-3 mg/ml) with a 1000-fold molar excess of 2-iminothiolane in 12.5 mM sodium borate/PBS for 45 min at room temperature. Excess 2-iminothiolane is removed by dialysis as above. Equimolar amounts of the modified antibodies are incubated for 7 h at room temperature and the resulting heteropolymerized complex is separated from the uncoupled antibodies based on molecular weight using a standard sizing column.

Fab' fragments from one or more antibodies may be generated, mixed together, and naturally occurring disulfide linkages reformed by oxidation. As such, a subset of the products will contain a Fab' fragment from each antibody. Alternatively, Fab' fragments from the targeting antibody, for example, may be activated with a bis-maleimide linker such as 1,1'-(methylenedi-4,1-phenylene)bis-maleimide and then linked to the Fab' fragments from the red blood cell binding antibody through a disulfide bond (See, e.g., U.S. Patent Application 2003/0215454 A1).

Alternatively, the two antibody binding activities may be incorporated into a single fusion protein using recombinant DNA approaches (See, e.g., U.S. Pat. No. 6,132,992). For example, cDNA encoding the variable regions ($V_L$ and $V_H$) of two antibodies directed against separate and distinct antigens, for example, may be combined into a linear expression construct from which a bispecific single-chain antibody may be produced (See, e.g., Haisma el al., *Cancer Gene Ther.* 7:901-904 (2000)). As such, cDNA encoding the variable regions ($V_L$ and $V_H$) of the targeting antibody and of the red blood cell binding antibody, for example, may be manipulated to form a bispecific single-chain antibody.

C. Photoactivatable Molecules

In an embodiment, the target-binding agents may include one or more photoactivatable molecules, such as a photosensitizer. Typically, the photoactivatable molecule becomes activated upon exposure to electromagnetic radiation. Various photoactivatable molecules are useful over the wavelength range of about 350 to about 1300 nm, the exact range being dependent upon the particular photosensitizer. In suitable embodiments, photoactivatable molecules are those useful in the range of about 650-1000 nm (i.e., in the near infrared ("NIR")). For example, pyropheophorbide and bacteriochloin are useful in about the 650-900 nm range.

A photoactivatable molecule is a chemical compound that upon exposure to photoactivating light is activated, releasing a singlet oxygen species. The photoactivatable molecules of the target-binding agents disclosed herein can be any of the variety of synthetic and naturally occurring photosensitizing agents known in the art, including but not limited to, porphyrins; chlorins; bacteriochlorins; isbacteriochlorins; phthalocyanines; napthalocyanines; porphycenes; porphycyanines; tetra-macrocyclic compounds; poly-macrocyclic compounds; pyropheo-phorbides; pentaphyrin; sapphyrins; texaphyrins; metal complexes; tetrahydrochlorins; phonoxazine dyes; phenothiazines; chaloorganapyrylium dyes; rhodamines; fluorescenes; azoporphyrins; benzochlorins; purpurins; chlorophylls; verdins; triarylmethanes; angelicins; chalcogenapyrillium dyes; chlorins; chlorophylls; coumarins; cyanines; ceratin daunomycin; daunomycinone; 5-iminodauno-mycin; doxycycline; furosemide; gilvocarcin M; gilvocarcin V; hydroxy-chloroquine sulfate; lumidoxycycline; mefloquine hydrochloride; mequitazine; merbromin (mercurochrome); primaquine diphosphate; quinacrine dihydrochloride; quinine sulfate; and tetracycline hydrochloride; certain flavins and related compounds such as alloxazine; flavin mononucleotide; 3-hydroxyflavone; limichrome; limiflavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin; metallo-porphyrins; metallophthalocyanines; methylene blue derivatives; naphthalmides; naphthalocyanines; pheophorbides; pheophytins; photosensitizer dimers and conjugates; phthalocyanines; porphycenes; quinones; retinoids; rhodamines; thiophenes; verdins; vitamins; and xanthene dyes. Generally, any polypyrrolic macrocyclic photosensitive compound that is hydrophobic can be used.

The release of reactive oxygen species, such as singlet oxygen, may disrupt active cellular metabolism and cause photodamage by apoptosis. Some photoactivatable molecules, such as phthalocyanines have been shown to cause necrosis by a metabolism-independent mechanism (See, e.g., Prasad, *Introduction to Biophotonics*, John Wiley & Sons, Inc. Hoboken, N.J. (2003)). Oxidative degradation of membrane lipids can produce loss of membrane integrity resulting in impairment of membrane transport, rupturing of membrane, increased permeability, and crosslinking/inactivation of membrane associated polypeptides such as receptors, enzymes and ion channels. Chlorin, benzoporphyrin, and some phthalocyanine photosensitizers have been shown to cause damage to lysosomes. (See, e.g., Prasad, *Introduction to Biophotonics*, John Wiley & Sons, Inc. Hoboken, N.J. (2003))

Photoexcitation of the photoactivatable molecules by linear absorption (as opposed to excitation by a nonlinear, two-photon absorption) does not require a high peak power or a coherent light source. As such, tungsten and/or mercury or xenon arc lamps may be used to activate the photoactivatable molecules. Alternatively, lasers may be used for this purpose. Examples include a dye laser with rhodamine B as lasing medium and pumped by an argon-ion laser or an intracavity KTP-doubled Nd:Vanadate laser, both producing a CW dye laser output in the range of 1-4 W. Alternatively, pulse laser sources providing high repetition rates in the kilohertz range may be used and include gold vapor lasers, copper-pumped dye lasers, and quasi-CW Q-switched Nd:YAG laser-pumped dye lasers. In some instances, a solid-state diode laser may be used with CW and quasi-CW powers in the range of 1-4 W with a single emitter source in the range of 780-850 nm. Other laser sources include tunable solid-state lasers such a the Ti:sapphire laser (690-1100 nm) and the Alexandrite lasers (720-800 nm) (See, e.g., Prasad, *Introduction to Biophotonics*, John Wiley & Sons, Inc. Hoboken, N.J. (2003)).

The photoactivatable molecule itself may be monitored by quantitative fluorometry or reflectance spectophotometry. Activation of the photoactivatable molecules may be assessed by measuring singlet oxygen production at about 1270 nm (See, e.g., Lee et al., "Optical Methods for Tumor Treatment and Detection: Mechanisms and Techniques in Photodynamic therapy," XV Biomedical Optics (BiOS) Symposium, San Jose, Calif. (2006)).

A modified red blood cell may be loaded with a photosensitive reagent such as, for example, a derivative of hematoporphyrin and subsequently irradiated to release a therapeutic agent (See, e.g., Flynn et al., *Cancer Lett.* 82:225-229 (1994)). For example, modified red blood cells are suspended in a physiological buffer such as Ringer's Lactate Solution or saline solution with 5% dextrose (w/v) to which is added hematoporphyrin at a concentration of about 250 µg/ml. The cell suspension is incubated at 4° C. for 90 min and subsequently washed with the physiological buffer. The cells may be loaded with a therapeutic agent before, after, or concomitant with hematophorphyrin loading. The modified red blood cells may be irradiated with a 10 mW output HeNe laser, for example, to induce disruption of modified red blood cells and release of the therapeutic agent (See, e.g., Flynn et al., *Cancer Lett.* 82:225-229 (1994)).

Examples of some classes of photoactivatable molecules include, but are not limited to, angelicins, chalcogenapyrillium dyes, chlorins, chlorophylls, coumarins, cyanines, ceratin daunomycin; daunomycinone; 5-iminodauno-mycin; doxycycline; furosemide; gilvocarcin M; gilvocarcin V; hydroxy-chloroquine sulfate; lumidoxycycline; mefloquine hydrochloride; mequitazine; merbromin (mercurochrome); primaquine diphosphate; quinacrine dihydrochloride; quinine sulfate; and tetracycline hydrochloride, certain flavins and related compounds such as alloxazine; flavin mononucleotide; 3-hydroxyflavone; limichrome; limiflavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin, metallo-porphyrins, metallophthalocyanines, methylene blue derivatives, naphthalmides, naphthalocyanines, pheophorbides, pheophytins, photosensitizer dimers and conjugates, phthalocyanines, porphycenes, porphyrins, psoralens, purpurins, quinones, retinoids, rhodamines, thiophenes, verdins, vitamins and xanthene dyes (Redmond and Gamlin, *Photochem. Photobiol.*, 70(4):391-475 (1999)).

1. Porphyrins

Examples of porphyrins include 5-azaprotoporphyrin dimethylester; bis-porphyrin; coproporphyrin III; coproporphyrin III tetramethylester; deuteroporphyrin; deuteroporphyrin IX dimethylester; diformyldeutero-porphyrin IX dimethylester; dodecaphenylporphyrin; hematoporphyrin; hematoporphyrin; hematoporphyrin; hematoporphyrin; hematoporphyrin; hematoporphyrin; hematoporphyrin; hematoporphyrin; hematoporphyrin IX; hematoporphyrin monomer; hematoporphyrin dimer; hematoporphyrin derivative; hematoporphyrin derivative; hematoporphyrin derivative; hematoporphyrin derivative A; hematoporphyrin IX dihydrochloride; hematoporphyrin dihydrochloride; hematoporphyrin IX dimethylester; haematoporphyrin IX dimethylester; mesoporphyrin dimethylester; mesoporphyrin IX dimethylester; monoformyl-monovinyl-deuteroporphyrin IX dimethylester; monohydroxyethylvinyl deuteroporphyrin; 5,10,15,20-tetra(o-hydroxyphenyl)porphyrin; 5,10,15,20-tetra(m-hydroxyphenyl)porphyrin; 5,10,15,20-tetrakis-(m-hydroxyphenyl)-porphyrin; 5,10,15,20-tetra(p-hydroxyphenyl) porphyrin; 5,10,15,20-tetrakis(3-methoxyphenyl)-porphyrin; 5,10,15,20-tetrakis(3,4-dimethoxyphenyl) porphyrin; 5,10,15,20-tetrakis(3,5-dimethoxyphenyl) porphyrin; 5,10,15,20-tetrakis(3,4,5-trimethoxyphenyl) porphyrin; 2,3,7,8,12,13,17,18-octaethyl-5,10,15,20-tetraphenylporphyrin; Photofrin®; Photofrin II; porphyrin c; protoporphyrin; protoporphyrin IX; protoporphyrin dimethylester; protoporphyrin IX dimethylester, protoporphyrin propylaminoethylformamide iodide; protoporphyrin N,N-dimethylaminopropyl-formamide; protoporphyrin propylaminopropylformamide iodide; protoporphyrin butylformamide; protoporphyrin N,N-dimethylamino-formamide; protoporphyrin formamide; sapphyrin 13,12,13,22-tetraethyl-2,7,18,23 tetramethyl sapphyrin-8,17-dipropanol; sapphyrin 23,12,13,22-tetraethyl-2,7,18,23 tetramethyl sapphyrin-8-monoglycoside; sapphyrin 3; meso-tetra-(4-N-carboxyphenyl)-porphine; tetra-(3-methoxyphenyl)-porphine; tetra-(3-methoxy-2,4-difluorophenyl)-porphine; 5,10,15,20-tetrakis(4-N-methylpyridyl)porphine; meso-tetra-(4-N-methylpyridyl)-porphine tetrachloride; meso-tetra(4-N-methylpyridyl)-porphine; meso-tetra-(3-N-methylpyridyl)-porphine; meso-tetra-(2-N-methylpyridyl)-porphine; tetra(4-N,N,N-trimethylanilinium)porphine; meso-tetra-(4-N,N,N"-trimethylamino-phenyl)porphine tetrachloride; tetranaphthaloporphyrin; 5,10,15,20-tetraphenylporphyrin; tetraphenylporphyrin; meso-tetra-(4-N-sulfonatophenyl)-porphine; tetraphenylporphine tetrasulfonate; meso-tetra(4-sulfonatophenyl)-porphine; tetra(4-sulfonatophenyl)porphine; tetraphenylporphyrin sulfonate; meso-tetra(4-sulfonatophenyl)porphine; tetrakis(4-sulfonatophenyl) porphyrin; meso-tetra(4-sulfonatophenyl)porphine; meso(4-sulfonatophenyl)porphine; meso-tetra(4-sulfonatophenyl) porphine; tetrakis(4-sulfonatophenyl)porphyrin; meso-tetra (4-N-trimethylanilinium)-porphine; uroporphyrin; uroporphyrin 1; uroporphyrin IX; and uroporphyrin I.

2. Metalloporphyrins

Examples of metalloporphyrins include cobalt meso-tetra-(4-N-methylpyridyl)-porphine; cobalt (II) meso(4-sulfonatophenyl)-porphine; copper hematoporphyrin; copper meso-tetra-(4-N-methylpyridyl)-porphine; copper (II) meso (4-sulfonatophenyl)-porphine; Europium (III) dimethyltexaphyrin dihydroxide; gallium tetraphenylporphyrin; iron meso-tetra(4-N-methylpyridyl)-porphine; lutetium (III) tetra (N-methyl-3-pyridyl)-porphyrin chloride; magnesium (II) meso-diphenyl tetrabenzoporphyrin; magnesium tetrabenzoporphyrin; magnesium tetraphenylporphyrin; magnesium (II) meso(4-sulfonatophenyl)-porphine; magnesium (II) texaphyrin hydroxide metalloporphyrin; magnesium meso-tetra-(4-N-methylpyridyl)-porphine; manganese meso-tetra-(4-N-methyl-pyridyl)-porphine; nickel meso-tetra(4-N-methylpyridyl)-porphine; nickel (II) meso-tetra(4-sulfonatophenyl)-porphine; palladium (II) meso-tetra-(4-N-methylpyridyl)-porphine; palladium meso-tetra-(4-N-methylpyridyl)-porphine; palladium tetraphenylporphyrin; palladium (II) meso(4-sulfonatophenyl)-porphine; platinum (II) meso(4-sulfonatophenyl)-porphine; samarium (II) dimethyltexaphyrin dihydroxide; silver (II) meso(4-sulfonatophenyl)-porphine; tin (IV) protoporphyrin; tin meso-tetra-(4-N-methylpyridyl)-porphine; tin meso-tetra(4-sulfonatophenyl)-porphine; tin (IV) tetrakis(4-sulfonatophenyl) porphyrin dichloride; cadmium (II) chlorotexaphyrin nitrate; cadmium (II) meso-diphenyl tetrabenzoporphyrin; cadmium meso-tetra-(4-N-methylpyridyl)-porphine; cadmium (II) texaphyrin; cadmium (II) texaphyrin nitrate; zinc (II) 15-aza-3,7,12,18-tetramethyl-porphyrinato-13,17-diyl-dipropionic acid-dimethylester; zinc (II) chlorotexaphyrin chloride; zinc coproporphyrin III; zinc (II) 2,11,20,30-tetra-(1,1-dimethyl-ethyl)tetranaphtho(2,3-b:2',3'-g:2"3"-1:-2"'3"'-q)porphyrazine; zinc (II) 2-(3)-pyridyloxy) benzo[b]-10,19,28-tri(1,1-dimethylethyl)trinaphtho[2',3'-g:2"3"1::2"',3"'-q]porphyrazine; zinc (II) 2,18-bis-(3-pyridyloxy)dibenzo[b, 1]-10,26-di(1,1-dimethyl-ethyl)dinaphtho-[2',3'-g:2"',3"'-q]porphyrazine; zinc (II) 2,9-bis-(3-pyridyloxy)dibenzo[b,g]-17,26-di(1,1-dimethyl-ethyl)dinaphto[-2",3"-1:2"',3"'-q]porphyrazine; zinc (II) 2,9,16-tris-(3-pyridyloxy)tribenzo[b,g,1]-24=(1,1-dimethyl-ethyl) naphtho[2"',3"'-q]porphyrazine; zinc (II) 2,3-bis-(3-pyridyloxy)benzo[b]-10,19,28-tri(1,1-dimethyl-ethyl) trinaphtho-[2',3'-g:2",3"1:2"',3"'-q]porphyrazine; zinc (II) 2,3,18,19-tetrakis-(3-pyridyloxy)dibenzo[b,1]-10,26-di(1,1-dimethyl-ethyl-)trinaphtho[2',3'-g:2"',3"'-q]porphyrazine; zinc (II) 2,3,9,10-tetrakis-(3-pyridyloxy)dibenzo[b,g]-17,26-di(1,1-dimethyl-ethyl)-dinaphto[2",3"-1:2"',3"'-q]porphyrazine; zinc (II) 2,3,9,10,16,17-hexakis-(3-pyridyloxy) tribenzo[b,g, 1]-24(1,1-dimethyl-ethy-l)naphto[2"',3"'-q] porphyrazine; zinc (II) 2-(3-N-methyl)pyridyloxy)benzo[b]-10,19,28-tri(1,1-dimethyl-ethyl)trinaph-tho[2',3'-g:2",3"1:2"',3"'-q]porphyrazine monoiodide; zinc (II) 2,18-bis-(3-(N-methyl)pyridyloxy)dibenzo[b,1]-10,26-di(1,1-dimethylethyl)-dinaphtho[2',3'-g:2"',3"'-q]porphyrazine diiodide; zinc (II) 2,9-bis-(3-(N-methyl)pyridyloxy)dibenzo [b,g]-17,26-di(1,1-dimethylethyl)d-inaphtho[2",3"-1:2"',3"'-q]porphyrazine diiodide; zinc (II) 2,9,16-tris-(3-(N-methyl-pyridyloxy)tribenzo[b,g,1]-24-(1,1-dimethylethyl) naphtho[2"',3"'-q]porphyrazine triiodide; zinc (II) 2,3-bis-(3-(N-methyl)pyridyloxy)benzo[b]-10,19,28-tri(1,1-dimethylethyl)t-rinaphtho[2',3'-g:2",3"-1:2"',3"'-q] porphyrazine diiodide; zinc (II) 2,3,18,19-tetrakis-(3-(N-methyl)pyridyloxy)dibenzo[b,1]-10,26-di(1,1-dimethyl) dinaphtho[2',3'-g:2"',3"'-q]porphyrazine tetraiodide; zinc (II) 2,3,9,10-tetrakis-(3-(N-methyl)pyridyloxy)dibenzo[g,g]-17,26-di(1,1-dimethylethyl)dinaphtho[2",341-1:2"',3"'-q]porphyrazine tetraiodide; zinc (II) 2,3,9,10,16,17-hexakis-(3-(N-methyl)pyridyloxy)tribenzo[b,g,1]-24-(1-,1-dimethylethyl)naphtho[2"',3"'-q]porphyrazine hexaiodide; zinc (II) meso-diphenyl tetrabenzoporphyrin; zinc (II) meso-triphenyl tetrabenzoporphyrin; zinc (II) meso-tetrakis(2,6-dichloro-3-sulfonatophenyl)porphyrin; zinc (II) meso-tetra-(4-N-methylpyridyl)-porphine; zinc (II) 5,10,15,20-meso-tetra(4-octyl-phenylpropynyl)-porphine; zinc porphyrin c; zinc protoporphyrin; zinc protoporphyrin IX; zinc (II) meso-triphenyl-tetrabenzoporphyrin; zinc tetrabenzoporphyrin; zinc (II) tetrabenzoporphyrin; zinc tetranaphthaloporphyrin; zinc tetraphenylporphyrin; zinc (II) 5,10,15,20-tetraphenylporphyrin; zinc (II) meso (4-sulfonatophenyl)-porphine; and zinc (II) texaphyrin chloride.

3. Pheophorbides

Examples of pheophorbides include pheophorbide a; methyl 13-1-deoxy-20-formyl-7,8-vic-dihydro-bacterio-meso-pheophorbide a; methyl-2-(1-dodecyloxyethyl)-2-devinyl-pyropheophorbide a; methyl-2-(1-heptyl-oxyethyl)-2-devinyl-pyropheophorbide a; methyl-2-(1-hexyl-oxyethyl)-2-devinyl-pyropheophorbide a; methyl-2-(1-methoxy-ethyl)-2-devinyl-pyropheophorbide a; methyl-2-(1-pentyl-oxyethyl)-2-devinyl-pyropheophorbide a; magnesium methyl bacteriopheophorbide d; methyl-bacteriopheophorbide d; and pheophorbide.

4. Psoralens

Examples of psoralens include psoralen; 5-methoxypsoralen; 8-methoxy-psoralen; 5,8-dimethoxypsoralen; 3-carbethoxypsoralen; 3-carbethoxy-pseudopsoralen; 8-hydroxypsoralen; pseudopsoralen; 4,5',8-trimethyl-psoralen; allopsoralen; 3-aceto-allopsoralen; 4,7-dimethyl-allopsoralen; 4,7,4'-trimethyl-allopsoralen; 4,7,5'-trimethyl-allopsoralen; isopseudopsoralen; 3-acetoisopseudopsoralen; 4,5'-dimethyl-isopseudo-psoralen; 5',7-dimethyl-isopseudopsoralen; pseudoisopsoralen; 3-aceto-pseudoisopsoralen; 3/4',5'-trimethyl-aza-psoralen; 4,4',8-trimethyl-5'-amino-methylpsoralen; 4,4',8-trimethyl-phthalamyl-psoralen; 4,5',8-trimethyl-4'-aminomethyl psoralen; 4,5',8-trimethyl-bromopsoralen; 5-nitro-8-methoxy-psoralen; 5'-acetyl4,8-dimethyl-psoralen; 5'-aceto-8-methyl-psoralen; and 5'-aceto-4,8-dimethyl-psoralen. Examples of purpurins include octaethylpurpurin; octaethylpurpurin zinc; oxidized octaethylpurpurin; reduced octaethylpurpurin; reduced octaethylpurpurin tin; purpurin 18; purpurin-18; purpurin-18-methyl ester; purpurin; tin ethyl etiopurpurin I; Zn(II) aetio-purpurin ethyl ester; and zinc etiopurpurin.

5. Quinones

Examples of quinones include 1-amino-4,5-dimethoxy anthraquinone; 1,5-diamino-4,8-dimethoxy anthraquinone; 1,8-diamino-4,5-dimethoxy anthraquinone; 2,5-diamino-1,8-dihydroxy anthraquinone; 2,7-diamino-1,8-dihydroxy anthraquinone; 4,5-diamino-1,8-dihydroxy anthraquinone; mono-methylated 4,5- or 2,7-diamino-1,8-dihydroxy anthraquinone; anthralin (keto form); anthralin; anthralin anion; 1,8-dihydroxy anthraquinone; 1,8-dihydroxy anthraquinone (Chrysazin); 1,2-dihydroxy anthraquinone; 1,2-dihydroxy anthraquinone (Alizarin); 1,4-dihydroxy anthraquinone (Quinizarin); 2,6-dihydroxy anthraquinone; 2,6-dihydroxy anthraquinone (Anthraflavin); 1-hydroxy anthraquinone (Erythroxy-anthraquinone); 2-hydroxy-anthraquinone; 1,2,5,8-tetra-hydroxy anthraquinone (Quinalizarin); 3-methyl-1,6,8-trihydroxy anthraquinone (Emodin); anthraquinone; anthraquinone-2-sulfonic acid; benzoquinone; tetramethyl benzoquinone; hydroquinone; chlorohydroquinone; resorcinol; and 4-chlororesorcinol.

6. Retinoids

Examples of retinoids include all-trans retinal; $C_{17}$ aldehyde; $C_{22}$ aldehyde; 11-cis retinal; 13-cis retinal; retinal; and retinal palmitate.

7. Rhodamines

Examples of rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

8. Other Photoactivatable Molecules

Other non-limiting examples of photoactivatable molecules that may be useful in the target-binding agents are bacteriochlorophyll-A derivatives, described in U.S. Pat. Nos. 5,171,741 and 5,173,504; photosensitizing Diels-Alder porphyrin derivatives, described in U.S. Pat. No. 5,308,608; porphyrin-like compounds, described in U.S. Pat. Nos. 5,405,957, 5,512,675, and 5,726,304; imines of porphyrin and porphyrin derivatives, as described in U.S. Pat. Nos. 5,424,305 and 5,744,598; alkyl ether analogs of benzoporphyrin derivatives, as described in U.S. Pat. No. 5,498,710; purpurin-18, bacteriopurpurin-18 and related compounds, as described in U.S. Pat. No. 5,591,847; meso-substituted chorins, isobacteriochlorins and bacteriochlorins, as described in U.S. Pat. No. 5,648,485; meso-substituted tetramacrocyclic compounds, as described in U.S. Pat. No. 5,703,230; carbodiimide analogs of chlorins and bacteriochlorins, as described in U.S. Pat. No. 5,770,730; meso-substituted chlorins, isobacteriochlorins and bacteriochlorins, as described in U.S. Pat. No. 5,831,088; polypyrrolic macrocycles from meso-substituted tripyrrane compounds, described in U.S. Pat. Nos. 5,703,230, 5,883,246, and 5,919,923; isoimides of chlorins and bacteriochlorins, described in U.S. Pat. No. 5,864,035; alkyl ether analogs of chlorins having an N-substituted imide ring, as described in U.S. Pat. No. 5,952,366; ethylene glycol esters, described in U.S. Pat. No. 5,929,105; carotene analogs of porphyrins, chlorins and bacteriochlorins, as described in U.S. Pat. No. 6,103,751; fatty acid ester derivatives of porphyrin, chlorin, or bacteriochlorin, as described in U.S. Pat. No. 6,245,811; indium photosensitizers, as described in U.S. Pat. No. 6,444,194; porphyrins, chlorins, bacteriochlorins, and related tetrapyrrolic compounds described in U.S. Pat. No. 6,534,040; 1,3-propane diol ester and ether derivatives of porphyrins, chlorins and bacteriochlorins, as described in U.S. Pat. No. 6,555,700; trans beta substituted chlorins, as described in U.S. Pat. No. 6,559,374; and palladium-substituted bacteriochlorophyl derivatives, as described in U.S. Pat. No. 6,569,846; and the photosensitizer entities disclosed in Wilson et al., (*Curr. Micro.* 25:77-81 (1992)) and in Okamoto et al., (*Lasers in Surg. Med.* 12:450-485 (1992)). Generally any hydrophobic or hydrophilic photosensitizing agent, that absorbs in the ultra-violet, visible and infra-red spectroscopic ranges, would be useful in the disclosed conjugates.

D. Quencher Molecules

In various embodiments, the target-binding agents include a quencher molecule. In an embodiment, a light quencher is provided to prevent activation of the photoactivatable molecule if the targeting composition is not bound to a target molecule. Alternatively, the quencher may capture singlet oxygen from the photoactivatable molecule in situations where the target-binding agent is not bound to the target.

In an embodiment, the quencher molecule quenches the excited state of the photoactivatable molecule. For example, upon binding of the target-binding agent to its target, the three dimensional structure of the target-binding agent is altered in such a way that the quenching agent is no longer positioned close enough to quench the excited state of the photoactivatable molecule, thus allowing the photoactivatable molecule to function as required for generation of singlet oxygen. The singlet oxygen is then available to destroy the target or lyse the modified red blood cell. The quenching agent serves to prevent the generation of false positive signals from the photoactivatable molecule when it is not bound to the target.

In a specific embodiment, the photoactivatable molecule is a porphyrin or porphyrin derivative tetrapyrrole that includes a metal atom in its central coordination cavity and the quencher comprises one or more suitable functional groups that coordinate to the axial position of the metal coordinated within the photoactivatable molecule. The target recognition moiety is positioned in the agent in such a way that the interaction of the target recognition moiety with the target disrupts the association of the axial ligand to the metal, releasing the quenching agent and allowing the porphyrin or porphyrin derivative tetrapyrrole to be activated when irradiated.

In an embodiment, the quencher molecule is a light quencher, which prevents light of a suitable wavelength from exciting the photoactivable molecule. For instance, the quencher may absorb photons of a particular wavelength before those photons activate the photoactivatable molecule. Suitable light quenchers may include 4-(4'-dimethylaminophenylazo)benzoic acid (Dabcyl) or dark quenchers, such as black hole quenchers sold under the tradename "BHQ" (e.g., BHQ-0, BHQ-1, BHQ-2, and BHQ-3, Biosearch Technologies, Novato, Calif.). Dark quenchers also may include quenchers sold under the tradename "QXL™" (Anaspec, San Jose, Calif.). Dark quenchers also may include DNP-type non-fluorophores that include a 2,4-dinitrophenyl group.

In an embodiment, the quencher molecule is an antioxidant which captures singlet oxygen produced by the photoactivatable molecule before it can cause damage to surround cells or tissues. Suitable quenchers for singlet oxygen include, but are not limited to, glutathione, trolox, flavonoids, vitamin C, vitamin E, cysteine and ergothioneine and other non-toxic quenchers.

E. Molecules

In an embodiment, the red blood cells may be modified with fusion molecules or fusogens known to facilitate fusion with other cells. Upon fusion, the modified red blood cell may release its loaded content such as, for example, an anti-cancer therapeutic agent or a photosensitive reagent. For instance, breast cancer cells have been shown to express an endogenous retroviral envelope protein, syncytin-1, that enables the tumor cells to fuse in vivo with endothelial cells expressing a corresponding D-type retroviral receptor, the Na+-dependent neutral amino acid transporter ASCT2 (See, e.g., Larsson el al., *Scientific World Journal* 7:1193-1197 (2007)). Syncytin-1 is also expressed by endometrial carcinomas. As such, red blood cells may be modified with a syncytin-1 interacting receptor such as, for example, ASCT2 that would enable the modified red blood cells to fuse with cancer cells. For example, cDNA encoding human ASCT2 may be cloned using sequence information available in NCBI/GenBank (See, e.g., accession number NP_005619). Alternatively, cDNA encoding human ASCT2 may be acquired from a commercial source (e.g., OriGene Technologies, Inc., Rockville, Md., USA). The cDNA is cloned into an appropriate expression vector and subsequently transfected into cultured hematopoietic stem cells. Alternatively, the cDNA encoding ASCT2 may be transcribed to generate mRNA which is subsequently introduced into isolated reticulocytes as described above.

II. Assembly of the Target-Binding Agents

A. Attachment of a Target Recognition Moiety to a Photoactivatable Molecule and a Quencher Molecule In an embodiment, the target recognition moiety of the target-binding agent is conjugated to a photoactivable molecule and a quencher molecule. Upon binding of the target recognition moiety to the target molecule, the quencher molecule is released or otherwise separated from the photoactivateable molecule. In the "unquenched" state, the photoactivatable molecule may be activated by light of a suitable wavelength. The conjugation of these molecules is typically by way of attachment sites. Most attachments are conveniently effected via sulfhydryl or amine interactions. Synthetic and commercial alternatives are available depending on the selected photoactivable molecule, or quencher molecule. The distance between the photoactivatable molecule and the quencher molecule is selected so that interaction of the target recognition moiety results in repositioning of the quencher molecule. If the photoactivatable molecule and the quencher are too close, then interaction of the target recognition moiety with the target may not end quenching of photoactivatable molecule. If the distance between the photoactivatable molecule and the quencher molecule is too great, then the quencher molecule may not prevent all electromagnetic radiation from reaching the photoactivatable molecule. The distances can be determined by any method, such as by calculation or empirically.

Techniques in synthetic chemistry provide methods for the attachment of photoactivatable molecule and/or quencher molecule to the target recognition moiety. For example, synthetic linkage techniques are known that allow incorporation of both various types of molecules, including a photoactivatable molecule and an quencher molecule within an oligonucleotide (See U.S. Pat. No. 4,996,143). There is extensive guidance in the literature for derivatizing photoactivatable and quencher molecules for covalent attachment via readily available reactive groups that can be added to a molecule. The diversity and utility of chemistries available for conjugating molecules and surfaces is exemplified by the extensive body of literature on preparing nucleic acids derivatized with fluorophores. See, for example, Ullhman et al., U.S. Pat. No. 3,996,345 and Khanna et al., U.S. Pat. No. 4,351,760.

The target-binding agents disclosed herein can be conjugated by using a coupling agent. Any bond which is capable of linking the components such that they are stable under physiological conditions for the time needed for administration and treatment is suitable, but covalent linkages are preferred. The link between two components may be direct, e.g., where a photoactivatable molecule is linked directly to a target recognition moiety, or indirect, e.g., where a photoactivatable molecule is linked to a linking component and that linking component being linked to the target recognition moiety.

A coupling agent should function under conditions of temperature, pH, salt, solvent system, and other reactants that substantially retain the chemical stability of the photoactivatable molecule, the quencher molecule and the target recognition moiety. Coupling agents should link the component moieties stably, but such that there is only minimal or no denaturation or deactivation of the photoactivatable molecule, quencher molecule or the target recognition moiety. Many coupling agents react with an amine and a carboxylate, to form an amide, or an alcohol and a carboxylate to form an ester. Coupling agents are known in the art (See, e.g., Bodansky, *Principles of Peptide Synthesis,* 2nd ed, John Wiley, N.Y. (1991), and Greene & Wuts, *Protective Groups in Organic Synthesis,* 2nd ed, John Wiley, N.Y. (1991)). Representative combinations of such groups are amino with carboxyl to form amide linkages, or carboxy with hydroxy to form ester linkages or amino with alkyl halides to form alkylamine linkages, or thiols with thiols to form disulfides, or thiols with maleimides or alkyl halides to form thioethers. Obviously, hydroxyl, carboxyl, amino and other functionalities, where not present may be introduced by known methods.

The target-binding agents provided herein can be prepared by coupling the photoactivatable molecule to a target recognition moiety, such as an antibody, by cleaving an available ester moiety on the photoactivatable molecule and coupling the compound via peptide linkages to an antibody through an N terminus, or by other methods known in the art. A variety of coupling agents, including cross-linking agents, can be used for covalent conjugation. Examples of cross-linking agents include N,N'-dicyclohexylcarbodiimide (DCC), N-succinimidyl-S-acetyl-thioacetate (SATA), N-succinimidyl-3-(2-pyridyldithio)propionate (SPDP), ortho-phenylene-dimaleimide (o-PDM), and sulfosuccinimidyl 4N-maleimido-methyl)-cyclohexane-1-carboxylate (sulfo-SMCC). See, e.g., Karpovsky et al., *J. Exp. Med.* 160:1686 (1984); and Liu M A et al., *Proc. Natl. Acad. Sci. USA* 82: 8648 (1985). Other methods include those described by Brennan et al., *Science* 229: 81-83 (1985) and Glennie et al., *J. Immunol.* 139: 2367-2375 (1987). A large number of coupling agents for peptides and proteins, along with buffers, solvents, and methods of use, are described in the Pierce Chemical Co. catalog, pages O-90 to O-110 (1995, Pierce Chemical Co., 3747 N. Meridian Rd., Rockford Ill., 61105, U.S.A.).

For example, DCC is a useful coupling agent that can be used to promote coupling of the alcohol NHS to chlorin e6 in DMSO forming an activated ester which can be cross-linked to polylysine. DCC is a carboxy-reactive cross-linker commonly used as a coupling agent in peptide synthesis. Another useful cross-linking agent is SPDP, a heterobifunctional cross-linker for use with primary amines and sulfhydryl groups. SPDP has a molecular weight of 312.4, a spacer arm length of 6.8 angstroms, is reactive to NHS-esters and pyridyldithio groups, and produces cleavable cross-linking such that, upon further reaction, the agent is eliminated so the photoactivatable molecule can be linked directly to a linking component or target recognition moiety. Other useful conjugating agents are SATA for introduction of blocked SH groups for two-step cross-linking, which is deblocked with hydroxylamine-HCl, and sulfo-SMCC, reactive towards amines and sulfhydryls. Other cross-linking and coupling agents are also available from Pierce Chemical Co. Additional compounds and processes, particularly those involving a Schiff base as an intermediate, for conjugation of proteins to other proteins or to other compositions, for example to reporter groups or to chelators for metal ion labeling of a protein, are disclosed in EPO 243,929 A2 (published Nov. 4, 1987).

Reactive Groups. The photoactivatable molecule or target recognition moiety can be conjugated, directly or through a linking component, to the quencher molecule using reactive groups, either on the donor molecule or on the acceptor molecule or the targeting moiety. For example, molecules that contain carboxyl groups can be joined to lysine-amino groups in the target polypeptides either by preformed reactive esters (such as N-hydroxy succinimide ester) or esters conjugated in situ by a carbodiimide-mediated reaction. The same applies to molecules that contain sulfonic acid groups, which can be transformed to sulfonyl chlorides which react with amino groups. Molecules that have carboxyl groups can be joined to amino groups, such as on a polypeptide, by an in situ carbodiimide method. Molecules can also be attached to hydroxyl groups of serine or threonine residues or to sulfhydryl groups of cysteine residues.

Methods of joining components of a target-binding agent can use heterobifunctional cross linking reagents. These agents bind a functional group in one chain and to a different functional group in the second chain. These functional groups typically are amino, carboxyl, sulfhydryl, and aldehyde. There are many permutations of appropriate moieties which will react with these groups and with differently formulated structures, to conjugate them together. (See Merrifield et al., *Ciba Found Symp.* 186: 5-20 (1994)).

The photoactivatable molecule of the target-binding agent may be optionally functionalized so as to include a linking component which allows the photoactivatable molecule to be linked to a target recognition moiety, such as an analyte, antigen, antibody or other molecule. For example, the linking component may include, but is not limited to, an oligonucleotide, a polynucleotide, a nucleic acid, an oligosaccharide, a polysaccharide or a diaminoalkane linking species, such as 1,3-diaminopropane. A variety of linking components which are suited to this purpose have been described. For example, see Kricka, *Ligand-Binder Assays, Labels and Analytical Strategies*, pp. 15-51, Marcel Dekker, Inc., New York, N.Y. (1985)). The photoactivatable molecule is linked to the linking component and the linking component is linked to the analyte, antigen, antibody or other molecule using conventional techniques.

Reactive Groups and Reactions. Reactive groups and classes of reactions useful in preparing the disclosed conjugates are generally those that are well known in the art of bioconjugate chemistry. Classes of reactions include those that proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction). These and other useful reactions are discussed in, for example, Morrison et al., *Organic Chemistry*, 4th Ed., Allyn and Bacon, Inc. (1983), and Hermanson, *Bioconjugate Techniques*, Academic Press, San Diego (1996).

For example, useful reactive functional groups include: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups, which can be converted to esters, ethers, aldehydes, etc.; (c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups, which are capable of participating in Diels-Alder reactions such as, for example, maleimido groups; (e) carbonyl groups, such that subsequent derivatization is possible via formation of carbonyl derivatives such as, for example, imines, hydrazones, semicarbazones or oximes, or via such mechanisms as Grignard addition or alkyllithium addition; (f) sulfonyl groups for subsequent reaction with amines, for example, to form sulfonamides; (g) thiol groups, which can be converted to disulfides or reacted with acyl halides; (h) amine or sulfhydryl groups, which can be, for example, acylated, alkylated or oxidized; (i) alkenes, which can undergo, for example, cycloadditions, acylation, Michael addition, etc; (j) epoxides, which can react with, for example, amines and hydroxyl compounds; and (k) phosphoramidites and other standard functional groups useful in nucleic acid synthesis.

B. Placement of the Photoactivatable Molecule and Quencher Molecule

The photoactivatable molecule and quencher molecule of the target-binding agents disclosed herein are positioned to be in a configuration so that the agent is in a "quenched state" when it is not interacting with a target molecule. When the agent interacts with a target via the target recognition moiety, the photoactivatable molecule and the quencher molecule are separated. Thus, the spatial rearrangement of the photoactivatable molecule and quencher in the target-binding agent occurs only after interaction of the target recognition moiety with its target. Hence, the target recognition moiety is selected and positioned in the conjugate so that when the target recognition moiety interacts with its target, the spatial arrangement of the agent is changed such that the photoactivatable molecule is are no longer in a quenched state.

C. Conjugation of Target-binding Agents and/or Fusion Molecules to Red Blood Cells In an embodiment, the target-binding agent may be bound to the surface of a modified red blood cell through a biotin-streptavidin bridge. For example, a biotinylated antibody may be linked to a non-specifically biotinylated cell surface through a streptavidin bridge. In an embodiment, the target-binding agent is attached to the red blood cell via the target recognition moiety, e.g., antibody. Antibodies can be conjugated to biotin by a number of chemical means (See, e.g., Hirsch et al., *Methods Mol. Biol.* 295: 135-154 (2004)). The surface membrane proteins of a red blood cell may be biotinylated using an amine reactive biotinylation reagent such as, for example, EZ-Link Sulfo-NHS-SS-Biotin (sulfosuccinimidyl 2-(biotinamido)-ethyl-1,3-dithiopropionate; Pierce-Thermo Scientific, Rockford, Ill., USA; See, e.g., Jaiswal et al., *Nature Biotech.* 21:47-51 (2003)). Isolated red blood cells may be incubated for 30 min at 4° C. in 1 mg/ml solution of sulfo-NHS-SS in phosphate-buffered saline. Excess biotin reagent is removed by washing the cells with Tris-buffered saline, for example. The biotinylated cells are then reacted with the biotinylated antibody in the presence of streptavidin to form the modified red blood cells.

In another embodiment, the target-binding agent may be attached to the surface of the modified red blood with a bispecific antibody, for example, with both target cell and red blood cell binding activities. The number of antigen binding sites on the modified red blood cell may range from about 0 to over 1000 sites, for example, depending upon the binding conditions (See, e.g., U.S. Pat. No. 5,470,570). The red blood cells may be further modified as described herein and re-introduced into an individual.

Alternatively, the bispecific antibody, for example, may be added directly to the bloodstream where it optimally binds in vivo to the modified red blood cell and to the target cell (See, e.g., U.S. Patent Application 2003/0215454). Alternatively, a unique receptor molecule may be expressed on the surface of a modified red blood cell that is detected by the bispecific antibody to ensure the selectivity of bispecific antibody to the modified red blood cell.

For example, the following receptors can be used to target macrophages: the complement receptor (Rieu et al., *J. Cell Biol.* 127:2081-2091 (1994)), the scavenger receptor (Brasseur et al., *Photochem. Photobiol.* 69:345-352 (1999)), the transferrin receptor (Dreier et al., *Bioconjug. Chem.* 9:482-489 (1998); Hamblin et al., *J. Photochem. Photobiol.* 26:4556 (1994)); the Fc receptor (Rojanasakul et al., *Pharm. Res.* 11:1731-1733 (1994)); the mannose receptor (Frankel et al., *Carbohydr. Res.* 300:251-258 (1997); Chakrabarty et al., *J. Protozool.* 37:358-364 (1990)). Target recognition moieties that can be conjugated with photoactivatable molecules, for example to target to macrophages, include low density lipoproteins (Mankertz et al., *Biochem. Biophys. Res. Commun.* 240:112-115 (1997); von Baeyer et al., *Int. J. Clin. Pharmacol. Ther. Toxicol.* 31:382-386 (1993)), very low density lipoproteins (Tabas et al., *J. Cell Biol.* 115:1547-1560 (1991)), mannose residues and other carbohydrate moieties (Pittet et al., *Nucl. Med. Biol.* 22:355-365 (1995)), poly-cationic molecules, such as poly-L-lysine (Hamblin et al., *J. Photochem. Photobiol.* 26:45-56 (1994)), liposomes (Bakker-Woudenberg et al., *J. Drug Target.* 2:363-371 (1994); Betageri et al., *J. Pharm. Pharmacol.* 45:48-53 (1993)), antibodies (Gruenheid et al., *J. Exp. Med.* 185:717-730, (1997)), and 2-macroglobulin (Chu et al., *J. Immunol.* 152:1538-1545 (1994)).

In another embodiment, the target-binding agent is attached to the red blood cell via a covalent attachment. For example, the target recognition moiety may be derivatized and bound to the red blood cell using a coupling compound containing an electrophilic group that will react with nucleophiles on the red blood cell to form the interbonded relationship. Representative of these electrophilic groups are $\alpha,\beta$ unsaturated carbonyls, alkyl halides and thiol reagents such as substituted maleimides. In addition, the coupling compound can be coupled to the target recognition moiety via one or more of the functional groups in the target recognition moiety such as amino, carboxyl and tryosine groups. For this purpose, coupling compounds should contain free carboxyl groups, free amino groups, aromatic amino groups, and other groups capable of reaction with enzyme functional groups. Highly charged derivatives of target recognition moiety can also be prepared for immobilization on erythrocytes through electrostatic bonding. Examples of these derivatives would include polylysyl and polyglutamyl enzymes.

The choice of the reactive group embodied in the derivative depends on the reactive conditions employed to couple the electrophile with the nucleophilic groups on the red blood cell for immobilization. A controlling factor is the desire not to inactivate the coupling agent prior to coupling of the target recognition moiety immobilized by the attachment to the red blood cell.

Such coupling immobilization reactions can proceed in a number of ways. Typically, a coupling agent can be used to form a bridge between the macromolecule and the red blood cell. In this case, the coupling agent should possess a functional group such as a carboxyl group which can be caused to react with the target recognition moiety. One pathway for preparing the macromolecular derivative comprises the utilization of carboxyl groups in the coupling agent to form mixed anhydrides which react with the target recognition moiety, in which use is made of an activator which is capable of forming the mixed anhydride. Representative of such activators are isobutylchloroformate or other chloroformates which give a mixed anhydride with coupling agents such as 5,5'-(dithiobis (2-nitrobenzoic acid) (DTNB), p-chloromercuribenzoate (CMB), or m-maleimidobenzoic acid (MBA). The mixed anhydride of the coupling agent reacts with the target recognition moiety to yield the reactive derivative which in turn can react with nucleophilic groups on the red blood cell to immobilize the macromolecule.

Functional groups on the target recognition moiety such as carboxyl groups can be activated with carbodiimides and the like activators. Subsequently, functional groups on the bridging reagent, such as amino groups, will react with the activated group on the target recognition moiety to form the reactive derivative. In addition, the coupling agent should possess a second reactive grouping which will react with appropriate nucleophilic groups on the red blood cell to form the bridge. Typical of such reactive groupings are alkylating agents such as iodoacetic acid, $\alpha$, $\beta$ unsaturated carbonyl compounds, such as acrylic acid and the like, thiol reagents, such as mercurials, substituted maleimides and the like.

Alternatively, functional groups on the target recognition moiety can be activated so as to react directly with nucleophiles on red blood cells to obviate the need for a bridge-forming compound. For this purpose, beneficial use is made of an activator such as Woodward's Reagent K or the like reagent which brings about the formation of carboxyl groups in the target recognition moiety into enol esters, as distinguished from mixed anhydrides. The enol ester derivatives of target recognition moieties will subsequently react with nucleophilic groups on the red blood cell to effect immobilization of the macromolecule.

D. Genetically Engineered Red Blood Cells

In an embodiment, red blood cell precursor cells are genetically engineered to express one or more protein- or RNA-based pharmaceuticals and/or one or more imaging agents (e.g., a fluorescent protein). This section describes the transformation of reticulocytes and hematopoietic stem cells, which are both precursor cells for mature erythrocytes.

1. Transformation of Reticulocytes

Isolated reticulocytes may be transfected with mRNA encoding proteins and/or peptides of interest. Messenger RNA may be derived from in vitro transcription of a cDNA plasmid construct containing the coding sequence corresponding to the protein and/or peptide of interest. For example, the cDNA sequence corresponding to the protein and/or peptide of interest may be inserted into a cloning vector containing promoter sequence compatible with specific RNA polymerases. For example, the cloning vector ZAP Express® pBK-CMV (Stratagene, La Jolla, Calif., USA) contains T3 and T7 promoter sequence compatible with T3 and T7 RNA polymerase, respectively. For in vitro transcription of sense mRNA, the plasmid is linearized at a restriction site downstream of the stop codon(s) corresponding to the end of the coding sequence of the protein and/or peptide of interest. The mRNA is transcribed from the linear DNA template using a commercially available kit such as, for example, the RNAMaxx® High Yield Transcription Kit (from Stratagene, La Jolla, Calif., USA). In some instances, it may be desirable to generate 5'-m$^7$GpppG-capped mRNA. As such, transcription of a linearized cDNA template may be carried out using, for example, the mMESSAGE mMACHINE High Yield Capped RNA Transcription Kit from Ambion (Austin, Tex., USA). Transcription may be carried out in a reaction volume of 20-100 μl at 37° C. for 30 min to 4 h. The transcribed mRNA is purified from the reaction mix by a brief treatment with DNase I to eliminate the linearized DNA template followed by precipitation in 70% ethanol in the presence of lithium chloride, sodium acetate or ammonium acetate. The integrity of the transcribed mRNA may be assessed using electrophoresis with an agarose-formaldehyde gel or commercially available Novex pre-cast TBE gels (e.g., Novex, Invitrogen, Carlsbad, Calif., USA).

Messenger RNA encoding proteins and/or peptides of interest may be introduced into reticulocytes using a variety of approaches including, for example, lipofection and electroporation (van Tandeloo et al., Blood 98:49-56 (2001)). For lipofection, for example, 5 μg of in vitro transcribed mRNA in Opti-MEM (Invitrogen, Carlsbad, Calif., USA) is incubated for 5-15 min at a 1:4 ratio with the cationic lipid DMRIE-C (Invitrogen). Alternatively, a variety of other cationic lipids or cationic polymers may be used to transfect cells with mRNA including, for example, DOTAP, various forms of polyethylenimine, and polyL-lysine (Sigma-Aldrich, Saint Louis, Mo., USA), and Superfect (Qiagen, Inc., Valencia, Calif., USA; See, e.g., Bettinger et al., Nucleic Acids Res. 29:3882-3891 (2001)). The resulting mRNA/lipid complexes are incubated with cells (1-2×10$^6$ cells/ml) for 2 h at 37° C., washed and returned to culture. For electroporation, for example, about 5 to 20×10$^6$ cells in 500 μl of Opti-MEM (Invitrogen, Carlsbad, Calif., USA) are mixed with about 20 μg of in vitro transcribed mRNA and electroporated in a 0.4-cm cuvette using, for example, and Easyject Plus device (EquiBio, Kent, United Kingdom). In some instances, it may be necessary to test various voltages, capacitances and electroporation volumes to determine the optimal conditions for transfection of a particular mRNA into a reticulocyte. In general, the electroporation parameters required to efficiently transfect cells with mRNA appear to be less detrimental to cells than those required for electroporation of DNA (van Tandeloo et al., Blood 98:49-56 (2001)).

Alternatively, mRNA may be transfected into a reticulocyte using a peptide-mediated RNA delivery strategy (See, e.g., Bettinger et al., Nucleic Acids Res. 29:3882-3891 (2001)). For example, the cationic lipid polyethylenimine 2 kDA (Sigma-Aldrich, Saint Louis, Mo., USA) may be combined with the melittin peptide (Alta Biosciences, Birmingham, UK) to increase the efficiency of mRNA transfection, particularly in post-mitotic primary cells. The mellitin peptide may be conjugated to the PEI using a disulfide cross-linker such as, for example, the hetero-bifunctional cross-linker succinimidyl 3-(2-pyridyldithio) propionate. In vitro transcribed mRNA is preincubated for 5 to 15 min with the mellitin-PEI to form an RNA/peptide/lipid complex. This complex is then added to cells in serum-free culture medium for 2 to 4 h at 37° C. in a 5% $CO_2$ humidified environment and then removed and the transfected cells allowed to continue growing in culture.

2. Transformation of Hematopoetic Stem Cells

Non-endogenous proteins such as, for example, receptors, enzymes and/or therapeutic peptides may be genetically introduced into hematopoietic stem cells prior to terminal differentiation using a variety of DNA techniques, including transient or stable transfections and gene therapy approaches. These non-endogenous proteins expressed on the surface and/or in the cytoplasm of mature red blood cell may be used to target the modified red blood cell to a specific location, to bind specific blood analytes, to react and/or signal in the presence of specific analytes, and/or to treat a specific disease or condition.

Viral based gene transfer. Viral gene transfer may be used to transfect hematopoietic stem cells with DNA encoding proteins and/or peptides of interest (Papapetrou et al., Gene Therapy 12:S118-S130 (2005)). A number of viruses may be used as gene transfer vehicles including Moloney murine leukemia virus (MMLV), adenovirus, adeno-associated virus, herpes simplex virus (HSV), lentiviruses such as human immunodeficiency virus 1 (HIV 1), and spumaviruses such as foamy viruses, for example (See, e.g., Osten et al., HEP 178:177-202 (2007)). Retroviruses, for example, efficiently transduce mammalian cells including human cells and integrate into chromosomes, conferring stable gene transfer.

A cell membrane associated receptor, for example, may be transcribed into hematopoietic stem cells and subsequently expressed in a mature red blood cell using a Moloney murine leukemia virus (MMLV) vector backbone (Malik et al., Blood 91:2664-2671 (1998)). Vectors based on MMLV, an oncogenic retrovirus, are currently used in gene therapy clinical trials (Hossle et al., News Physiol. Sci. 17:87-92 (2002)). A DNA construct containing the cDNA encoding a cell membrane associated receptor such as, for example, the mu opioid receptor is generated in the MMLV vector backbone using standard molecular biology techniques. The construct is transfected into a packaging cell line such as, for example, PA317 cells and the viral supernatant is used to transfect producer cells such as, for example, PG13 cells. The PG13 viral supernatant is incubated with hematopoietic stem cells that have been isolated and cultured as described in above. The expression of the cell membrane associated receptor such as, for example, the mu opioid receptor may be monitored using FACS analysis (fluorescence-activated cell sorting), for example, with a fluorescently labeled antibody directed against the cell membrane associated receptor. Similar methods may be used to express a cytoplasmic protein such as, for example, a modified hemoglobin molecule (See, e.g., Nicolini et al., *Blood* 100: 1257-1264 (2002)) or a small peptide such as, for example, a cytokine (See, e.g., Song et al., *Cancer Res.* 66:6304-6311 (2006)) in a hematopoietic stem cell.

Similarly, a fluorescent tracking molecule such as, for example, green fluorescent protein (GFP) may be transfected into hematopoietic stem cells using a viral-based approach (Tao et al., *Stem Cells* 25:670-678 (2007)). As such, bone marrow cells are isolated and cultured as described herein. Two days prior to transfection, the cells are prestimulated in minimum essential medium (MEM) containing 20% fetal bovine serum, 4 mM L-glutamine, 100 units/ml penicillin, 100 µg/ml streptomycin, 100 ng/ml murine stem cell factor, 100 ng/ml murine FLT3-ligand, and 100 ng/ml murine thrombopoietin. Ecotopic retroviral vectors containing DNA encoding the enhanced green fluorescent protein (EGFP) or a red fluorescent protein (e.g., DsRed-Express) are packaged using a packaging cell such as, for example, the Phoenix-Eco cell line (distributed by Orbigen, San Diego, Calif.). Packaging cell lines stably express viral proteins needed for proper viral packaging including, for example, gag, pol, and env. Supernatants from the Phoenix-Eco cells into which viral particles have been shed are used to transduce prestimulated hematopoietic stem cells. In some instances, transduction may be performed on a specially coated surface such as, for example, fragments of recombinant fibronectin to improve the efficiency of retroviral mediated gene transfer (e.g., RetroNectin, Takara Bio USA, Madison, Wis.). As such, prestimulated cells are incubated in RetroNectin-coated plates with retroviral Phoenix-Eco supernatants plus 100 ng/ml murine stem cell factor, 100 ng/ml murine FLT3-ligand, and 100 ng/ml murine thrombopoietin. After incubation at 37° C., plates are centrifuged at 400×g for 5 min at 20° C. and further incubated at 37° C. for 5.5 h. Transduction may be repeated the next day. In this instance, the percentage of cells expressing EGFP or DsRed-Express may be assessed by FACS. Other reporter genes that may be used to assess transduction efficiency include, for example, beta-galactosidase, chloramphenicol acetyltransferase, and luciferase as well as low-affinity nerve growth factor receptor (LNGFR), and the human cell surface CD24 antigen (Bierhuizen et al., *Leukemia* 13:605-613 (1999)).

Non-viral gene transfer. Nonviral vectors may be used to introduce genetic material into hematopoietic stem cells (Papapetrou et al., *Gene Therapy* 12:S118-S130 (2005)). Nonviral-mediated gene transfer differs from viral-mediated gene transfer in that the plasmid vectors contain no proteins, are less toxic and easier to scale up, and have no host cell preferences. The "naked DNA" of plasmid vectors are by themselves inefficient in delivering genetic material to a cell and therefore are combined with a gene delivery method that enables entry into cells. A number of delivery methods may be used to transfer nonviral vectors into hematopoietic stem cells including chemical and physical methods.

A nonviral vector encoding a protein and/or peptide of interest may be introduced into hematopoietic stem cells using synthetic macromolecules such as cationic lipids and polymers (Papapetrou et al., *Gene Therapy* 12:S118-S130 (2005)). Cationic liposomes, for example form complexes with DNA through charge interactions. The positively charged DNA/lipid complexes bind to the negative cell surface and are taken up by the cell by endocytosis. This approach may be used, for example, to transfect hematopoietic cells (See, e.g., Keller et al., *Gene Therapy* 6:931-938 (1999)). Hematopoietic cells are cultured in association with adherent stromal cells as described herein. The plasmid DNA (approximately 0.5 µg in 25-100 µL of a serum free medium, such as, for example, OptiMEM (Invitrogen, Carlsbad, Calif.)) is mixed with a cationic liposome (approximately 4 µg in 25 µL of serum free medium) such as the commercially available transfection reagent Lipofectamine™ (Invitrogen, Carlsbad, Calif.) and allowed to incubate for at least 20 min to form complexes. The DNA/liposome complex is added to the hematopoietic cells and allowed to incubate for 5-24 h, after which time transgene expression may be assayed. Alternatively, other commercially available liposome tranfection agents may be used (e.g., In vivo GeneSHUTTLE™, Qbiogene, Carlsbad, Calif.).

Alternatively, a cationic polymer such as, for example, polyethylenimine (PEI) may be used to efficiently transfect hematopoietic and umbilical cord blood-derived CD34+ cells (See, e.g., Shin et al., *Biochim. Biophys. Acta* 1725:377-384 (2005)). Human CD34+ cells are isolated from human umbilical cord blood as described herein and cultured in Iscove's modified Dulbecco's medium supplemented with 200 ng/ml stem cell factor and 20% heat-inactivated fetal bovine serum. Plasmid DNA encoding the protein or proteins of interest is incubated with branched or linear PEIs varying in size from 0.8 K to 750 K (Sigma Aldrich, Saint Louis, Mo., USA; Fermetas, Hanover, Md., USA). PEI is prepared as a stock solution at 4.2 mg/ml distilled water and slightly acidified to pH 5.0 using HCl. The DNA may be combined with the PEI for 30 min at room temperature at various nitrogen/phosphate ratios based on the calculation that 1 µg of DNA contains 3 nmol phosphate and 1 µl of PEI stock solution contains 10 nmol amine nitrogen. The isolated CD34+ cells are seeded with the DNA/cationic complex, centrifuged at 280×g for 5 min and incubated in culture medium for 4 or more h until gene expression is assessed.

A plasmid vector may be introduced into a hematopoietic stem cell using a physical method such as particle-mediated transfection, "gene gun", biolistics, or particle bombardment technology (Papapetrou, et al., (2005) *Gene Therapy* 12:S118-S130). In this instance, DNA encoding the protein and/or peptides of interest is absorbed onto gold particles and administered to cells by a particle gun. This approach may be used, for example, to transfect hematopoietic stem cells derived from umbilical cord blood (See, e.g., Verma et al., *Gene Therapy* 5:692-699 (1998)). As such, umbilical cord blood is isolated and diluted three fold in phosphate buffered saline. CD34+ cells are purified using an anti-CD34 monoclonal antibody in combination with magnetic microbeads coated with a secondary antibody and a magnetic isolation system (e.g., Miltenyi MiniMac System, Auburn, Calif., USA). The CD34+ enriched cells may be cultured as described herein. Alternatively, the CD34+ enriched cells may be cultured on irradiated stromal cells in IMDM medium, for example, with 20% fetal bovine serum, 1% deionized bovine serum albumin, penicillin/streptomycin, L-glutamine, 2-mercaptoethanol and hydrocortisone supplemented with IL-3 (5 ng/ml), IL-6 (25 ng/ml), and stem cell factor (50 ng/ml). For transfection, plasmid DNA is precipitated onto a particle, for example gold beads, by treatment with calcium chloride and spermidine. Following washing of the DNA-coated beads with ethanol, the beads may be delivered into the cultured cells using, for example, a Biolistic PDS-1000/He System (Bio-Rad, Hercules, Calif., USA). A reporter gene such as, for example, beta-galactosidase, chloramphenicol acetyltransferase, luciferase, or green fluorescent protein may be used to assess efficiency of transfection.

Alternatively, electroporation methods may be used to introduce a plasmid vector into hematopoietic stem cells (See, e.g., Wu et al., *Gene Ther.* 8:384-390 (2001)). Electroporation creates transient pores in the cell membrane, allowing for the introduction of various molecules into the cells including, for example, DNA and RNA as well as antibodies and drugs. As such, CD34+ cells are isolated and cultured as described herein. Immediately prior to electroporation, the cells are isolated by centrifugation for 10 min at 250×g at room temperature and resuspended at 0.2-10×10$^6$ viable cells/ml in an electroporation buffer such as, for example, X-VIVO 10 supplemented with 1.0% human serum albumin (HSA). The plasmid DNA (1-50 µg) is added to an appropriate electroporation cuvette along with 500 µl of cell suspension. Electroporation may be done using, for example, an ECM 600 electroporator (Genetronics, San Diego, Calif., USA) with voltages ranging from 200 V to 280 V and pulse lengths ranging from 25 to 70 milliseconds. A number of alternative electroporation instruments are commercially available and may be used for this purpose (e.g., Gene Pulser Xcell™, BioRad, Hercules, Calif.; Cellject Duo, Thermo Science, Milford, Mass.). Alternatively, efficient electroporation of isolated CD34+ cells may be performed using the following parameters: 4 mm cuvette, 1600 µF, 550 V/cm, and 10 µg of DNA per 500 µl of cells at 1×10$^5$ cells/ml (Oldak et al., *Acta Biochimica Polonica* 49:625-632 (2002)).

Nucleofection, a form of electroporation, may also be used to transfect hematopoietic stem cells. In this instance, transfection is performed using electrical parameters in cell-type specific solutions that enable DNA (or other reagents) to be directly transported to the nucleus thus reducing the risk of possible degradation in the cytoplasm. For example, a Human CD34 Cell Nucleofector™ Kit (from amaxa inc.) may be used to transfect hematopoietic stem cells. In this instance, 1-5×10$^6$ cells in Human CD34 Cell Nucleofector™ Solution are mixed with 1-5 µg of DNA and transfected in the Nucleofector™ instrument using preprogrammed settings as determined by the manufacturer.

Hematopoietic stem cells may be non-virally transfected with a conventional expression vector which is unable to self-replicate in mammalian cells unless it is integrated in the genome. Alternatively, hematopoietic stem cells may be transfected with an episomal vector which may persist in the host nucleus as autonomously replicating genetic units without integration into chromosomes (Papapetrou et al., *Gene Therapy* 12:S118-S130 (2005)). These vectors exploit genetic elements derived from viruses that are normally extrachromosomally replicating in cells upon latent infection such as, for example, EBV, human polyomavirus BK, bovine papilloma virus-1 (BPV-1), herpes simplex virus-1 (HSV) and Simian virus 40 (SV40). Mammalian artificial chromosomes may also be used for nonviral gene transfer (Vanderbyl et al., *Exp. Hematol.* 33:1470-1476 (2005)).

III. Loading of a Target-binding Agent or Molecular Agent into Red Blood Cells

In an embodiment, red blood cells are loaded with one or more target-binding agents, such that the one or more target-binding agents are internalized within the red blood cell. In an embodiment, red blood cells are loaded with one or more molecular agents. A molecular agent may include, but is not limited to, a compound that is configured to provide an activity to the subject and/or to the red blood cell following administration. In an embodiment, such agent may include, but is not limited to, one or more therapeutic agents or imaging agents.

A. Methods of Loading Red Blood Cells

A number of methods may be used to load modified red blood cells with an agent (e.g., target-binding agent or molecular agent) such as, for example, hypotonic lysis, hypotonic dialysis, osmosis, osmotic pulsing, osmotic shock, ionophoresis, electroporation, sonication, microinjection, calcium precipitation, membrane intercalation, lipid mediated transfection, detergent treatment, viral infection, diffusion, receptor mediated endocytosis, use of protein transduction domains, particle firing, membrane fusion, freeze-thawing, mechanical disruption, and filtration (See, e.g., U.S. Pat. No. 6,495,351 B2; U.S. Patent Application 2007/0243137 A1).

For hypotonic lysis, modified red blood cells are exposed to low ionic strength buffer causing them to burst. The therapeutic agent such as an antibiotic or chemotherapeutic agent, for example, distributes within the cells. Red blood cells may be hypotonically lysed by adding 30-50 fold volume excess of 5 mM phosphate buffer (pH 8), for example, to a pellet of isolated red blood cells. The resulting lysed cell membranes are isolated by centrifugation. The pellet of lysed red blood cell membranes is resuspended and incubated in the presence of the therapeutic agent in a low ionic strength buffer for 30 min, for example. Alternatively, the lysed red blood cell membranes may be incubated with the therapeutic agent for as little as one minute or as long as several days, depending upon the best conditions determined to efficiently load the cells.

Alternatively, red blood cells may be loaded with a therapeutic agent using controlled dialysis against a hypotonic solution to swell the cells and create pores in the cell membrane (See, e.g., U.S. Pat. Nos. 4,327,710, 5,753,221, and 6,495,351 B2). For example, a pellet of isolated red blood cells is resuspended in 10 mM HEPES, 140 mM NaCl, 5 mM glucose pH 7.4 and dialyzed against a low ionic strength buffer containing 10 mM NaH$_2$PO$_4$, 10 mM NaHCO$_3$, 20 mM glucose, and 4 mM MgCl$_2$, pH 7.4. After 30-60 min, the red blood cells are further dialyzed against 16 mM NaH$_2$PO$_4$, pH 7.4 solution containing the therapeutic agent for an additional 30-60 min. All of these procedures may be optimally performed at a temperature of 4° C. In some instances, it may be beneficial to load a large quantity of red blood cells with a therapeutic agent by a dialysis approach and as such a specific apparatus designed for this purpose may be used (See, e.g., U.S. Pat. Nos. 4,327,710, 6,139,836 and 6,495,351 B2).

The loaded red blood cells can be resealed by gentle heating in the presence of a physiological solution such as, for example, 0.9% saline, phosphate buffered saline, Ringer's solution, cell culture medium, blood plasma or lymphatic fluid. For example, well-sealed membranes may be generated by treating the disrupted red blood cells for 1-2 min in 150 mM salt solution of, for example, 100 mM phosphate (pH 8.0) and 150 mM sodium chloride at a temperature of 60° C. Alternatively, the cells may be incubated at a temperature of 25-50° C. for 30 min to 4 h, for example (See, e.g., U.S. Patent Application 2007/0243137 A1). Alternatively, the disrupted red blood cells may be resealed by incubation in 5 mM adenine, 100 mM inosine, 2 mM ATP, 100 mM glucose, 100 mM Na-pyruvate, 4 mM MgCl$_2$, 194 mM NaCl, 1.6 M KCl, and 35 mM NaH$_2$PO$_4$, pH 7.4 at a temperature of 37° C. for 20-30 min (See, e.g., U.S. Pat. No. 5,753,221).

For electroporation, for example, modified red blood cells are exposed to an electrical field which causes transient holes in the cell membrane, allowing the therapeutic agent to diffuse into the cell (See, e.g., U.S. Pat. No. 4,935,223). Modified red blood cell are suspended in a physiological and electrically conductive media such as, for example, platelet-free plasma to which the therapeutic agent is added. The mixture in a volume ranging from 0.2 to 1.0 ml is placed in an electroporation cuvette and cooled on ice for 10 min. The cuvette is placed in an electroporation apparatus such as, for example, an ECM 830 (from BTX Instrument Division, Harvard Apparatus, Holliston, Mass.). The cells are electroporated with a single pulse of approximately 2.4 milliseconds in length and a field strength of approximately 2.0 kV/cm. Alternatively, electroporation of red blood cells may be carried out using double pulses of 2.2 kV delivered at 0.25 µF using a Bio-Rad Gene Pulsar apparatus (Bio-Rad, Hercules, Calif., USA) to achieve a loading capacity of over 60% (Flynn et al., *Cancer Lett.* 82:225-229 (1994)). The cuvette is returned to the ice bath for 10-60 min and then placed in a 37° C. water bath to induce resealing of the cell membrane.

For sonication, for example, modified red blood cells are exposed to high intensity sound waves, causing transient disruption of the cell membrane allowing the therapeutic agent to diffuse into the cell.

For detergent treatment, for example, modified red blood cells are treated with a mild detergent which transiently compromises the cell membrane by creating holes, for example, through which the therapeutic agent may diffuse. After cells are loaded, the detergent is washed from the cells. For example, the detergent may be saponin.

For receptor mediated endocytosis, the modified red blood cell may have a surface receptor which upon binding of the therapeutic agents induce internalization of the receptor and the associated therapeutic agent.

In an embodiment, the therapeutic agent may be loaded into a modified red blood cell by fusing or conjugating the agent to proteins and/or peptides capable of crossing or translocating the plasma membrane (See, e.g., U.S. Patent Application 2002/0151004 A1). Examples of protein domains and sequences that are capable of translocating a cell membrane include, for example, sequences from the HIV-1-transactivating protein (TAT), the Drosophila Antennapedia homeodomain protein, the herpes simplex-1 virus VP22 protein, and transportin, a fusion between the neuropeptide galanin and the wasp venom peptide mastoparan. As such, a therapeutic agent may be fused or conjugated to all or part of the TAT peptide, for example. A fusion protein containing all or part of the TAT peptide and the therapeutic agent such as an antibody, enzyme, or peptide, for example, may be generated using standard recombinant DNA methods. Alternatively, all or part of the TAT peptide may be chemically coupled to a functional group associated with the therapeutic agent such as, for example, a hydroxyl, carboxyl or amino group. In some instances, the link between the TAT peptide and the therapeutic agent may be pH sensitive such that once the complex has entered the intracellular environment, the therapeutic agent is separated from the TAT peptide.

For mechanical firing, for example, the modified red blood cell may be bombarded with the therapeutic agent attached to a heavy or charged particle such as, for example, gold microcarriers and are mechanically or electrically accelerated such that they traverse the cell membrane. Microparticle bombardment of this sort may be achieved using, for example, the Helios Gene Gun (from, e.g., Bio-Rad, Hercules, Calif., USA).

Alternatively, the modified red blood cell may be loaded with a therapeutic agent by fusion with a synthetic vesicle such as, for example, a liposome. In this instance, the vesicles themselves are loaded with the therapeutic agent using one or more of the methods described herein. Alternatively, the therapeutic agent may be loaded into the vesicles during vesicle formation. The loaded vesicles are then fused with the modified red blood cells under conditions that enhance cell fusion. Fusion of a liposome, for example, with a cell may be facilitated using various inducing agents such as, for example, proteins, peptides, polyethylene glycol (PEG), and viral envelope proteins or by changes in medium conditions such as pH (See, e.g., U.S. Pat. No. 5,677,176).

For filtration, the modified red blood cell and the therapeutic agent may be forced through a filter of pore size smaller than the red blood cell causing transient disruption of the cell membrane and allowing the therapeutic agent to enter the cell.

For freeze thawing, the modified red blood cells are sent through several freeze thaw cycles, resulting in cell membrane disruption (See, e.g., U.S. Patent Application 2007/0243137 A1). In this instance, a pellet of packed red blood cells (0.1-1.0 ml) is mixed with an equal volume (0.1-1.0 ml) of an isotonic solution (e.g., phosphate buffered saline) containing the therapeutic agent. The red blood cells are frozen by immersing the tube containing the cells and therapeutic agent into liquid nitrogen, for example. Alternatively, the cells may be frozen by placing the tube in a freezer at –20° C. or –80° C., for example. The cells are then thawed in a 23° C. water bath and the cycle repeated if necessary to increase loading.

The therapeutic agent may be selected from a variety of known small molecule pharmaceuticals. Alternatively, the therapeutic agent may be an inactivating peptide nuclei acid (PNA), an RNA or DNA oligonucleotide aptamer, an interfering RNA (iRNA), a peptide, or a protein.

The therapeutic agent may be loaded into the cell in a solubilized form. As such, the therapeutic agent is solubilized in an appropriate buffer prior to loading into red blood cells.

Alternatively, the therapeutic agent may be loaded into red blood cells in a particulate form as a solid microparticulate (See, e.g., U.S. Patent Applications 2005/0276861 A1 and U.S. 2006/0270030 A1). In this instance, the therapeutic agent may be poorly water-soluble with a solubility of less than 1-10 mg/ml. As such, microparticles of less than 10 µm may be generated using a variety of techniques such as, for example, energy addition techniques such as milling (e.g., pearl milling, ball milling, hammer milling, fluid energy milling, jet milling), wet grinding, cavitation or shearing with a microfluidizer, and sonication; precipitation techniques such as, for example, microprecipitation, emulsion precipitation, solvent-antisolvent precipitation, phase inversion precipitation, pH shift precipitation, infusion precipitation, temperature shift precipitation, solvent evaporation precipitation, reaction precipitation, compressed fluid precipitation, protein microsphere precipitation; and other techniques such as spraying into cryogenic fluids (See, e.g., U.S. Patent Application 2005/0276861 A1). Water soluble molecules may also be used to form solid microparticles in the presence of various polymers such as, for example, polylactate-polyglycolate copolymer (PLGA), polycyanoacrylate, albumin, and/or starch (See, e.g., U.S. Patent Application 2005/0276861 A1). Alternatively, a water soluble molecule may be encapsulated in a vesicle to form a microparticle. The microparticles composed of the therapeutic agent may be incorporated into a modified red blood cell using the methods described herein.

A modified red blood cell loaded with a therapeutic agent may be administered intravenously, intramuscularly, subcutaneously, intradermally, intra-articularly, intrathecally, epidurally, intracerebrally, by buccal administration, rectally, topically, transdermally, orally, intranassaly, by pulmonary route, intraperitoneally, intra-opthalmically, or retro-orbitally. The cells may be administered by bolus injection, by intermittent infusion, or by continuous infusion, for example.

B. Molecular Agents

A variety of different agents may be loaded into red blood cells as described above. It will be appreciated that it is not necessary for a single agent to be used, and that it is possible to load two or more agents into a cell. Accordingly, the term "agent" also includes mixtures, fusions, combinations and conjugates, of atoms, molecules, etc. as disclosed herein. For example, an agent may include, but is not limited to, a nucleic acid combined with a polypeptide; two or more polypeptides conjugated to each other; a protein conjugated to a biologically active molecule (which may be a small molecule such as a prodrug); or a combination of a biologically active molecule with an imaging agent.

1. Therapeutic Agents

In an embodiment, the molecular agent is a therapeutic agent, such as a small molecule drug or biological effector molecule. For example, the therapeutic agent may be a biological effector molecule which has activity in a biological system. Biological effector molecules, include, but are not limited to, a protein, polypeptide, or peptide, including, but not limited to, a structural protein, an enzyme, a cytokine (such as an interferon and/or an interleukin), a polyclonal or monoclonal antibody, or an effective part thereof, such as an Fv fragment, which antibody or part thereof, may be natural, synthetic or humanized, a peptide hormone, a receptor, or a signaling molecule. Included within the term "immunoglobulin" are intact immunoglobulins as well as antibody fragments such as Fv, a single chain Fv (scFv), a Fab or a F(ab')$_2$.

Therapeutic agents of interest include, without limitation, pharmacologically active drugs, genetically active molecules, etc. Therapeutic agents of interest include antineoplastic agents, anti-inflammatory agents, hormones or hormone antagonists, ion channel modifiers, and neuroactive agents. Examples of therapeutic agents include those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (ed.), *Chemical Warfare Agents*, Academic Press, New York (1992)).

In an embodiment, the biological effector molecules are immunoglobulins, antibodies, Fv fragments, etc., that are capable of binding to antigens in an intracellular environment. These types of molecules are known as "intrabodies" or "intracellular antibodies." An "intracellular antibody" or an "intrabody" includes an antibody that is capable of binding to its target or cognate antigen within the environment of a cell, or in an environment that mimics an environment within the cell. Selection methods for directly identifying such "intrabodies" include the use of an in vivo two-hybrid system for selecting antibodies with the ability to bind to antigens inside mammalian cells. Such methods are described in PCT/GB00/00876, incorporated herein by reference. Techniques for producing intracellular antibodies, such as anti-β-galactosidase scFvs, have also been described in Martineau et al., *J Mol Biol* 280:117-127 (1998) and Visintin et al., *Proc. Natl. Acad. Sci. USA* 96:11723-1728 (1999).

In an embodiment, the biological effector molecule includes, but is not limited to, at least one of a protein, a polypeptide, a peptide, a nucleic acid, a virus, a virus-like an amino acid, an amino acid analogue, a modified amino acid, a modified amino acid analogue, a steroid, a proteoglycan, a lipid and a carbohydrate or a combination thereof (e.g., chromosomal material comprising both protein and DNA components or a pair or set of effectors, wherein one or more convert another to active form, for example catalytically).

A biological effector molecule may include a nucleic acid, including, but not limited to, an oligonucleotide or modified oligonucleotide, an antisense oligonucleotide or modified antisense oligonucleotide, an aptamer, a cDNA, genomic DNA, an artificial or natural chromosome (e.g., a yeast artificial chromosome) or a part thereof, RNA, including an siRNA, a shRNA, mRNA, tRNA, rRNA or a ribozyme, or a peptide nucleic acid (PNA); a virus or virus-like particles; a nucleotide or ribonucleotide or synthetic analogue thereof, which may be modified or unmodified.

The biological effector molecule can also be an amino acid or analogue thereof, which may be modified or unmodified or a non-peptide (e.g., steroid) hormone; a proteoglycan; a lipid; or a carbohydrate. If the biological effector molecule is a polypeptide, it can be loaded directly into a modified red blood cell, according to the methods described herein. Alternatively, a nucleic acid molecule bearing a sequence encoding a polypeptide, which sequence is operatively linked to transcriptional and translational regulatory elements active in a cell at a target site, may be loaded.

Small molecules, including inorganic and organic chemicals, may also be used. In an embodiment, the small molecule is a pharmaceutically active agent. Useful classes of pharmaceutically active agents include, but are not limited to, antibiotics, anti-inflammatory drugs, angiogenic or vasoactive agents, growth factors and chemotherapeutic (anti-neoplastic) agents (e.g., tumour suppressers).

If a prodrug is loaded in an inactive form, a second effector molecule may be loaded into a modified red blood cell, or a red blood cell that is to be modified according to the disclosure herein. Such a second effector molecule is usefully an activating polypeptide which converts the inactive prodrug to active drug form. In an embodiment, activating polypeptides include, but are not limited to, viral thymidine kinase (encoded by Genbank Accession No. J02224), carboxypeptidase A (encoded by Genbank Accession No. M27717), α-galactosidase (encoded by Genbank Accession No. M13571), β-gluucuronidase (encoded by Genbank Accession No. M15182), alkaline phosphatase (encoded by Genbank Accession No. J03252 J03512), or cytochrome P-450 (encoded by Genbank Accession No. D00003 N00003), plasmin, carboxypeptidase G2, cytosine deaminase, glucose oxidase, xanthine oxidase, β-glucosidase, azoreductase, t-gutamyl transferase, β-lactamase, or penicillin amidase.

Either the polypeptide or the gene encoding it may be loaded into the modified, or to-be-modified, red blood cells; if the latter, both the prodrug and the activating polypeptide may be encoded by genes on the same recombinant nucleic acid construct. Furthermore, either the prodrug or the activator of the prodrug may be transgenically expressed in hematopoietic stem cells and already loaded into the red blood cell. The relevant activator or prodrug (as the case may be) is then loaded as a second agent according to the methods described herein.

2. Imaging Agents

The agent may be an imaging agent, by which term is meant an agent which may be detected, whether in vitro or in vivo in the context of a tissue, organ or organism in which the agent is located. Examples of agents include those useful for imaging of tissues in vivo or ex vivo. For example, imaging agents, such as labeled antibodies which are specific for defined molecules, tissues or cells in an organism, may be used to image specific parts of the body by releasing from the loaded red blood cells at a desired location using electromagnetic radiation. This allows imaging agents which are not completely specific for the desired target, and which might otherwise lead to more general imaging throughout the organism, to be used to image defined tissues or structures. For example, in an embodiment, an antibody which is capable of imaging endothelial tissue is used to image endothelial cells in lower body vasculature, such as in the lower limbs, by releasing the antibody selectively in the lower body by applying ultrasound thereto. The electromagnetic energy will preferentially lyse the red blood cells in the desired target site, thereby achieving selective therapeutic effects with minimal damage to normal cells.

In an embodiment, the imaging agent emits a detectable signal, such as visible light or other electromagnetic radiation. In another embodiment, the imaging agent is a radioisotope, for example $^{32}P$ or $^{35}S$ or $^{99}Tc$, or a quantum dot, or a molecule such as a nucleic acid, polypeptide, or other molecule, conjugated with such a radioisotope. In an embodiment, the imaging agent is opaque to radiation, such as X-ray radiation. In another embodiment, the imaging agent comprises a targeting functionality by which it is directed to a particular cell, tissue, organ or other compartment within the body of an animal. For example, the agent may comprise a radiolabelled antibody which specifically binds to defined molecule(s), tissue(s) or cell(s) in an organism.

In an embodiment, the imaging agent is a contrast dye. For example, an MRI contrast agent can comprise a paramagnetic contrast agent (such as a gadolinium compound), a superparamagnetic contrast agent (such as iron oxide nanoparticles), a diamagnetic agent (such as barium sulfate), and combinations thereof. Metal ions preferred for MRI include those with atomic numbers 21-29, 39-47, or 57-83, and, more typically, a paramagnetic form of a metal ion with atomic numbers 21-29, 42, 44, or 57-83. Particularly preferred paramagnetic metal ions are selected from the group consisting of Gd(III), Fe(III), Mn(II and III), Cr(III), Cu(II), Dy(III), Tb(III and IV), Ho(III), Er(III), Pr(III) and Eu(II and III). Gd(III) is particularly useful. Note that as used herein, the term "Gd" is meant to convey the ionic form of the metal gadolinium; such an ionic form can be written as GD(III), GD3+, etc. with no difference in ionic form contemplated. A CT contrast agent can comprise iodine (ionic or non-ionic formulations), barium, barium sulfate, Gastrografin (a diatrizoate meglumine and diatrizoate sodium solution), and combinations thereof. In another embodiment, a PET or SPECT contrast agent can comprise a metal chelate.

IV. Incorporating Positive Marker(s) into Modified Red Blood Cells

The modified red blood cells may also be labeled with one or more positive markers that can be used to monitor over time the number or concentration of modified red blood cells in the blood circulation of an individual. It is anticipated that the overall number of modified red blood cells will decay over time following initial transfusion. As such, it may be appropriate to correlate the signal from one or more positive markers with that of the activated molecular marker, generating a proportionality of signal that will be independent of the number of modified red blood cells remaining in the circulation. There are presently several fluorescent compounds, for example, that are approved by the Food & Drug Administration for human use including but not limited to fluorescein, indocyanin green, and rhodamine B. For example, red blood cells may be non-specifically labeled with fluorescein isothiocyanate (FITC; Bratosin et al., Cytometry 46:351-356 (2001)). A solution of FITC-labeled lectins in phosphate buffered saline (PBS) with 0.2 mM phenylmethysulfonyl fluoride (PMSF) is added to an equal volume of isolated red blood cells in the same buffer. The cells are incubated with the FITC-labeled lectins for 1 h at 4° C. in the dark. The lectins bind to sialic acids and beta-galactosyl residues on the surface of the red blood cells.

It is anticipated that other dyes may be useful for tracking modified red blood cells in human and non-human circulation. A number of reagents may be used to non-specifically label a red blood cell. For example red blood cells may be labeled with PKH26 Red (See, e.g., Bratosin, et al., (1997) Cytometry 30:269-274). Red blood cells ($1-3\times10^7$ cells) are suspended in 1 ml of "diluent C" and rapidly added to 1 ml or 2 µM PKH26 dissolved in "diluent C". The mixture is mixed by gentle pipetting and incubated at 25° C. for 2-5 min with constant stirring. The labeling may be stopped by adding an equal volume of human serum or compatible protein solution (e.g., 1% bovine serum albumin). After an additional minute, an equal volume of cell culture medium is added and the cells are isolated by centrifugation at 2000×g for 5 min, for example. Cells are washed three times by repeated suspension in cell culture medium and centrifugation. PHK26-labeled cells may be monitored with a maximum excitation wavelength of 551 nm and a maximum emission wavelength of 567 nm.

VivoTag 680 (VT680; VisEn Medical, Woburn, Mass., USA) may be used to track cells in vivo. VT680 is a near-infrared fluorochrome with a peak excitation wavelength of 670±5 nm and a peak emission wavelength of 688±5 nm. VT680 also contains an amine reactive NHS ester which enables it to cross-link with proteins and peptides. As such, the surface of cells may be labeled with VT680 (See, e.g., Swirski, et al., (2007) PloS ONE 10:e1075). For example, $4\times10^6$ cells/ml are incubated with VT680 diluted in complete culture medium at a final concentration of 0.3 to 300 µg/ml for 30 min at 37° C. The cells are washed twice with complete culture medium after labeling. Cells may be non-specifically labeled based on proteins expressed on the surface of the modified red blood cell. Alternatively, a specific protein may be labeled with VT680. In some instances, an antibody directed against a specific protein associated with the modified red blood cell may be used to selectively label cells. In other instances, a protein or peptide may be directly labeled with VT680 ex vivo and subsequently either attached to the surface of the cell or incorporated into the interior of the cell using methods described here in for the uptake of nucleic acids.

In vivo monitoring, for example, may be performed using, for example, the dorsal skin fold. As such, laser scanning microscopy may be performed using, for example, an Olympus IV 100 in which VT680 is excited with a red laser diode of 637 nm and detected with a 660/LP filter. Alternatively, multiphoton microscopy may be performed using, for example, a BioRad Radiance 2100 MP centered around an Olympus BX51 equipped with a 20×/0.95 NA objective lens and a pulsed Ti:Sapphire laser tuned to 820 nm. The latter wavelength is chosen because VT680 has a peak in its two-photon cross-section at 820 nm.

Alternatively, a modified red blood cell may be labeled with other red and/or near-infrared dyes including, for example, cyanine dyes such as Cy5, Cy5.5, and Cy7 (Amersham Biosciences, Piscataway, N.J., USA) and/or a variety of Alexa Fluor dyes including Alexa Fluor 633, Alexa Fluor 635, Alexa Fluor 647, Alexa Fluor 660, Alexa Fluor 680, Alexa Fluor 700 and Alexa Fluor 750 (Molecular Probes-Invitrogen, Carlsbad, Calif., USA). Additional fluorophores include IRD41 and IRD700 (LI-COR, Lincoln, Nebr., USA), NIR-1 and 1C5-OSu (Dejindo, Kumamotot, Japan), LaJolla Blue (Diatron, Miami, Fla., USA), FAR-Blue, FAR-Green One, and FAR-Green Two (Innosense, Giacosa, Italy), ADS 790-NS and ADS 821-NS (American Dye Source, Montreal, Calif.). Quantum dots (Qdots) of various emission/excitation properties may also be used for labeling cells (See, e.g., Jaiswal et al., *Nature Biotech.* 21:47-51 (2003)). Many of these fluorophores are available from commercial sources either attached to primary or secondary antibodies or as amine-reactive succinimidyl or monosuccinimidyl esters, for example, ready for conjugation to a protein or proteins either on the surface or inside the red blood cells.

Magnetic nanoparticles may be used to track cells in vivo using high resolution MRI (Montet-Abou et al., *Molecular Imaging* 4:165-171 (2005)). Magnetic particles may be internalized by several mechanisms. Magnetic particles may be taken up by a cell through fluid-phase pinocytosis or phagocytosis. Alternatively, the magnetic particles may be modified to contain a surface agent such as, for example, the membrane translocating HIV that peptide which promotes internalization. In some instances, a magnetic nanoparticle such as, for example, Feridex IV®, an FDA approved magnetic resonance contrast reagent, may be internalized into hematopoietic cells in conjunction with a transfection agent such as, for example, protamine sulfate (PRO), polylysine (PLL), and lipofectamine (LFA).

V. Formulations of Pharmaceutical Compositions

The modified red blood cells can be incorporated into pharmaceutical compositions suitable for administration. The pharmaceutical compositions generally comprise substantially purified modified red blood cells and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (See, e.g., Remington's Pharmaceutical Sciences, Mack Publishing Co., Easton, Pa. 18$^{th}$ ed. (1990)). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and include materials are capable of administration to or upon a subject without the production of undesirable physiological effects to a degree that would prohibit administration of the composition. For example, "pharmaceutically-acceptable excipient" includes an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

Examples of such carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the modified red blood cells, use thereof in the compositions is contemplated. Supplementary active compounds can also be incorporated into the compositions.

A pharmaceutical composition is formulated to be compatible with its intended route of administration. The modified red blood cells can be administered by parenteral, topical, intravenous, oral, subcutaneous, intraarterial, intradermal, transdermal, rectal, intracranial, intraperitoneal, intranasal; intramuscular route or as inhalants. The modified red blood cells can optionally be administered in combination with other agents that are at least partly effective in treating various diseases including various actin- or microfilament-related diseases.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the modified red blood cells in the required amount in an appropriate solvent with one or a combination of ingredients enumerated above, as required. Generally, dispersions are prepared by incorporating the modified red blood cells into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The modified red blood cells can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the modified red blood cells can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the modified red blood cells are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the modified red blood cells are formulated into ointments, salves, gels, or creams as generally known in the art.

The modified red blood cell an also be prepared as pharmaceutical compositions in the form of suppositories (e.g., with conventional suppository bases such as cocoa butter and other glycerides) or retention enemas for rectal delivery.

In an embodiment, the modified red blood cells are prepared with carriers that will protect the modified red blood cells against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

Methods of Use

I. General Methods of Targeting Cells or Tissues

This section will generally describe an embodiment of the methods of using the modified red blood cell compositions. Further details of particular applications are described in the sections that follow.

In one aspect, the disclosure provides methods of using a modified red blood cell to bind a target molecule, thereby localizing the modified red blood cell to a particular location (e.g., tissue or cell) within a subject. In an embodiment, the fusion protein is configured to facilitate fusion of the red blood cell with the target cell. In other embodiments, upon binding of the target recognition moiety to the target molecule, the complex becomes activated. As such, a singlet oxygen molecule can be delivered to the particular location (e.g., tissue or cell) by exposing the area to light of a suitable wavelength. The disclosure also provides for methods of using a modified red blood cell to bring a target cell or tissue in contact with a molecular agent, which is carried by the modified red blood cell. In an embodiment, the modified red blood cells may be useful for the treatment of infection (e.g., bacterial, fungal, viral or parasitic) or for the treatment of cancer or other hyperproliferative disorders (e.g., restenosis or benign prostatic hyperplasia), by damaging or destroying the target cells.

As shown in FIG. 1, a target-binding agent 100 is composed of a target recognition moiety 105, a photoactivatable molecule 110, and a quencher molecule 115. In the absence of a target, the photoactivatable molecule 110 is in close proximity to the quencher molecule 115 and is not responsive by light. In the presence of a target 120, an activated unit 125 is generated. As such, the target recognition moiety 105 undergoes a conformational change 130. The quencher molecule 115 moves away from the photoactivatable molecule 110, resulting in an activated photoactivatable molecule 135. In response to light energy 140, the activated photoactivatable molecule 135 emits a reactive singlet oxygen 145.

Figure 2:
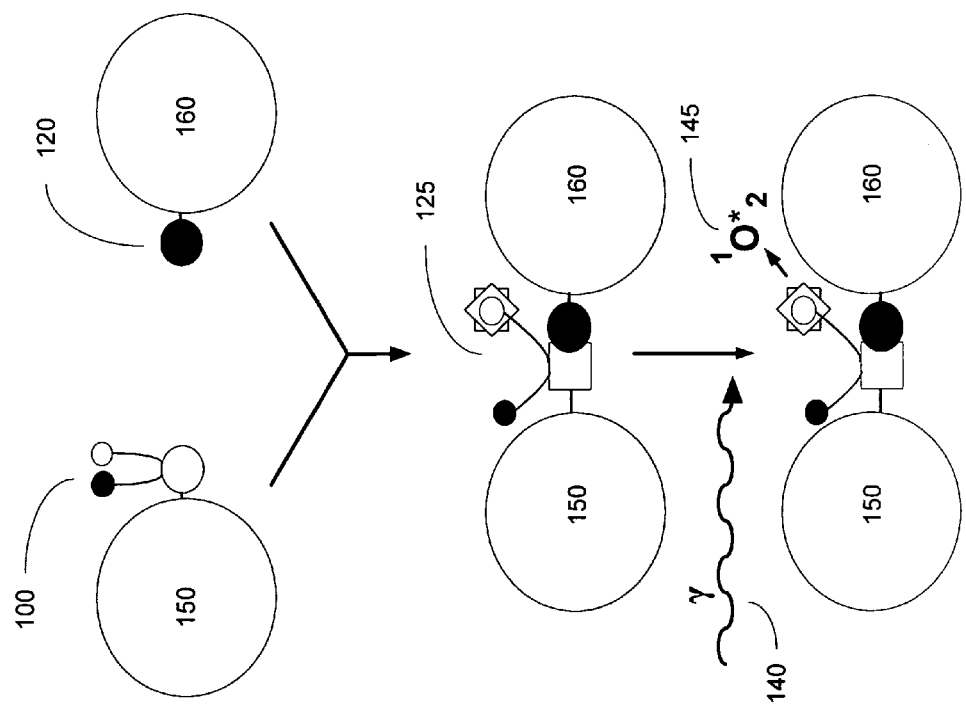
FIG. 2 is a schematic diagram illustrating the interaction of a modified red blood cell with a target cell. The target-binding agent is activated upon binding to the target cell and singlet oxygen radical species is generated upon exposure to electromagnetic radiation of a suitable wavelength and power.

As shown in FIG. 2, one or more red blood cells 150 may be modified with a target-binding agent 100 to form a modified red blood cell. The modified red blood cells can be released into the blood circulation of the subject. In circulation, the one or more modified red blood cells 150 may come into contact with a target cell 160 which expresses on its surface, for example, a target 120 recognized by the target recognition moiety of the target-binding agent. The target cell 160 may be a pathogen such as for example a bacterium, a fungus, or a parasite. Alternatively, the target cell 160 may be a cancerous cell such as for example a leukemia cell, a circulating tumor cell (CTC), or other cancerous cell. Upon binding, the target-binding agent is converted into an activated unit. In response to light energy 140, the activated unit 125 releases a reactive singlet oxygen 145.

Figure 3:
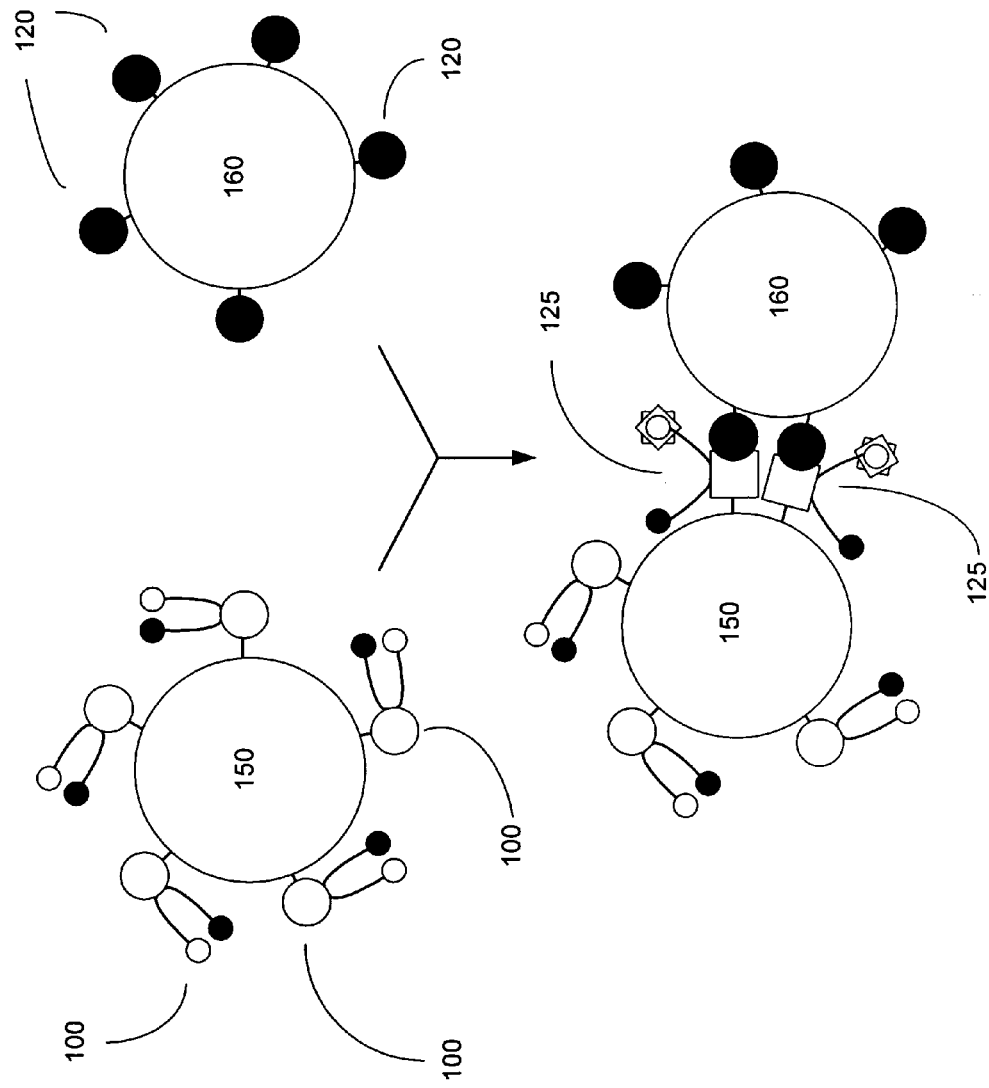
FIG. 3 is a schematic diagram illustrating the interaction of multiple target-binding agents with a target cell. The target-binding agents are activated upon binding to the target cell.

As shown in FIG. 3, one or more red blood cells 150 may be modified with one or more target-binding agents 100 to form a modified red blood cell. Similarly, one or more target cells 160 may have one or more targets 120 recognized by the target-binding agent 100. As such, one or more targets 120 may bind to one or more target-binding agents 100 to generate one or more activated units 125.

Figure 4:
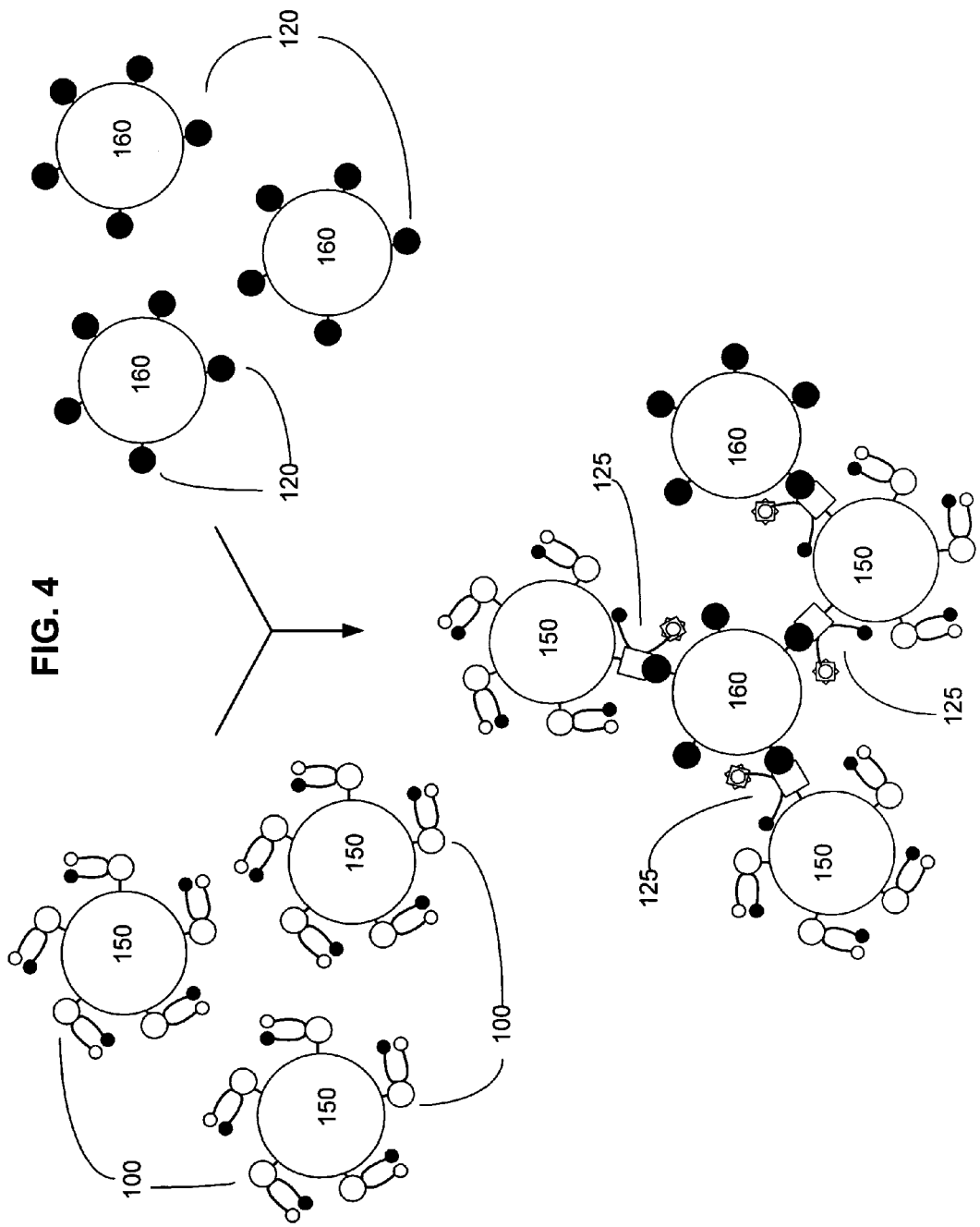
FIG. 4 is a schematic diagram illustrating the interaction of a population of modified red blood cells with a population of target cells. The target-binding agent is activated upon binding to the target cell.

As shown in FIG. 4, one or more modified red blood cells 150 modified with one or more target-binding agents 100 may interact with one or more target cells 160 with one or more targets 120 recognized by the target-binding agent 100. As such, one or more modified red blood cells 150 may interact with one or more target cells. Singlet oxygen may produce cellular damage. Since the singlet oxygen has a very short lifetime (microseconds), the photodamage can be expected to be within a short radius of the target molecule.

Figure 5:
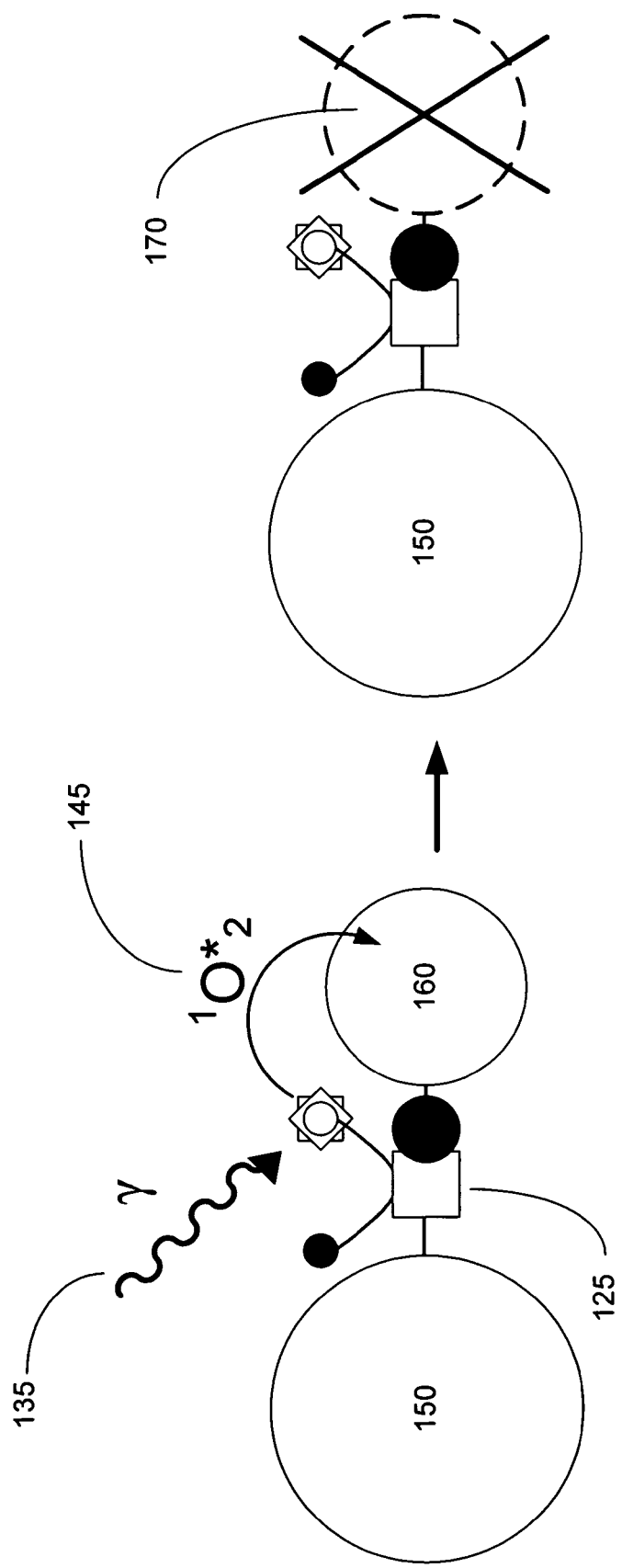
FIG. 5 is a schematic diagram illustrating the interaction of a modified red blood cell with a target cell. Exposure of the activated target-binding agent to the electromagnetic radiation of a suitable wavelength and power produces a singlet oxygen radical molecule which, in turn, results in damage or death to the target cell.

As shown in FIG. 5, upon binding of a modified red blood cell 150 to a target cell 160, the target-binding agent is converted into the activated unit 125. The activated unit 125 may now be excited by light energy 135 resulting in release of a reactive singlet oxygen 145. The reactive singlet oxygen 145 may, in turn, interact with the target cell 160. The reactive singlet oxygen 145 may cause apoptosis and/or necrosis of the target cell 160 leading to a dead or inactivated target cell 170.

Figure 6:
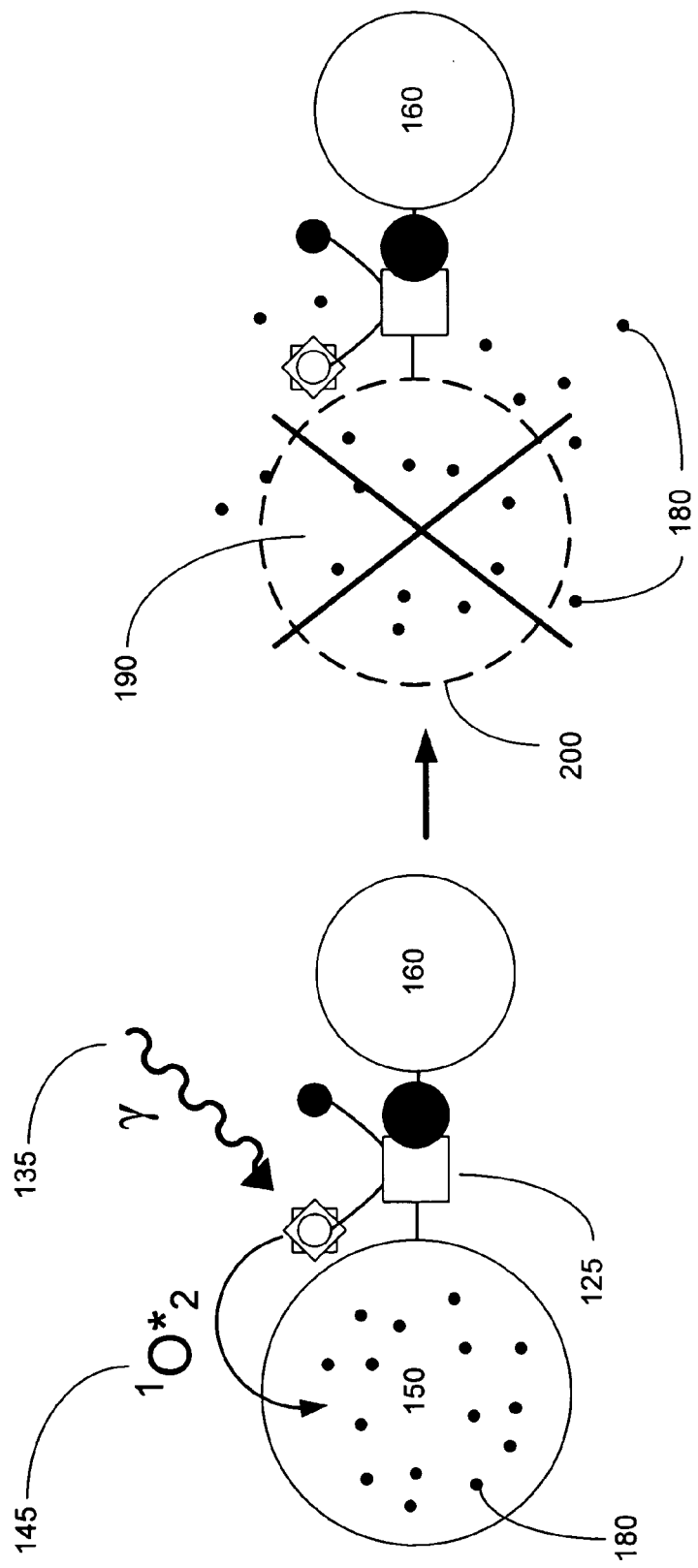
FIG. 6 is a schematic diagram illustrating the interaction of a modified red blood cell with a target cell. The target-binding agent is activated upon binding of the target recognition moiety to the target molecule. Exposure of the activated target-binding agent to electromagnetic radiation of a suitable wavelength produces a singlet oxygen radical molecule which results in lysis of the modified red blood cell and release of one or more therapeutic agents.

As shown in FIG. 6, in some instances, the modified red blood cells 150 may be loaded with a therapeutic agent 180. A therapeutic agent 180 may be a small molecule drug, a biological drug such as, for example, an antibody, a ligand, a receptor and/or an enzyme, or an oligonucleotide such as, for example, an RNA or DNA aptamer, an interfering RNA, and/or an antisense RNA. Upon binding of a modified red blood cell 150 to a target cell 160, the target-binding agent is converted into the activated unit 125. The activated unit 125 may now be excited by light energy 135 resulting in release of a reactive singlet oxygen 145. The reactive singlet oxygen 145 may, in turn, interact with the modified red blood cell 150. The reactive singlet oxygen 145 may cause apoptosis and/or necrosis of the modified red blood cell 150 resulting in a dead or inactivated red blood cell 190. The inactivated modified red blood cell 190 releases the therapeutic agent through the compromised cell membrane 200 in proximity of the target cell 160.

Figure 7:
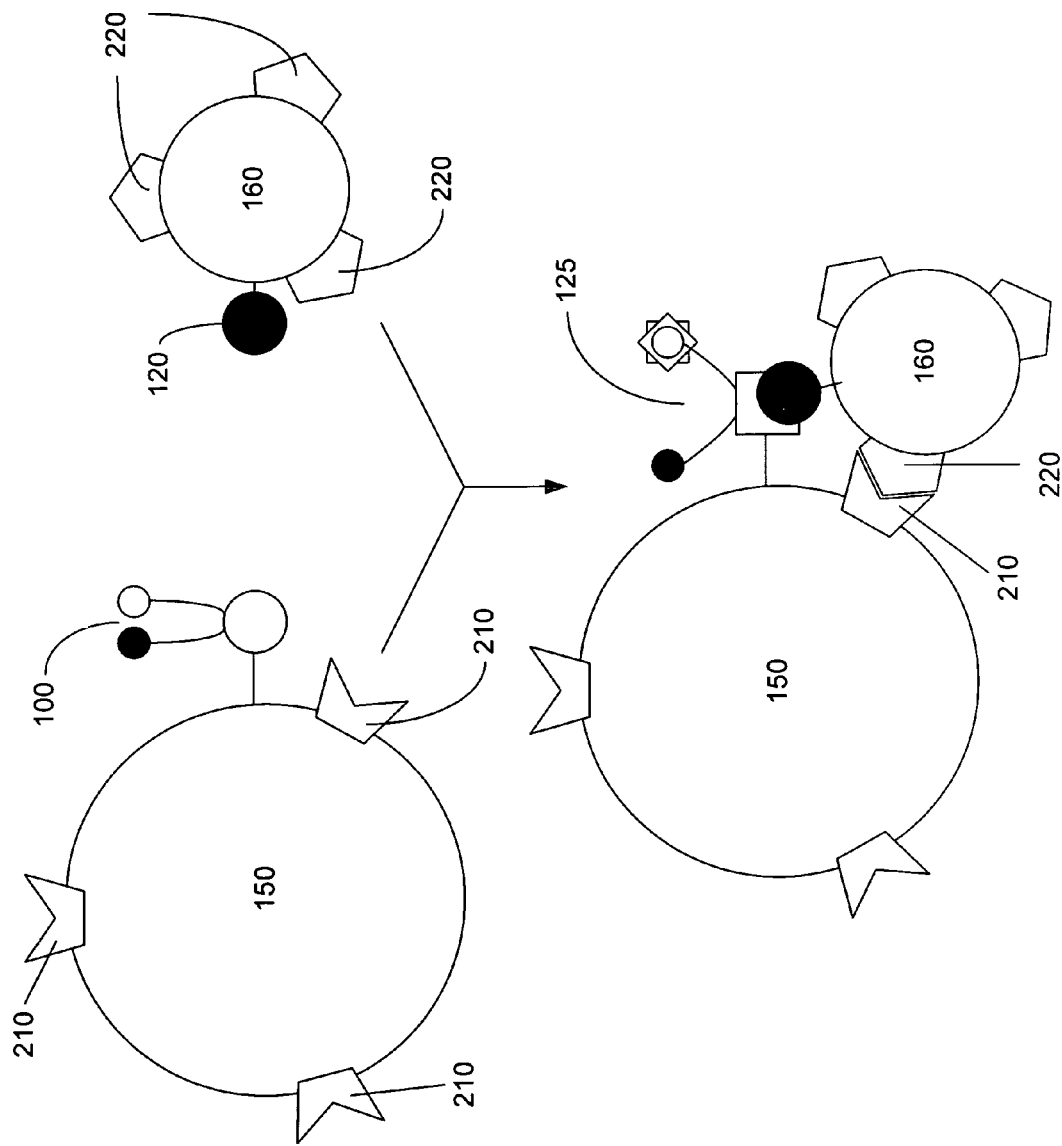
FIG. 7 is a schematic diagram illustrating the interaction of a modified red blood cell with a target cell. The modified red blood cell comprises multiple target recognition moieties on its surface.

As shown in FIG. 7, in some instances, the modified red blood cells 150 comprising one or more target-binding agents 100 may also be modified with another target recognition moiety 210. The target recognition moiety 210 may recognize a receptor 220 on the target cell 160. The target recognition moiety 210 and the receptor 220 may be an antibody and an antigen, respectively. Alternatively, the target recognition moiety 210 and the receptor 220 may be a ligand/receptor pair. As such, modified red blood cells 150 and one or more target cells 160 may interact through the target-binding agent 100 and the target 120 to form the activated unit 125, through the target recognition moiety 210 and the receptor 220, or through a combination of both to facilitate a more selective interaction, for example.

Figure 8:
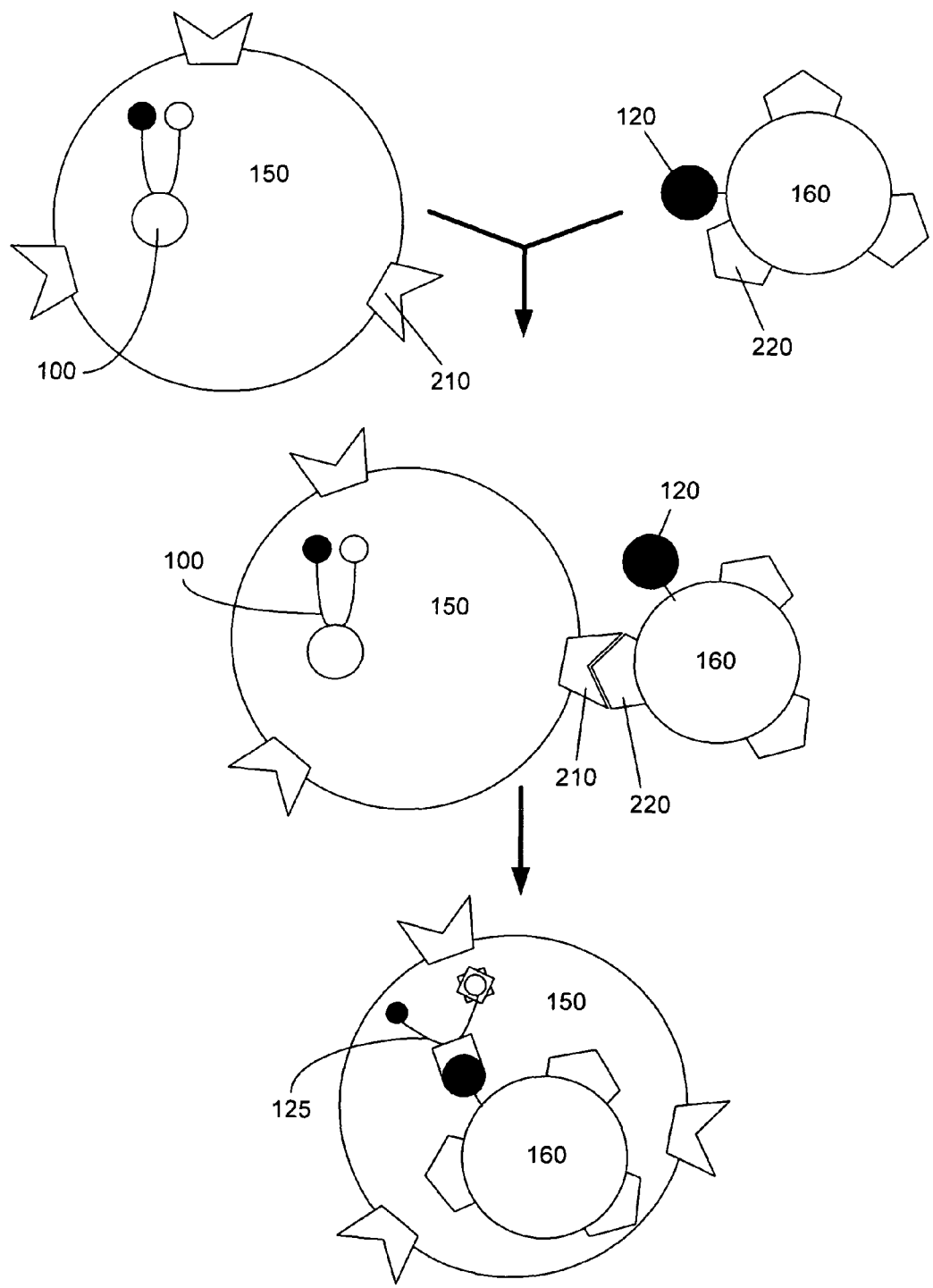
FIG. 8 is a schematic diagram illustrating the interaction of a modified red blood cell with a target cell. The target cell becomes internalized within the modified red blood cell, thereby activating the target recognition moiety of the target-binding agent.

As shown in FIG. 8, in some instances, one or more target-binding agents 100 may be loaded into the cytoplasm, for example, of one or more red blood cells 150 to form a modified red blood cell. The modified red blood cell may be further modified with another target recognition moiety 210. The target recognition moiety 210 may recognize a receptor 220 on the target cell 160. In some instances, the interaction of the target recognition moiety 210 and the receptor 220 may lead to fusion and/or invasion of the red blood cell 150 by the target cell 160. As such, the modified red blood cell 150 may take up the target cell 160. Inside the modified red blood cell 150, the target cell 120 may interact with the target-binding agent 100 to generate the activated unit 125. The internalized target cell 160 may then be damaged or destroyed when the activated unit is exposed to light of an appropriate wavelength and power and a singlet oxygen radical molecule is produced.

Figure 9:
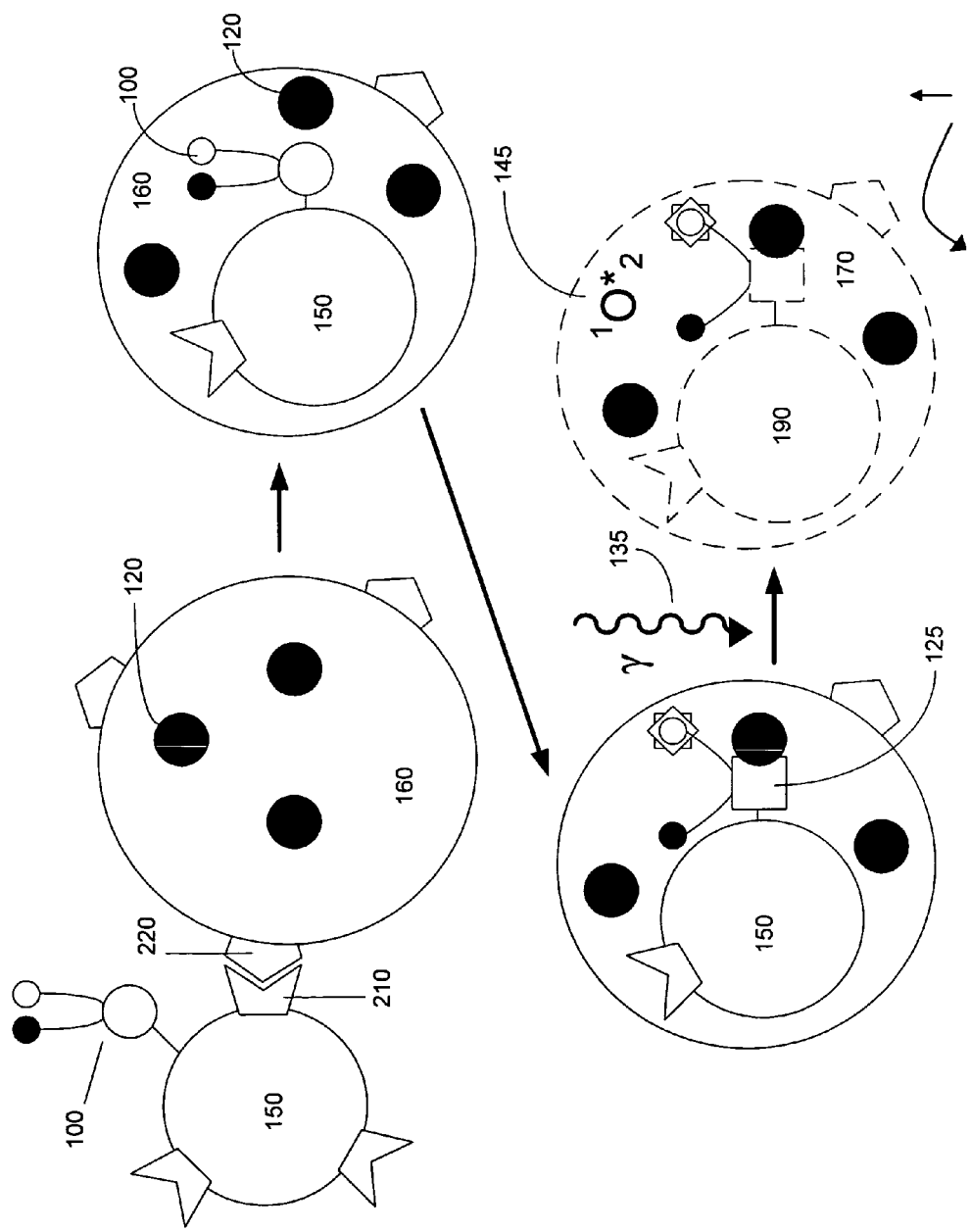
FIG. 9 is a schematic diagram illustrating the interaction of a modified red blood with a target cell. The modified red blood cell becomes internalized into the target cell, where target molecules become bound to the target-binding agent, thereby activating the target recognition moiety of the target-binding agent.

As shown in FIG. 9, in some instances, the modified red blood cells 150 modified with one or more target-binding agent 100 may also be modified with another target recognition moiety 210. The target recognition moiety 210 may recognize a receptor 220 on the target cell 160. In some instances, the interaction of the target recognition moiety 210 and the receptor 220 may lead to fusion of the red blood cell 150 and the target cell 160. Inside the target cell 160, the target-binding agent 100 may interact with the target 120 to generate the activated unit 125. Upon radiation with light energy 135, the activated unit 125 emits reactive singlet oxygen leading to a damaged or destroyed target cell 170 and/or damaged or destroyed red blood cell 190.

Figure 10:
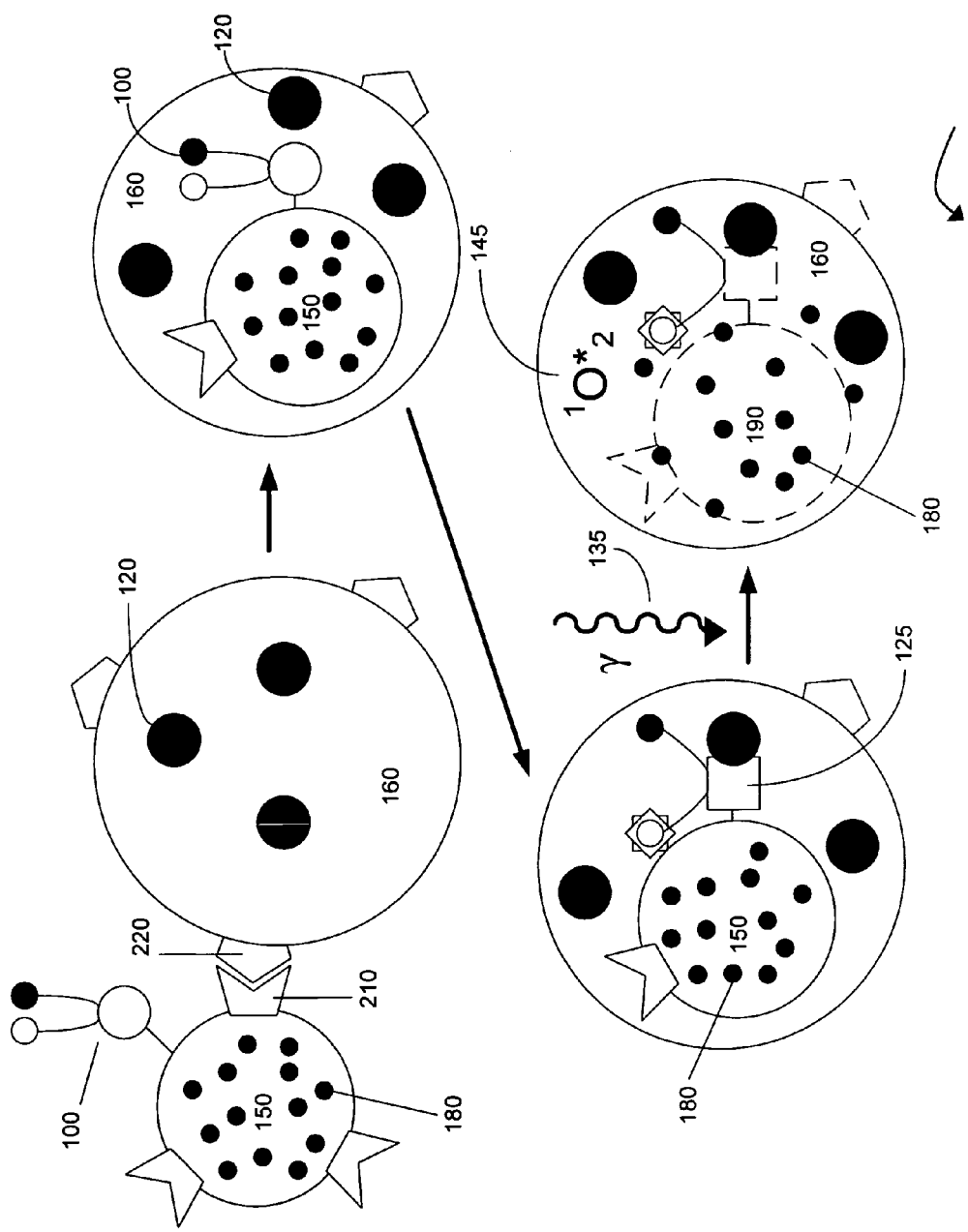
FIG. 10 is a schematic diagram illustrating the interaction of a modified red blood cell with a target cell. The modified red blood cell becomes internalized into the target cell, where target molecules become bound to the target-binding agent, thereby activating the target recognition moiety of the target-binding agent. The activated target-binding agent produces a singlet oxygen radical molecule when it is exposed to electromagnetic radiation of a suitable wavelength and power, which results in lysis of the modified red blood cell and release of one or more therapeutic agents.

As shown in FIG. 10, in some instances, the modified red blood cell 150 modified with one or more target-binding agent 100 and one or more target recognition moiety 210 may be loaded with a therapeutic agent 180. The target recognition moiety 210 may recognize a receptor 220 on the target cell 160. In some instances, the interaction of the target recognition moiety 210 and the receptor 220 may lead to fusion of the red blood cell 150 and the target cell 160. Inside the target cell 160, the target-binding agent 100 may interact with the target 120 to generate the activated unit 125. Upon radiation with light energy 135, the activated unit 125 emits reactive singlet oxygen leading to damaged or destroyed red blood cell 190 and release of the therapeutic agent 180 into the cytoplasm of the target cell 160.

A. Excitation of the Photoactivatable Molecule

In an embodiment, the one or more methods optionally include providing electromagnetic energy to the subject, where the electromagnetic energy is configured to induce a response from the photoactivatable molecules associated with the modified red blood cells. In illustrative embodiments, excitation of the one or more photoactivatable molecules directly and/or indirectly damages the target cell and/or the red blood cell.

In illustrative embodiments, the electromagnetic energy includes, but is not limited to, one or more frequencies having one or more characteristics that taken as a whole are not considered unduly harmful to the subject. In illustrative examples, such electromagnetic energy may include frequencies optionally including visible light (detected by the human eye between approximately 400 nm and 700 nm) as well as infrared (longer than 700 nm) and limited spectral regions of ultraviolet light, such as UVA light (between approximately 320 nm and 400 nm). Electromagnetic energy includes, but is not limited to, single photon electromagnetic energy, two photon electromagnetic energy, multiple wavelength electromagnetic energy, and extended-spectrum electromagnetic energy.

Electromagnetic energy may be configured as a continuous beam or as a train of short pulses. In the continuous wave mode of operation, the output is relatively consistent with respect to time. In the pulsed mode of operation, the output varies with respect to time, optionally having alternating "on" and "off" periods. Electromagnetic energy may be provided by one or more lasers, for example, having one or more of a continuous or pulsed mode of action. One or more pulsed lasers may include, but are not limited to, Q-switched lasers, mode locking lasers, and pulsed-pumping lasers. Mode locked lasers emit extremely short pulses on the order of tens of picoseconds down to less than 10 femtoseconds, the pulses optionally separated by the time that a pulse takes to complete one round trip in the resonator cavity. Due to the Fourier limit, a pulse of such short temporal length may have a spectrum which contains a wide range of wavelengths.

In an embodiment, the electromagnetic energy is focused at a depth of approximately 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, or 3.0 mm below the surface of the skin, beyond the surface of a wall of a blood vessel (e.g., in the blood vessel lumen), and/or beyond a surface of an internal location. In an embodiment, the electromagnetic energy is focused at a depth of approximately 0.1 to 3 mm, 0.1 to 2.5 mm, 0.1 to 2.0 mm, 0.1 to 1.5 mm, 0.1 to 1.0 mm, 0.1 to 0.5 mm, 0.5 to 3.0 mm, 0.5 to 2.5 mm, 0.5 to 2.0 mm, 0.5 to 1.5 mm, 0.5 to 1.0 mm, 1.0 to 3.0 mm, 1.0 to 2.5 mm, 1.0 to 2.0 mm, 1.0 to 1.5 mm, 1.5 to 3.0 mm, 1.5 to 2.5 mm, 1.5 to 2.0 mm, 2.0 to 3.0 mm, 2.0 to 2.5 mm, or 2.5 to 3.0 mm below the surface of the skin, beyond the surface of a wall of a blood vessel (e.g., in the blood vessel lumen), and/or beyond a surface of an internal location.

In an embodiment, the electromagnetic energy is generated by two photons having the same wavelength or substantially the same wavelength. In an embodiment, the electromagnetic energy is generated by sets of two photons having different wavelengths. Electromagnetic energy at the energy levels of the two photons is optionally focused at a depth below the surface of the skin, beyond the surface of a wall of a blood vessel (e.g., in the blood vessel lumen), and/or beyond a surface of an internal location, and/or optionally at one or more depths. As used herein, the term "two-photon" may include excitation optionally using one or more femtosecond lasers. In an embodiment, two photon electromagnetic energy is coupled through a virtual energy level and/or coupled through an intermediate energy level.

As used herein, the term "extended-spectrum" may include a range of possible electromagnetic radiation wavelengths within the full spectrum of possible wavelengths, optionally from extremely long to extremely short and optionally including wide spectrum and narrow spectrum wavelengths.

In an embodiment, the electromagnetic energy may be defined spatially and/or directionally. In an embodiment, the electromagnetic energy may be spatially limited, optionally spatially focused and/or spatially collimated. In an embodiment, the electromagnetic energy may be directionally limited, directionally varied, and/or directionally variable. In illustrative embodiments, the electromagnetic energy optionally contacts less than an entire possible area, or less than an entire possible target, and/or is limited to a certain depth within a tissue. In illustrative embodiments, the electromagnetic energy is spatially and/or directionally limited so that only areas approximately bounded by the walls of one or more blood vessels are provided with electromagnetic energy. In illustrative embodiments, the electromagnetic energy may be provided over an entire field (e.g., scanning across and/or the length of a blood vessel lumen), through movement of the electromagnetic source, and/or through illumination from more than one, two, three, four, and/or multiple sources in the device. Alternatively, in some approaches illumination may be provided over less than an entire field, for example, by illuminating according to a vector scanning approach. In such approaches, illumination energy may be directed to less than all of the area, e.g., primarily in and/or around vascular regions or in areas of interest, such as areas where blood components of interest may be suspected to be or predicted to be. Alternatively, such illumination of less than the entire region may be implemented by a scanning pattern encompassing the entire region combined with activating the source of electromagnetic energy only in selected locations.

B. Methods for Disrupting Modified Red Blood Cells Loaded with Molecular Agents

A modified red blood cell loaded with a molecular agent (e.g., a therapeutic agent) may be targeted to a specific pathogen or cell using the methods described herein. Upon interacting with the target cell, the modified red blood cell may be induced to release the therapeutic agent. There are a number of methods described for controlled release of a therapeutic agent from a red blood cell such as, for example, normal red blood cell break down, accelerated red blood cell breakdown due, for example, to incompatible cells from different individuals or species, inappropriate blood type, and/or introduction of immunogenic protein on the surface of the red blood cell, administering energy to selectively disrupt red blood cells such as, for example, ultrasound, radiofrequency, microwave, and/or infrared, incorporation of an enzyme that digests the cell membrane from the inside out, addition of a second agent added at a specific time the initiates cell breakdown, and use of the complement system (See, e.g., U.S. Patent Application 2007/0243137 A1).

In some instances, it may be of benefit to target macrophages with the modified red blood cells. Under normal circumstances, aged and/or damaged red blood cells are cleared from circulation by macrophage phagocytosis. This process may be enhanced by artificially clustering the modified red blood cell transmembrane proteins using, for example, $ZnCl_2$ and bissulfosuccinimideilsuberate ($BS^3$; See, e.g., U.S. Pat. No. 6,139,836). In this instance, the modified red blood cells are treated with 1 mM $ZnCl_2$ in saline solution to cluster the proteins and subsequently treated with $BS^3$ for 15 min to irreversibly cross-link the clustered proteins.

A modified red blood cell may be loaded with metal particles which upon interaction with an external energy source preferentially causes the modified red blood cells to be disrupted (See, e.g., U.S. Pat. No. 6,645,464). As such, modified red blood cells may be loaded with colloidal gold or gold clusters (1-20 nm in size) using hypotonic lysis in 5 mM phosphate buffer (pH 8) with 10 µM magnesium sulfate at a temperature of 4° C. In some instances, the modified red blood cells may be simultaneously loaded with metal particles and a therapeutic agent, for example. The cells are resealed by warming to 37° C. for 5-15 min in the presence of 0.2 M NaCl, for example. In some instances, it may be beneficial to add small nucleating metal particles to a modified red blood cell and subsequently enlarging the particles in situ (See, e.g., U.S. Pat. No. 6,645,464). As such, modified red blood cells that have been loaded with small nucleating metal particles and resealed may be further treated with an autometallographic developer solution containing gold ions, for example, to generate large internal metal particles. The modified red blood cells may be targeted to a specific tissue bed such as, for example, a tumor, and subsequently irradiated to disrupt the modified red blood cell and release the loaded therapeutic agent.

C. Monitoring Interaction of Modified Red Blood Cell with Target Molecule

In an embodiment, it may be useful to monitor the interaction of the modified red blood cells with a target molecule or target cell prior to the exposure of a subject to light of a suitable wavelength. The interaction may be monitored by providing a modified red blood cell which includes a signaling molecule that is detectable upon binding of the modified red blood cell to the target cell or molecule.

In an embodiment, red blood cells may be modified with an aptamer-based molecular beacon to detect interaction of the modified red blood cell with a target cell. RNA or DNA oligonucleotide-based aptamers in combination with fluorescent tags, for example, may be used as molecular beacons to detect interactions between a modified red blood cell and molecules on the surface of a pathogen and/or cancerous cell. Aptamers specific for virtually any class of molecules may be isolated from a large library of $10^{14}$ to $10^{15}$ random oligonucleotide sequences using an iterative in vitro selection procedure often termed "systematic evolution of ligands by exponential enrichment" (SELEX; Cao et al., *Current Proteomics* 2:31-40 (2005); Proske et al., *Appl. Microbiol. Biotechnol.* 69:367-374 (2005)).

Molecular beacons may be dual labeled aptamer probes with a donor fluorophore at one end and an acceptor fluorophore or quencher at the other end. Upon binding of a specific target, the aptamer is configured to undergo a conformational shift such that the distance between the donor fluorophore and the acceptor fluorophore or quencher is altered, leading to a change in detectable fluorescence. This phenomenon is referred to as fluorescence resonance energy transfer (FRET). FRET is a distance-dependent interaction between the electronic excited states of two dye molecules in which excitation is transferred from a donor molecule to an acceptor molecule without emission of a photon. In some instances, interaction of a donor molecule with an acceptor molecule may lead to a shift in the emission wavelength associated with excitation of the acceptor molecule. In other instances, interaction of a donor molecule with an acceptor molecule may lead to quenching of the donor emission. As such, an aptamer-based molecular beacon may be used to monitor changes in the fluorescent properties of the aptamer-based molecular beacon in response to binding a chemical entity such as, for example, a molecule on the surface of a target cell.

A variety of donor and acceptor fluorophore pairs may be considered for FRET associated with an aptamer-based molecular beacon including, but not limited to, fluorescein and tetramethylrhodamine; IAEDANS and fluorescein; fluorescein and fluorescein; and BODIPY FL and BODIPY FL. A number of Alexa Fluor (AF) fluorophores (from Molecular Probes-Invitrogen, Carlsbad, Calif., USA) may be paired with other AF fluorophores for use in FRET. Some examples include AF 350 with AF 488; AF 488 with AF 546, AF 555, AF 568, or AF 647; AF 546 with AF 568, AF 594, or AF 647; AF 555 with AF594 or AF647; AF 568 with AF6456; and AF594 with AF 647.

Red blood cells may be modified with a cell-surface receptor that signals either directly or indirectly in response to ligand binding. As an example, a G-protein-coupled receptor (GPCR) associated with a modified red blood cell may be used as an activatable molecular marker to monitor binding of a modified red blood cell to a target. The vast majority of GPCRs internalize from the cell surface into acidic endosomes in response to agonist challenge (Milligan, *DDT* 8:579-585 (2003)). As such, a GPCR may be labeled with a pH sensitive dye which upon entering the acidic environment of the endosome changes its emission properties. The GPCR may be labeled with CypHer5™, for example, which is a red-excited, pH-sensitive cyanine dye that is non-fluorescent at pH 7.4 and maximally fluorescent at pH 5.5 and is ideally suited for monitoring internalization of GPCRs (available from Amersham Biosciences, Piscataway, N.J., USA). CypHer5™ may be attached to a protein by conjugation of CypHer5™ mono NHS ester to amine groups on the surface of the protein (See, e.g., Adie et al., *Biotechniques* 33:1152-1157 (2002)). In the case of labeling a GPRC or other cell surface receptor, the receptor may be directly labeled with CypHer5™. Alternatively, a GPCR may be indirectly labeled by interaction with a CypHer5™ labeled antibody specific for that receptor (See, e.g., Adie et al., Biotechniques 33:1152-1157 (2002)). CypHer5™ signaling is monitored at an emission wavelength of 695 nm using an excitation wavelength of 633 nm. Other pH sensitive dyes that might be used for labeling a GPCR or other cell surface receptor include but are not limited to fluoroscein isothiocyanate (FITC), 1,4(and 5)-benzenedicarboxylic acid, 2-[10-(dimethylamino)-4-fluoro-3-oxo-3H-benzo[ c]xanthen-7-yl] (carboxy SNARF-4F), 2',7'-Bis(2-carboxylethyl)-5(6)-carboxyfluorescein (BCECF).

II. Methods of Treatment

In an aspect, one or more methods of treatment include providing one or more modified red blood cells to a subject; wherein the one or more modified red blood cells are associated with one or more target recognition moieties. In an aspect, one or more methods of treatment include providing one or more modified red blood cells to a subject; wherein the one or more modified red blood cells include one or more target recognition moieties. In an embodiment, the target recognition moieties are designed to recognize one or more neoplastic cells or pathogens. In an embodiment, activation of the target-binding agent and subsequent excitation of the photoactivatable molecule may cause release of a therapeutic agent (e.g., an antibiotic or chemotherapeutic agent) from the modified red blood cell. In other embodiments, the modified red blood cells include one or more fusion molecules that are designed to participate in a fusion of the modified red blood cells with the target cells.

Briefly, the modified red blood cells are administered to the subject before the target tissue, target composition or subject is subjected to electromagnetic radiation. The composition may be administered in a pharmaceutical formulation as described above. The dose of the modified red blood cells for an optimal therapeutic benefit can be determined clinically. A certain length of time is allowed to pass for the circulating or locally delivered modified red blood cells to be taken up by the target tissue. The unbound modified red blood cells are cleared from the circulation during this waiting period, or additional time can optionally be provided for clearing of the unbound modified red blood cells from non-target tissue. The waiting period will be determined clinically and may vary depending on the composition of the composition.

At the conclusion of this waiting period, a light source is used to excite the bound photoactivatable molecule. The light source may provide non-coherent (non-laser) or coherent (laser) light. For example, non-coherent light sources include, but are not limited to, mercury or xenon arc lamps with optical filters, tungsten lamps, cold cathode fluorescent lamps, halogen lamps, light emitting diodes (LEDs), LED arrays, incandescent sources, and other electroluminescent devices. Lamp sources are used when fine definition of the illumination region is not required, or when a large region is to be illuminated. Focused non-coherent light can be used to illuminate small regions, such as by using lenses to focus the light or optical fibers to direct or deliver the light. Laser sources are usually used to illuminate small, well-defined regions, because of their higher specific radiance and more readily controlled beam properties. Coherent light sources include, but are not limited to, dye lasers, argon ion lasers, laser diodes, tunable lasers, Ti-sapphire lasers, Ruby lasers, Alexandrite lasers, Helium-Neon lasers, GaAlAs and InGaAs diode lasers, Nd-YLF lasers, Nd-glass lasers, Nd-YAG lasers and fiber lasers. For example, lasers are often used as excitation sources in confocal equipment, and to create very high flux. Laser sources are limited in that they emit a restricted, often discrete set of wavelengths in contrast to lamps, which generally produce a continuous spectrum that can be filtered to provide any desired band within a certain range.

The area of illumination is determined by the location and dimension of the pathologic region to be detected, diagnosed or treated. The duration of illumination period will depend on whether detection or treatment is being performed, and can be determined empirically. A total or cumulative period of time anywhere from between about 1 min and 72 h can be used. In an embodiment, the illumination period is between about 4 min and 48 h. In another embodiment, the illumination period is between about 30 min and 24 h.

The total fluence (i.e., power) or energy of the light used for irradiating is from about 10 Joules and about 25,000 Joules; in an embodiment, the total fluence is from about 100 Joules and about 20,000 Joules or from about 500 Joules and about 10,000 Joules. Light of a wavelength and fluence sufficient to produce the desired effect is selected, whether for detection by fluorescence or for therapeutic treatment to destroy or impair a target tissue or target cell. Light having a wavelength corresponding at least in part with the characteristic light absorption wavelength of the photosensitizing agent is used for irradiating the target issue.

The power delivered by the light used is measured in watts, where 1 watt is equal to 1 joule/sec. Intensity is the power per area. Thus, intensity may be measured in watts/cm$^2$. Therefore, the intensity of the light used for irradiating may be between about 5 mW/cm² to about 500 mW/cm². Since the total fluence or amount of energy of the light in Joules is divided by the duration of total exposure time in seconds, the longer the amount of time the target is exposed to the irradiation, the greater the amount of total energy or fluence may be used without increasing the amount of the intensity of the light used. The methods typically employ an amount of total fluence of irradiation that is sufficiently high to excite the photoactivatable molecule of the target-binding agent.

In an embodiment of using the modified red blood cells disclosed herein for photodynamic therapy, the modified red blood cells are injected into the mammal, e.g., human, to be diagnosed or treated. The level of injection is usually between about 0.1 and about 0.5 μmol/kg of body weight. In the case of treatment, the area to be treated is exposed to light at the desired wavelength and energy, e.g., from about 10 to 200 J/cm². In the case of detection, fluorescence is determined upon exposure to light at a wavelength sufficient to cause the target-binding agent to fluoresce at a wavelength different than that used to illuminate the conjugate. The energy used in detection is sufficient to cause fluorescence and is usually significantly lower than is required for treatment.

The following sections will describe particular diseases or conditions that may be treated using the modified red blood cells.

A. Methods of Treating Cancer and Other Hyperproliferative Disorders

A neoplasm or tumor is an abnormal tissue growth resulting from neoplastic cells, i.e., cells that proliferate more rapidly and uncontrollably than normal cells. Usually partially or completely structurally disorganized, neoplasms lack functional coordination with the corresponding normal tissue. Neoplasms usually form a distinct tissue mass that may be either benign (tumor) or malignant (cancer). In addition to structural disorganization, cancer cells usually regress to more primitive or undifferentiated states (anaplasia), although morphologically and biochemically, they may still exhibit many functions of the corresponding wild-type cells. Carcinomas are cancers derived from epithelia; sarcomas are derived from connective tissues. In some cases, cancers may not be associated with a tumor, but like the affected tissue, is defuse, e.g., leukemias.

The modified red blood cells may be used to target neoplastic cells and designate those cells for damage or destruction. For example, the photoactivatable molecule of the modified red blood cells may act upon the neoplastic cells directly by bringing the cells in contact with singlet oxygen. Alternatively, the modified red blood cells may comprise red blood cells loaded with one or more therapeutic agents, e.g., a chemotherapeutic or antineoplastic agent, which is released from the modified red blood cell at the desired location. Consequently, the neoplastic cell is brought into close contact with a relatively high concentration of the therapeutic agent.

As described above, the modified red blood cells may be loaded with one or more chemotherapeutic agents for targeted delivery to a neoplastic cell. Examples of chemotherapeutic or antineoplastic agents include, but are not limited to, an alkylating agent; cisplatin; carboplatin; oxaliplatin; mechlorethamine; cyclophosphamide; chlorambucil; antimetabolite compound; azathioprine; mercaptopurine; alkaloids; terpenoids; vinca alkaloid; vincristine; vinblastine; vinorelbine; vindesine; podophyllotoxin; taxanes; taxol; docetaxel; paclitaxel; topoisomerase inhibitors; camptothecins; irinotecan; topotecan; amsacrine; etoposide; etoposide phosphate; and teniposide; epipodophyllotoxins; antitumour antibiotics; dactinomycin; trastuzumab (Herceptin), cetuximab, and rituximab (Rituxan or Mabthera); Bevacizumab (Avastin); finasteride; tamoxifen; gonadotropin-releasing hormone agonists (GnRH); and goserelin.

B. Methods of Treating a Pathogen Infections

1. Bacterial Infections

Bacteremia is the presence of bacteria in the blood. Bacteremia has many possible causes, including dental procedures or even vigorous toothbrushing; catheterization of an infected lower urinary tract; surgical treatment of an abscess or infected wound; and colonization of indwelling devices, especially IV and intracardiac catheters, urethral catheters, and ostomy devices and tubes. Gram-negative bacteremia secondary to infection usually originates in the GU or GI tract, or the skin in patients with decubitus ulcers. Chronically ill and immunocompromised patients have an increased risk of gram-negative bacteremia. They may also develop bacteremia with gram-positive cocci, anaerobes, and fungi. *Staphylococcal* bacteremia is common in injection drug users. *Bacteroides* bacteremia may develop in patients with infections of the abdomen and the pelvis, particularly the female genital tract.

Metastatic infection of the meninges or serous cavities, such as the pericardium or larger joints, can result from transient or sustained bacteremia. Metastatic abscesses may occur almost anywhere. Multiple abscess formation is especially common with staphylococcal bacteremia. Bacteremia may cause endocarditis, most commonly if the pathogen is an *Enterococcus, Streptococcus,* or *Staphylococcus,* and less commonly with gram-negative bacteremia and fungemia. Patients with valvular heart disease, prosthetic heart valves, or other intravascular prostheses are predisposed to endocarditis, which may occur after certain dental procedures. Staphylococci can cause gram-positive bacterial endocarditis, particularly in injection drug users, and may involve the tricuspid valve. The bacteria most likely to cause bacteremia include members of the *Staphylococcus, Streptococcus, Pseudomonas, Haemophilus,* and *Esherichia coli* (*E. coli*) genera.

Bacterial diseases or disorders that can be treated or prevented by the use of the modified red blood cells include, but are not limited to, Mycobacteria, Rickettsia, Mycoplasma, *Neisseria meningitides, Neisseria gonorrheoeae, Legionella, Vibrio cholerae, Streptococci, Staphylococcus aureus, Staphylococcus epidermidis, Pseudomonas aeruginosa, Corynobacteria diphtheriae, Clostridium* spp., enterotoxigenic *Eschericia coli,* and *Bacillus anthracis*. Other pathogens for which bacteremia has been reported at some level include the following: *Rickettsia, Bartonella henselae, Bartonella quintana, Coxiella burnetii, chlamydia, Mycobacterium leprae, Salmonella; shigella; Yersinia enterocolitica; Yersinia pseudotuberculosis; Legionella pneumophila; Mycobacterium tuberculosis; Listeria monocytogenes; Mycoplasma* spp.; *Pseudomonas fluorescens; Vibrio cholerae; Haemophilus influenzae; Bacillus anthracis; Treponema pallidum; Leptospira; Borrelia; Corynebacterium diphtheriae; Francisella; Brucella melitensis; Campylobacter jejuni; Enterobacter; Proteus mirabilis; Proteus;* and *Klebsiella pneumoniae.*

A red blood cell may be modified with a moiety that allows the cell to target bacteria existing in the blood or at precise locations within the body. A target recognition moiety may be, for example, an antibody, antibody fragment, single chain antibody, DNA and/or RNA oligonucleotide, leptin, peptide, peptide nucleic acid (PNA), protein, receptor, drug, ligand, enzyme, and/or substrate, that is capable of specifically binding a target molecule associated with a bacteria.

In an embodiment, a red blood cell may be modified with a targeting antibody that specifically recognizes and targets the modified red blood cell to bacteria (See, e.g., U.S. Pat. No. 6,506,381 B1; U.S. Patent Application 2004/0033232 A1; U.S. Patent Application 2006/0018912 A1). The targeting antibody directed against a specific marker on the surface of the target cell may be generated using standard procedures. Alternatively, the targeting antibody may be commercially available.

One or more red blood cells may be modified with a target recognition moiety that is a cellular receptor that recognizes and/or binds to bacteria. For example, CD14, which is normally associated with monocyte/macrophages is known to bind lipopolysaccharide associated with gram negative bacteria as well as lipoteichoic acid associated with the gram positive bacteria *Bacillus subtilis* (See, e.g., Fan et al., *Infect. Immun.* 67:2964-2968 (1999)). Other examples of cellular receptors include but are not limited to adenylate cyclase (*Bordatella pertussis*), Gal alpha 1-4Gal-containing isoreceptors (*E. coli*), glycoconjugate receptors (enteric bacteria), Lewis(b) blood group antigen receptor (*Heliobacter pylori*), CR3 receptor, protein kinase receptor, galactose N-acetylgalactosamine-inhibitable lectin receptor, and chemokine receptor (*Legionella*), annexin I (*Leishmania mexicana*), ActA protein (*Listeria monocytogenes*), meningococcal virulence associated Opa receptors (Meningococcus), α5β3 integrin (*Mycobacterium avium*-M), heparin sulphate proteoglycan receptor, CD66 receptor, integrin receptor, membrane cofactor protein, CD46, GM1, GM2, GM3, and CD3 (*Neisseria gonorrhoeae*), KDEL receptor (*Pseudomonas*), epidermal growth factor receptor (*Samonella typhiurium*), β1 integrin (*Shigella*), and nonglycosylated J774 receptor (*Streptococci*) (See, e.g., U.S. Patent Application 2004/0033584 A1).

A modified red blood cell may include an antibody or aptamer that binds a specific bacterium of interest. As such, the antibody may bring the red blood cell into close proximity to the bacteria. The red blood cell may be further modified with an additional component that has the ability to breach the outer membrane/cell wall of the bacterium such as, for example, lysozymes, bacteriocidal permeability increasing peptides, and other pore forming antimicrobials (See, e.g., U.S. Pat. No. 6,506,381 B1). For example, Zaitsev et al., (Blood 108:1895-1902 (2006)) describe methods for modifying a red blood cell with a serine protease by linking the protease to an antibody to CR1, an abundant protein component of the red blood cell membrane. In this instance, the serine protease, tissue plasminogen activator (tPA), attached to the red blood cells retained its enzymatic activity in vivo. As such, lysozyme which hydrolyses 1,4-beta-linkages between N-acetylmuramic acid and N-acetyl-D-glucosamine residues in a peptidoglycan and between N-acetyl-D-glucosamine residues in chitodextrins of some bacteria may be similarly attached to the surface of a modified red blood cell through conjugation to a red blood cell binding antibody, for example. Alternatively, lysozyme may be expressed on the surface of a modified red blood cell as part of a membrane associated fusion protein, for example. Fusion proteins containing lysozyme have been described (See, e.g., U.S. Pat. Nos. 5,993,809 and 7,045,677). In addition, fusion proteins have been described that include a secreted protein that is retained in association with the exterior of a cell by fusion to a protein with a membrane anchor domain (See, e.g., U.S. Patent Application 2006/0068388 A1).

Alternatively, a modified red blood cell may include an antibody or aptamer that binds a specific bacterium of interest. In addition, the modified red blood cell may include one or more additional antibodies and/or aptamers to which is reversibly attached a therapeutic agent (See, e.g., U.S. Patent Application 2003/0215454 A1). In some instances, the red blood cell binds to its target and due to the concave nature of the red blood cell creates a small volume of space into which a subset of the therapeutic agent may diffuse to establish an equilibrium. As therapeutic agent is taken up by the target cell, more therapeutic agent is released from the modified red blood cell.

The modified red blood cell may be modified with an antibody and/or aptamer, for example, that specifically binds a target cell. Upon binding to the modified red blood cell, the target cell is immobilized and may be cleared in accordance with the body's red blood cell clearing mechanism through the phagocytic cells of the reticuloendothelial system.

In some instances, a therapeutic agent may be selectively released from a modified red blood cell using ultrasound energy. For example, red blood cells that have been sensitized with an electrical field are more sensitive to ultrasound-induced disruption of the cell membrane than normal, untreated red blood cells (See, e.g., U.S. Patent Application 2004/0071664). As such, modified red blood cells loaded with a therapeutic agent may be sensitized ex vivo with an electrical field prior to transfusion of the cells into an individual. The sensitizing electrical field may be as strong as that used for electroporation of a therapeutic agent into a modified red blood cell. Alternatively, lower electrical field strengths may be used. In general, electrical field strengths may range, for example, from about 0.1 kVolts/cm to about 10 kVolts/cm (See, e.g., U.S. Patent Applications 2002/0151004 A1 and 2004/0071664 A1). Ultrasound energy with a power density ranging from 0.05 to 100 W cm$^{-2}$ and frequency ranging from 0.015 to 10.0 MHz over a time frame ranging from 10 milliseconds to 60 minutes may be used to disrupt the sensitized red blood cells and induce release of the loaded therapeutic agent (See, e.g., U.S. Patent Application 2004/0071664). The sensitization step may be combined with the loading step using a specific device such as that described in U.S. Pat. No. 6,495,351 B2.

Examples of therapeutic agents (i.e., antibiotics) include, but are not limited to, beta-lactam compounds (penicillin, methicillin, nafcillin, oxacillin, cloxacillin, dicloxacilin, ampicillin, ticarcillin, amoxicillin, carbenicillin, piperacillin); cephalosporins & cephamycins (cefadroxil, cefazolin, cephalexin, cephalothin, cephapirin, cephradine, cefaclor, cefamandole, cefonicid, cefuroxime, cefprozil, loracarbef, ceforanide, cefoxitin, cefmetazole, cefotetan, cefoperazone, cefotaxime, ceftazidine, ceftizoxine, ceftriaxone, cefixime, cefpodoxime, proxetil, cefdinir, cefditoren, pivoxil, ceftibuten, moxalactam, cefepime); other beta-lactam drugs (aztreonam, clavulanic acid, sulbactam, tazobactam, ertapenem, imipenem, meropenem); cell wall membrane active agents (vancomycin, teicoplanin, daptomycin, fosfomycin, bacitracin, cycloserine); tetracyclines (tetracycline, chlortetracycline, oxytetracycline, demeclocycline, methacycline, doxycycline, minocycline, tigecycline); macrolides (erythromycin, clarithromycin, azithromycin, telithromycin); clindamycin; choramphenicol; quinupristin-dalfopristin; linezolid; aminoglycosides (streptomycin, neomycin, kanamycin, amikacin, gentamicin, tobramycin, sisomicin, netilmicin); spectinomycin; sulfonamides (sulfacytine, sulfisoxazole, silfamethizole, sulfadiazine, sulfamethoxazole, sulfapyridine, sulfadoxine); trimethoprim; pyrimethamine; trimethoprim-sulfamethoxazole; fluoroquinolones (ciprofloxacin, gatifloxacin, gemifloxacin, levofloxacin, lomefloxacin, moxifloxacin, norfloxacin, ofloxacin); colistimethate sodium, methenamine hippurate, methenamine mandelate, metronidazole, mupirocin, nitrofurantoin, and polymyxin B. Examples of anti-mycobacteria drugs include, but are not limited to: isoniazid, rifampin, rifabutin, rifapentine, pyrazinamide, ethambutol, ethionamide, capreomycin, clofazimine, and dapsone.

2. Methods of Treating Fungal Infection

Fungemia (also known as candidemia, candedemia, and invasive candidiasis) is the presence of fungi or yeasts in the blood. The most commonly known pathogen is *Candida albicans*, causing roughly 70% of fungemias, followed by *Candida glabrata* with 10%, and *Aspergillus* with 1%. However, the frequency of infection by *T. glabrata, Candida tropicalis, C. krusei*, and *C. parapsilosis* is increasing, especially when significant use of fluconazole is common.

A red blood cell may be modified with a moiety that allows the cell to target fungal cells in the subject's body. A target recognition moiety may be, for example, an antibody, antibody fragment, single chain antibody, DNA and/or RNA oligonucleotide, leptin, peptide, peptide nucleic acid (PNA), protein, receptor, drug, ligand, enzyme, and/or substrate, that is capable of specifically binding a target molecule associated with a fungal cell.

In an embodiment, a red blood cell may be modified with a targeting antibody that specifically recognizes and targets the modified red blood cell to fungi. The targeting antibody directed against a specific marker on the surface of the target cell may be generated using standard procedures. Alternatively, the targeting antibody may be commercially available.

In an embodiment, a modified red blood cell may be loaded with an antifungal agent that is released upon contact with the fungal cell. Examples of antifungal agents includes, but is not limited to: allylamines; terbinafine; antimetabolites; flucytosine; azoles; fluconazole; itraconazole; ketoconazole; ravuconazole; posaconazole; voriconazole; glucan synthesis inhibitors; caspofungin; micafungin; anidulafungin; polyenes; amphotericin B; amphotericin B Lipid Complex (ABLC); amphotericin B Colloidal Dispersion (ABCD); liposomal amphotericin B (L-AMB); liposomal nystatin; and griseofulvin.

3. Methods of Treating a Parasitic Infection

In an embodiment, the modified red blood may be administered to a subject for the treatment of a parasitic infection. The targeting compositions may be directed to intestinal or blood-borne parasites, including protazoa. Typically, blood-borne parasites are transmitted through an arthropod vector. Most important arthropod for transmitting parasitic infections are mosquitoes. Mosquitoes carry malaria and filarial nematodes. Biting flies transmit African trypanosomiasis, leishmaniasis and several kinds of filariasis. Examples of parasites include, but are not limited to, trypanosomes; haemoprotozoa and parasites capable of causing malaria; enteric and systemic cestodes including taeniid cestodes; enteric coccidians; enteric flagellate protozoa; filarial nematodes; gastrointestinal and systemic nematodes and hookworms.

A red blood cell may be modified with a moiety that allows the cell to target the parasite or particular cells of the parasite. A target recognition moiety may be, for example, an antibody, antibody fragment, single chain antibody, DNA and/or RNA oligonucleotide, leptin, peptide, peptide nucleic acid (PNA), protein, receptor, drug, ligand, enzyme, and/or substrate, that is capable of binding a target molecule associated with the parasite.

In an embodiment, a red blood cell may be modified with a targeting antibody that recognizes and targets the red blood cell to the parasite. The targeting antibody directed against a marker on the surface of the target may be generated using standard procedures. Alternatively, the targeting antibody may be commercially available.

In an embodiment, a modified red blood cell may be loaded with an anti-parasitic agent that is released upon contact with the parasite. Examples of anti-parasitic drugs include, but are not limited to: antiprotozoal agents; eflornithine; furazolidone; melarsoprol; metronidazole; ornidazole; paromomycin sulfate; pentamidine; pyrimethamine; tinidazole; antimalarial agents; quinine; chloroquine; amodiaquine; pyrimethamine; sulphadoxine; proguanil; mefloquine; halofantrine; primaquine; artemesinin and derivatives thereof; doxycycline; clindamycin; benznidazole; nifurtimox; antihelminthics; albendazole; diethylcarbamazine; mebendazole; niclosamide; ivermectin; suramin; thiabendazole; pyrantel pamoate; levamisole; piperazine family; praziquantel; triclabendazole; octadepsipeptides; and emodepside.

4. Methods of Treating a Viral Infection

In an embodiment, the modified red blood may be administered to a subject for the treatment of a viral infection. A red blood cell may be modified with a moiety that allows the cell to target the virus or host cells of the virus. A target recognition moiety may be, for example, an antibody, antibody fragment, single chain antibody, DNA and/or RNA oligonucleotide, leptin, peptide, peptide nucleic acid (PNA), protein, receptor, drug, ligand, enzyme, and/or substrate, that is capable of specifically binding a target molecule associated with the virus.

In an embodiment, a red blood cell may be modified with a targeting antibody that specifically recognizes and targets the red blood cell to the virus. The targeting antibody directed against a specific marker on the surface of the virus may be generated using standard procedures. Alternatively, the targeting antibody may be commercially available. For example, the target recognition moieties of the modified red blood cells may be directed to clinically important viruses, including but not limited to adenovirus, coxsackievirus, hepatitis a virus, poliovirus, epstein-barr virus, herpes simplex, type 1, herpes simplex, type 2, human cytomegalovirus, human herpesvirus, type 8, varicella-zoster virus, hepatitis B virus, hepatitis C viruses, human immunodeficiency virus (HIV), influenza virus, measles virus, mumps virus, parainfluenza virus, respiratory syncytial virus, papillomavirus, rabies virus, and Rubella virus.

In an embodiment, a modified red blood cell may be loaded with an antiviral agent that is released upon contact with the virus. Examples of antiviral agents include: thiosemicarbazones; metisazone; nucleosides and nucleotides; acyclovir; idoxuridine; vidarabine; ribavirin; ganciclovir; famciclovir; valaciclovir; cidofovir; penciclovir; valganciclovir; brivudine; ribavirin, cyclic amines; rimantadine; tromantadine; phosphonic acid derivatives; foscarnet; fosfonet; protease inhibitors; saquinavir; indinavir; ritonavir; nelfinavir; amprenavir; lopinavir; fosamprenavir; atazanavir; tipranavir; nucleoside and nucleotide reverse transcriptase inhibitors; zidovudine; didanosine; zalcitabine; stavudine; lamivudine; abacavir; tenofovir disoproxil; adefovir dipivoxil; emtricitabine; entecavir; non-nucleoside reverse transcriptase inhibitors; nevirapine; delavirdine; efavirenz; neuraminidase inhibitors; zanamivir; oseltamivir; moroxydine; inosine pranobex; pleconaril; and enfuvirtide.

III. Diagnostic and Imaging Methods

In one aspect, the disclosure provides methods of using modified red blood cells to deliver an imaging agent to a cell or a tissue within a subject. In an embodiment, the modified red blood cells may be engineered to express or carry one or more molecular markers; wherein the one or more molecular markers are configured to be activated by interaction with one or more molecules to be detected. For example, an aptamer-based molecular beacon may be located in the cytoplasm of a red blood cell and detect changes in cellular signaling associated with interaction of a modified red blood cell with a target.

In another embodiment, the red blood cells are loaded with an imaging agent that emits a detectable signal, such as light or other electromagnetic radiation. In another embodiment, the imaging agent is a radio-isotope, for example $^{32}P$ or $^{35}S$ or $^{99}Tc$, or a molecule such as a nucleic acid, polypeptide, or other molecule, conjugated with such a radio-isotope. In an embodiment, the imaging agent is opaque to radiation, such as X-ray radiation. For example, the agent may comprise a radiolabelled antibody which specifically binds to defined molecule(s), tissue(s) or cell(s) in an organism.

In another embodiment, the imaging agent is a contrast dye. For example, an MRI contrast agent can comprise a paramagnetic contrast agent (such as a gadolinium compound), a superparamagnetic contrast agent (such as iron oxide nanoparticles), a diamagnetic agent (such as barium sulfate), and combinations thereof. Metal ions preferred for MRI include those with atomic numbers 21-29, 39-47, or 57-83, and, more typically, a paramagnetic form of a metal ion with atomic numbers 21-29, 42, 44, or 57-83. Particularly preferred paramagnetic metal ions are selected from the group consisting of Gd(III), Fe(III), Mn(II and III), Cr(III), Cu(II), Dy(III), Tb(III and IV), Ho(III), Er(III), Pr(III) and Eu(II and III). Gd(III) is particularly useful. Note that as used herein, the term "Gd" is meant to convey the ionic form of the metal gadolinium; such an ionic form can be written as GD(III), GD3+, etc. with no difference in ionic form contemplated. A CT contrast agent can comprise iodine (ionic or non-ionic formulations), barium, barium sulfate, Gastrografin (a diatrizoate meglumine and diatrizoate sodium solution), and combinations thereof. In another embodiment, a PET or SPECT contrast agent can comprise a metal chelate. Following administration of the contrast dye, the subject can be imaged using X-ray, MRI, CT, or PET scanning.

The compositions and methods described herein are further illustrated by the following examples, which should not be construed as limiting in any way.

EXAMPLES

Example 1

Treatment of a Hyperproliferative Disorder

In this example, the modified red blood cells are used to treat a hyperproliferative disorder (e.g., cancer). In one instance, the modified red blood cells are targeted to surface antigens on a neoplastic cell, known or suspected to be present in a subject's body. Upon excitation with light of the appropriate wavelength and power, singlet oxygen radicals are generated, resulting in damage or destruction of the neoplastic cell. In another instance, the modified red blood cells are used to deliver a therapeutic agent to the neoplastic cell(s).

A photoactivatable molecule, such as a porphyrin, is conjugated, via an amide linkage, to a monoclonal antibody known to exhibit selective binding to an antigen expressed on the surface of a neoplastic cell. The antibody is also conjugated to a quenching agent such as a Dabcyl (4-(4'-dimethylaminophenylazo)benzoyl) group, by reaction with a commercially available agent such as dabcyl chloride. This target-binding agent is further modified by the addition of a suitable metal ion to an aqueous solution of the composition. The metal binds to the coordination pocket of the porphyrin ring-system and also coordinates the amine or azo group of the quenching group, ensuring that the quenching agent remains sufficiently close to the photoactivatable molecule to allow energy transfer and thereby quench the generation of singlet oxygen.

Next, red blood cells are isolated from the subject in need of treatment. In cases where it is desirable to deliver a therapeutic agent to the neoplastic cells, the cells are loaded with a chemotherapeutic agent, such as 5-fluorouracil, and biotinylated. The antibody is also conjugated with biotin and then linked to the biotinylated red blood cells by a streptavidin bridge to form an assembled target-binding agent. The assembled target-binding agent is mixed with a suitable excipient for intravenous administration to the subject. A therapeutically effective amount of this target-binding agent is administered to the subject.

Binding of the antibody to its target then disrupts the coordination binding environment, releasing the quencher molecule from the metal and allowing the quencher molecule to move away from the photoactivatable molecule, thereby activating the target-binding agent. After a sufficient time for the target-binding agent to bind to the intended target and clear from normal tissue, a light source of the appropriate wavelength is used to deliver a therapeutically useful amount of light to an area that includes the lesion or region of hyperproliferative tissue. The light causes the excitation of the photoactivable moiety, resulting in the production of a singlet oxygen radical molecule. The singlet oxygen radical molecule may act directly on the neoplastic cell, thereby damaging or destroying the cell. Alternatively, the singlet oxygen radical disrupts the cell membrane of the red blood cell, thereby releasing the chemotherapeutic agent. The chemotherapeutic agent is contacted with the neoplastic cell causing cell death.

The efficacy of treatment is assessed by reduction in the number of neoplastic cells or absence of the neoplastic cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer.

Example 2

Treatment of a Pathogen Infection

In this example, the modified red blood cells are used to treat a pathogen infection (e.g., bacterial, fungal, viral or parasitic). In one instance, the modified red blood cells are targeted to surface antigens of the pathogen, where upon excitation with light of the appropriate wavelength and power, singlet oxygen radicals are generated, resulting in damage or destruction of the pathogen. In another instance, the modified red blood cells are used to deliver a therapeutic agent to the pathogen, known or suspected to have infected a subject.

A photoactivatable molecule, such as a porphyrin, is conjugated, via an amide linkage, to a monoclonal antibody known to exhibit selective binding to an antigen expressed on the surface of a pathogen, e.g., the bacterium *Staphylococcus aureus*. The antibody is also conjugated to a quenching agent such as a Dabcyl (4-(4'-dimethylaminophenylazo)benzoyl) group, by reaction with a commercially available agent such as dabcyl chloride. This target-binding agent is further modified by the addition of a suitable metal ion to an aqueous solution of the composition. The metal binds to the coordination pocket of the porphyrin ring-system and also coordinates the amine or azo group of the quenching group, ensuring that the quenching agent remains sufficiently close to the photoactivatable molecule to allow energy transfer and thereby quench the generation of singlet oxygen.

Next, red blood cells are isolated from the subject in need of treatment. In cases where it is desirable to use a therapeutic agent, the cells are loaded with the therapeutic agent (e.g., an antibiotic, antifungal, antiparasitic, or antiviral), such as ciprofloxacin, and biotinylated. The antibody is also conjugated with biotin and then linked to the biotinylated red blood cells by a streptavidin bridge to form an assembled target-binding agent. The assembled target-binding agent is mixed with a suitable excipient for intravenous administration to the subject. A therapeutically effective amount of this target-binding agent is administered to the subject.

Binding of the antibody to its pathogen target then disrupts the coordination binding environment, releasing the quencher molecule from the metal and allowing the quencher molecule to move away from the photoactivatable molecule, thereby activating the target-binding agent. After a sufficient time for the target-binding agent to bind to the intended target and clear from normal tissue, a light source of the appropriate wavelength is used to deliver a therapeutically useful amount to light to an area that includes the lesion. The light causes the excitation of the photoactivable moiety, resulting in the production of a singlet oxygen radical molecule. The singlet oxygen radical molecule may act on pathogen directly, thereby damaging or destroying the pathogen. Alternatively, the singlet oxygen radical disrupts the cell membrane of the red blood cell, which has been loaded with the therapeutic agent, thereby releasing the therapeutic agent. The therapeutic agent is contacted with the pathogen causing damage, death or inactivation of the pathogen.

The efficacy of treatment is assessed by reduction in the number of pathogen cells or absence of the pathogen cells; or reduction one or more of the symptoms associated with the infection.

Example 3

Imaging a Target Tissue of a Subject

In this example, the modified red blood cells are used to transport an imaging agent, i.e. fluorescent molecule or radiocontrast dye, to a particular tissue or cell-type. A photoactivatable molecule, such as a porphyrin, is conjugated, via an amide linkage, to a monoclonal antibody known to exhibit selective binding to an antigen expressed in a particular tissue of the subject. The antibody is also conjugated to a quenching agent such as a Dabcyl (4-(4'-dimethylaminophenylazo)benzoyl) group, by reaction with a commercially available agent such as dabcyl chloride. This target-binding agent is further modified by the addition of a suitable metal ion to an aqueous solution of the composition. The metal binds to the coordination pocket of the porphyrin ring-system and also coordinates the amine or azo group of the quenching group, ensuring that the quenching agent remains sufficiently close to the photoactivatable molecule to allow energy transfer and thereby quench the generation of singlet oxygen.

Next, red blood cells are isolated from the subject in need of imaging. The cells are loaded with the imaging agent and biotinylated. The antibody is also conjugated with biotin and then linked to the biotinylated red blood cells by a streptavidin bridge to form an assembled modified red blood cell. The assembled modified red blood cell is mixed with a suitable excipient for intravenous administration to the subject. A therapeutically effective amount of this modified red blood cell is administered to the subject.

Binding of the antibody to its bacterial target then disrupts the coordination binding environment, releasing the quencher molecule from the metal and allowing the quencher molecule to move away from the photoactivatable molecule, thereby activating the target-binding agent. After a sufficient time for the target-binding agent to bind to the intended target and clear from normal tissue, a light source of the appropriate wavelength is used to deliver a useful amount to light to an area that includes the lesion. The light causes the excitation of the photoactivable moiety, resulting in the production of a singlet oxygen radical molecule, which disrupts the cell membrane of the red blood cell, thereby releasing the imaging agent, e.g., radiocontrast dye. The imaging agent is detected using X-ray, CT, or other means.

EQUIVALENTS

The present disclosure is not to be limited in terms of the particular embodiments described in this application, which are intended as single illustrations of individual aspects of. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

For any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. All language such as "up to," "at least," "greater than," "less than," and the like include the number recited and refer to ranges which can be subsequently broken down into subranges as discussed above. Finally, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The various aspects and embodiments disclosed herein are for purposes of illustration and are not intended to be limiting, with the true scope and spirit being indicated by the following claims.

The various aspects and embodiments disclosed herein are for purposes of illustration and are not intended to be limiting, with the true scope and spirit being indicated by the following claims.

All publications and patent applications cited in this specification are herein incorporated by reference to the extent not inconsistent with the description herein and for all purposes as if each individual publication or patent application were specifically and individually indicated to be incorporated by reference for all purposes.

The herein described components (e.g., steps), devices, and objects and the description accompanying them are used as examples for the sake of conceptual clarity and that various configuration modifications using the disclosure provided herein are within the skill of those in the art. Consequently, as used herein, the specific exemplars set forth and the accompanying description are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural or singular terms herein, those having skill in the art can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A method for detecting a target in a biological sample, comprising:
adding to the biological sample a red blood cell that binds to the target, the red blood cell including one or more fusion molecules, and at least one target-binding agent including a target recognition moiety, wherein the target recognition moiety is configured to recognize one or more target cells, and wherein the one or more fusion molecules are configured to promote fusion of the red blood cell with the one or more target cells; and detecting the modified red blood cell.

2. The method of claim 1, wherein the red blood cell expresses one or more of the at least one target-binding agent and the one or more fusion molecules.

3. The method of claim 1, wherein the at least one target-binding agent and the one or more fusion molecules are associated with the cell surface of the red blood cell.

4. The method of claim 1, wherein the one or more fusion molecules includes at least one of antigen; ligand; receptor; polyamide; peptide; carbohydrate; oligosaccharide; polysaccharide; low density lipoprotein (LDL); an apoprotein of LDL; steroid; steroid derivative; hormone; hormone-mimic; lectin; drug; antibiotic; aptamer; DNA; RNA; lipid; an antibody; or an antibody-related polypeptide.

5. The method of claim 1, wherein the one or more fusion molecules is a syncytin-1 protein.

6. The method of claim 1, wherein the target recognition moiety includes at least one of antigen; ligand; receptor; polyamide; peptide; carbohydrate; oligosaccharide; polysaccharide; low density lipoprotein (LDL); an apoprotein of LDL; steroid; steroid derivative; hormone; hormone-mimic; lectin; drug; antibiotic; aptamer; DNA; RNA; lipid; an antibody; or an antibody-related polypeptide.

7. The method of claim 1, further comprising one or more activatable molecular markers, wherein the one or more activatable molecular markers is configured to be activated by an interaction of the modified red blood cell with the one or more target cells to produce a detectable response.

8. The method of claim 7, wherein the one or more activatable molecular markers is a photoactivatable molecular marker and the detectable response is the production of reactive singlet oxygen molecules.

9. The method of claim 7, wherein the modified red blood cell is genetically engineered to express the one or more activatable molecular markers.

10. The method of claim 9, wherein the one or more activatable molecular markers is an aptamer based molecular beacon.

11. The method of claim 1, wherein the at least one target-binding agent further comprises a photoactivatable molecule and a quencher molecule coupled to the target recognition moiety, wherein the at least one target-binding agent is configured to emit at least one singlet oxygen radical molecule upon exposure to light of a suitable wavelength when the at least one target-binding agent is bound to the one or more target cells.

12. The method of claim 11, wherein the photoactivatable molecule and the quencher molecule include a linker.

13. The method of claim 12, wherein the linker includes at least one of an oligonucleotide or a sulfonic acid.

14. The method of claim 11, wherein the photoactivatable molecule includes at least one of a porphyrin; chlorin; bacteriochlorin; isbacteriochlorin; phthalocyanine; napthalocyanine; porphycene; porphycyanine; tetra-macrocyclic compound; poly-macrocyclic compound; pyropheo-phorbide; pentaphyrin; sapphyrin; texaphyrin; metal complexe; tetrahydrochlorin; phonoxazine dye; phenothiazine; chaloorganapyrylium dye; rhodamine; fluorescene; azoporphyrin; benzochlorin; purpurin; chlorophyll; verdin; triarylmethane; angelicin; chalcogenapyrillium dye; chlorin; chlorophyll; coumarin; cyanine; ceratin daunomycin; daunomycinone; 5-iminodauno-mycin; doxycycline; furosemide; gilvocarcin M; gilvocarcin V; hydroxy-chloroquine sulfate; lumidoxycycline; mefloquine hydrochloride; mequitazine; merbromin (mercurochrome); primaquine diphosphate; quinacrine dihydrochloride; quinine sulfate; tetracycline hydrochloride; flavin; alloxazine; flavin mononucleotide; 3-hydroxyflavone; limichrome; limitlavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin; metallo-porphyrin; metallophthalocyanine; methylene blue derivative; naphthalmide; naphthalocyanine; pheophorbide; pheophytin; photosensitizer dimer and conjugate; phthalocyanine; porphycene; quinone; retinoid; rhodamine; thiophene; verdin; vitamin; or xanthene dye.

15. The method of claim 11, wherein the quencher molecule includes at least one of: 4-(4'-dimethylamino-phenylazo)benzoic acid (DABCYL); dabcyl succinimidyl ester; 4-(4'-dimethylamino-phenylazo)sulfonic (DABSYL); dabsyl succinimidyl ester; tetramethyl-rhodamaine (TAMRA); 4-[(4-nitrophenyl)diazinyl]-phenylamine and 4-[4-nitrophenyl)diazinyl]-naphthylamine; dabcylnitro-thiazole; 6-(N-[7-nitrobenz-2-oxa-1,3-diazol-4-yl]amino)hexanoic acid; 6-carboxy-X-rhodamine (ROX); QSY-7; 2-[4-(4-nitrophenylazo)-N-ethylphenyl-amino]ethanol (Disperse Red 1); 2-[4-(2-chloro-4-nitrophenyl-azo)-N-ethylphenylamino]-ethanol (Disperse Red 13); tetrarhodamine isothiocyanate (TRITC); allophycocyanin; β-carotene; diarylrhodamine derivatives, QSY 7, QSY 9, QSY 21 dyes; QSY 35 acetic acid succinimidyl ester; QSY 35 iodoacetamide; aliphatic methylamine; napthalate; Reactive Red 4; or Malachite Green.

16. The method of claim 1, wherein the red blood cell includes a reticulocyte; a red blood cell; or a fusion between a red blood cell between a red blood cell autologous to a subject and one or more allogeneic erythrocytes, liposomes or artificial vesicles.

17. The method of claim 1, wherein the red blood cell is genetically engineered to express one or more protein-based pharmaceutical molecules or one or more RNA-based pharmaceutical molecules.

18. The method of claim 1, wherein the red blood cell is loaded with one or more pharmaceutical or imaging molecules, or one or more viruses.

19. The method of claim 18, wherein the one or more pharmaceutical molecules includes at least one of an antibiotic, an antiviral agent, an antifungal agent, an anti-parasitic agent, an antibody, an antibody-related polypeptide, a antineoplastic agent; a protein-based pharmaceutical; or an RNA or DNA-based pharmaceutical.

20. The method of claim 19, wherein the antineoplastic agent includes at least one of an alkylating agent; cisplatin; carboplatin; oxaliplatin; mechlorethamine; cyclophosphamide; chlorambucil; anti-metabolite compound; azathioprine; mercaptopurine; alkaloid; terpenoid; vinca alkaloid; vincristine; vinblastine; vinorelbine; vindesine; podophyllotoxin; taxane; docetaxel; paclitaxel; topoisomerase inhibitor; camptothecin; irinotecan; topotecan; amsacrine; etoposide; etoposide phosphate; teniposide; epipodophyllotoxins; anti-tumour antibiotic; dactinomycin; trastuzumab, cetuximab, rituximab; bevacizumab; finasteride; tamoxifen; gonadotropin-releasing hormone agonist (GnRH); or goserelin.

21. The method of claim 19, wherein the antibiotic includes at least one of aminoglycoside; amikacin; gentamicin; kanamycin; neomycin; netilmicin; steptomycin; tobramycin; ansamycin; geldanamycin; herbimycin; carbacephem; loracarbef; carbacepenem; ertapenem; doripenem; imipenem/cilastatin; meropenem; cephalosporin; cefadroxil; cefazolin; cefalotin or cefalothin; cefalexin; cefaclor; cefamandole; cefoxitin; cefprozil; cefuroxime; cefixime; cefdinir; cefditoren; cefoperazone; cefotaxime; cefpodoxime; ceftazidime; ceftibuten; ceftizoxime; ceftriaxone; cefepime; ceftobiprole; glycopeptide; teicoplanin; vancomycin; macrolide; azithromycin; clarithromycin; dirithromycin; erythromycin; roxithromycin; troleandomycin; telithromycin; spectinomycin; monobactam; aztreonam; penicillin; amoxicillin; ampicillin; azlocillin; carbenicillin; cloxacillin; dicloxacillin; flucloxacillin; mezlocillin; meticillin; nafcillin; oxacillin; penicillin, piperacillin, ticarcillin; bacitracin; colistin; polymyxin B; quinolones; ciprofloxacin; enoxacin; gatifloxacin; levofloxacin; lomefloxacin; moxifloxacin; norfloxacin; ofloxacin; trovafloxacin; sulfonamide; mafenide; prontosil (archaic); sulfacetamide; sulfamethizole; sufanilimide (archaic); sulfasalazine; sulfisoxazole; trimethoprim; trimethoprim-sulfamethoxazole (co-trimoxazole) (TMP-SMX); tetracycline; demeclocycline; doxycycline; minocycline; oxytetracycline; tetracycline; arsphenamine; chloramphenicol; clindamycin; lincomycin; ethambutol; fosfomycin; fusidic acid; furazolidone; isoniazid; linezolid; metronidazole; mupirocin; nitrofuantoin; platensimycin; purazinamide; quinupristin/dalfopristin; rifampin or rifampicin; or tinidazole.

22. The method of claim 19, wherein the antiviral agent includes at least one of thiosemicarbazone; metisazone; nucleoside, nucleotide; acyclovir; idoxuridine; vidarabine; ribavirin; ganciclovir; famciclovir; valaciclovir; cidofovir; penciclovir; valganciclovir; brivudine; ribavirin, cyclic amines; rimantadine; tromantadine; phosphonic acid derivatives; foscarnet; fosfonet; protease inhibitor; saquinavir; indinavir; ritonavir; nelfinavir; amprenavir; lopinavir; fosamprenavir; atazanavir; tipranavir; nucleoside or nucleotide reverse transcriptase inhibitor; zidovudine; didanosine; zalcitabine; stavudine; lamivudine; abacavir; tenofovir disoproxil; adefovir dipivoxil; emtricitabine; entecavir; non-nucleoside reverse transcriptase inhibitor; nevirapine; delavirdine; efavirenz; neuraminidase inhibitors; zanamivir; oseltamivir; moroxydine; inosine pranobex; pleconaril; or enfuvirtide.

23. The method of claim 19, wherein the anti-fungal agent includes at least one of allylamine; terbinafine; antimetabolite; flucytosine; azole; fluconazole; itraconazole; ketoconazole; ravuconazole; posaconazole; voriconazole; glucan synthesis inhibitor; caspofungin; micafungin; anidulafungin; polyene; amphotericin B; amphotericin B Lipid Complex (ABLC); amphotericin B Colloidal Dispersion (ABCD); liposomal amphotericin B (L-AMB); liposomal nystatin; or griseofulvin.

24. The method of claim 19, wherein the anti-parasitic agent includes at least one of antiprotozoal agent; eflornithine; furazolidone; melarsoprol; metronidazole; ornidazole; paromomycin sulfate; pentamidine; pyrimethamine; tinidazole; antimalarial agent; quinine; chloroquine; amodiaquine; pyrimethamine; sulphadoxine; proguanil; mefloquine; halofantrine; primaquine; artemesinin and derivatives thereof; doxycycline; clindamycin; benznidazole; nifurtimox; antihelminthics; albendazole; diethylcarbamazine; mebendazole; niclosamide; ivermectin; suramin; thiabendazole; pyrantel pamoate; levamisole; piperazine family; praziquantel; triclabendazole; octadepsipeptide; and emodepside.

* * * * *